United States Patent
Hatamian

(10) Patent No.: US 12,370,546 B2
(45) Date of Patent: *Jul. 29, 2025

(54) SANDWICH IMMUNOASSAY DEVICES USING ANTIBODIES SPECIFIC TO THE EXOSOMES CONTAINING TARGET ANALYTES

(71) Applicant: 2Pi-Sigma Corp., Newport Beach, CA (US)

(72) Inventor: Mehdi Hatamian, Mission Viejo, CA (US)

(73) Assignee: 2Pi-Sigma Corp., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/560,402

(22) PCT Filed: May 18, 2022

(86) PCT No.: PCT/US2022/029898
§ 371 (c)(1),
(2) Date: Nov. 13, 2023

(87) PCT Pub. No.: WO2022/245990
PCT Pub. Date: Nov. 24, 2022

(65) Prior Publication Data
US 2024/0253035 A1    Aug. 1, 2024

Related U.S. Application Data

(63) Continuation of application No. 17/747,854, filed on May 18, 2022, now Pat. No. 11,731,130.

(60) Provisional application No. 63/189,682, filed on May 18, 2021.

(51) Int. Cl.
*B01L 3/00* (2006.01)
*B01L 9/00* (2006.01)
*G01N 27/327* (2006.01)
*G01N 33/543* (2006.01)

(52) U.S. Cl.
CPC .......... *B01L 3/502715* (2013.01); *B01L 9/52* (2013.01); *G01N 27/3275* (2013.01); *G01N 33/54388* (2021.08); *B01L 2200/026* (2013.01); *B01L 2200/16* (2013.01); *B01L 2300/0681* (2013.01); *B01L 2300/069* (2013.01); *B01L 2300/0825* (2013.01); *B01L 2400/0406* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 7,344,893 B2 | 3/2008 | Kirkegaard et al. | |
| 8,003,407 B2 | 8/2011 | Zhou et al. | |
| 10,739,297 B2 | 8/2020 | Hatamian | |
| 11,731,130 B2 | 8/2023 | Hatamian | |
| 2005/0214951 A1* | 9/2005 | Nahm | G01N 21/6402 436/514 |
| 2008/0032420 A1* | 2/2008 | Lambert | G01N 33/54373 436/514 |
| 2015/0010913 A1 | 1/2015 | Ohta et al. | |
| 2016/0320390 A1* | 11/2016 | Newman | C07K 16/40 |
| 2020/0319158 A1 | 10/2020 | Gorewit | |
| 2021/0033605 A1 | 2/2021 | Hollidt et al. | |

FOREIGN PATENT DOCUMENTS

| | | | | |
|---|---|---|---|---|
| JP | 2013185921 A | 9/2013 | | |
| RU | 2682721 C2 | 3/2019 | | |
| WO | WO-9532414 A1 * | 11/1995 | ....... | G01N 33/54366 |
| WO | WO-03085403 A1 * | 10/2003 | ............. | G01N 33/53 |
| WO | WO 2022/245990 | 11/2022 | | |

OTHER PUBLICATIONS

Harvard Health Publications. Harvard Medical School. PSA: Prostate-Specific Antigen, Persisting Scientific Ambiguities, (2009), (15 pages) https://www.health.harvard.edu/newsletter_article/PSA-Prostate-Specific-Antigen-Persisting-Scientific-Ambiguities. Accessed: Jun. 28, 2024. (Year: 2009).*
Sun et al., Mouse Organ-Specific Proteins and Functions, Cells, 10, (2021), (16 pages) (Year: 2021).*
Oliviera-Rodríquez et al., Point of Care detection of extracellular vesicles: Sensitivity optimization and multiple-target detection, Biosensors and Bioelectronics, 87, (2017), p. 38-45 (Year: 2017).*
U.S. Appl. No. 18/513,651, filed Nov. 20, 2023, Hatamian, Mehdi.
International Search Report and Written Opinion of PCT/US2022/029898, mailing date Jul. 25, 2022, 2PI-Sigma Corp.
Portions of prosecution history of U.S. Appl. No. 17/747,854, Apr. 4, 2023, Hatamian, Mehdi.
Oliveira-Rodriguez, Myriam, et al., "Development of a rapid lateral flow immunoassay test for detection of exosomes previously enriched from cell culture medium and body fluids", Journal of Extracellular Vesicles, 5:1, 31803, published Aug. 12, 2016, pp. 1-10.

(Continued)

*Primary Examiner* — Ellen J Marcsisin
(74) *Attorney, Agent, or Firm* — Makoui Law, PC; Ali Makoui

(57) ABSTRACT

A lateral flow assay device comprises a test strip to receive a quantity of fluid comprising a quantity of exosomes and detect the presence of a target analyte on the surface of the exosomes. The test strip comprises a conjugate pad that contains a set of one or more types of tetraspanin binding reagents conjugated with a label. Each type of tetraspanin binding reagent is configured to bind with a corresponding type of exosome tetraspanin and form an immunocomplex comprising an exosome. The conjugate pad is fluidly connected to a membrane. The membrane comprises a test line comprising an immobilized binding reagent to the target analyte. The immobilized binding reagent to the target analyte is configured to bind to a protein of the target analyte on the surface of an exosome in an immunocomplex comprising the exosome.

9 Claims, 47 Drawing Sheets

(56) References Cited

OTHER PUBLICATIONS

Moura Silio Lima, et al. "Multiplex detection and characterization of breast cancer exosomes by magneto-actuated immunoassay," Talanta 211, available online Dec. 24, 2019, pp. 1-9.

Serrano-Pertierra, Esther, et al., "Extracellular Vesicles: Current Analytical Techniques for Detection and Qualification", Biomolecules, vol. 10, No. 6, May 28, 2020, pp. 1-19.

Author unknown, Extended European search report of the counterpart European patent application, European Patent Office, Apr. 11, 2025, 8 pages.

* cited by examiner

| Exosome Protein | Tumor | Body Fluid |
|---|---|---|
| NY-ESO-1 | Lung | Plasma |
| PKG1, RALGAPA2, NFX1, TJP2 | Breast | Plasma |
| Her2 | Breast | Plasma |
| Glypican-1 | Breast | Serum |
| Glypican-1 | Pancreatic | Serum |
| Glypican-1 | Colorectal | Plasma |
| CEA | Colorectal | Serum |
| AMPN, VNN1, PIGR | Cholangiocarcinoma | Serum |
| PSA | Prostate | Plasma |
| GGT1 | Prostate | Serum |
| CD24, EpCAM, CA-125 | Ovarian | Plasma |

FIG. 2
Prior Art

SANDWICH IMMUNOASSAY DEVICES USING ANTIBODIES SPECIFIC TO THE EXOSOMES CONTAINING TARGET ANALYTES

CLAIM OF BENEFIT TO PRIOR APPLICATIONS

This application is a national stage application of PCT Application PCT/US2022/029898, filed on May 18, 2022, published as WO 2022/245990. PCT Application PCT/US2022/029898_claims the benefit of U.S. patent application Ser. No. 17/747,854, filed on May 18, 2022, issued as U.S. Pat. No. 11,731,130. PCT Application PCT/US2022/029898 and U.S. patent application Ser. No. 17/747,854 claim the benefit of U.S. Provisional Patent Application Ser. No. 63/1890,682, filed on May 18, 2021. The contents of PCT Application PCT/US2022/029898, published as WO 2022/245990, U.S. patent application Ser. No. 17/747,854, issued as U.S. Pat. No. 11,731,130, and U.S. Provisional Patent Application 63/1890,682 are hereby incorporated by reference.

BACKGROUND

An immunoassay device is a device used for performing tests that detect the presence (or absence) of a target analyte in a sample fluid. The immunoassay devices include, for example, enzyme-linked immunosorbent assay (ELISA) devices, lateral flow assay (LFA) devices, etc. The immunoassay devices may have different formats. A sandwich format immunoassay device uses two sets of antibodies to capture and detect a target analyte. A competitive format immunoassay device may be used for detecting analytes that cannot simultaneously bind to two antibodies.

Sandwich format ELISA devices include microplates with a group of wells, for example, 96 wells, 384 wells, 1536 wells, etc. The capture antibody is bound to the bottom of the microplate's wells and binds to one epitope of the target analyte (if any). The detection antibody then binds to the target analyte at a different epitope and is conjugated to an enzyme that enables detection. Enzymes on the detection antibody may interact with a substrate to produce a color change.

An LFA (also referred to as lateral flow immunochromatographic assay or lateral flow dipstick immunoassay) device typically includes a series of capillary pads for transporting fluid. The prior art sandwich format LFA devices are used for detecting analytes that can bind to at least two different antibodies. In the prior art sandwich format LFA devices, a sample pad may be used to receive a quantity of fluid (referred to as the sample fluid) that may include the target analyte. The sample fluid is then transported to an adjacent conjugate pad by capillary action. The conjugate pad may contain a solubilized antibody labeled with a detector such as colloidal gold nanoparticles. The antibody is specific to the target analyte of interest in the sample fluid. As the sample fluid flows through the conjugate pad, the analyte (if any) in the sample fluid binds with the labeled antibody on the conjugate pad and forms an immunocomplex.

The immunocomplex then flows from the conjugate pad into an adjacent membrane (or membrane pad). The membrane has a test area, or test line, that contains an immobilized unlabeled antibody. As the immunocomplex moves over the test area, the immunocomplex binds with the immobilized antibody on the test area, resulting in a colored test line. When the sample fluid does not include the target analyte, no immunocomplex is formed on the conjugate pad and no immunocomplex binds with the immobilized antibody on the test area. As a result, the test line does not change color.

An LFA device may also include a control line on the membrane. In a sandwich assay format, the control line may contain an immobilized antibody that binds to the free antibodies labeled with the detector resulting in a colored control line, which confirms that the test has operated correctly regardless of whether or not the target analyte has been present in the sample.

In a competitive format ELISA device, a reference target analyte is bound to the bottom of microplate wells. Sample and antibody are then added to the wells, and if there is target analyte present in the sample, it competes with reference target analyte for binding to the antibody. Unbound material is then washed away. The more target analyte in the sample, the less antibody ends up bound to the bottom of the wells by the reference target analyte, and the lower the signal.

The sample pad and the conjugate pad in a competitive format LFA device are similar to the sample pad and the conjugate pad in the sandwich format LFA device. In the competitive assay format, the test line contains immobilized analyte molecules. If the sample liquid does not contain the analyte, the labeled antibody flows from the conjugate pad into the test line and binds to the analyte at the test line, resulting in a colored test line that indicates the lack of the target analyte in the sample liquid. If, on the other hand, the target analyte is present in the sample liquid, the analyte binds to the labeled antibodies on the conjugate pad and prevents the labeled antibody to bind to the analyte at the test line, resulting in the lack of color on the test line. In a competitive assay format, the control line may contain an immobilized analyte that binds to the free antibodies labeled with the detector resulting in a colored control line, which confirms that the test has operated correctly regardless of whether or not the target analyte has been present in the sample.

BRIEF DESCRIPTION OF THE DRAWINGS

The various embodiments of the present sandwich immunoassay devices using antibodies specific to the exosomes containing target analytes now will be discussed in detail with an emphasis on highlighting the advantageous features. These embodiments depict the novel and non-obvious sandwich immunoassay devices using antibodies specific to the exosomes containing target analytes shown in the accompanying drawings, which are for illustrative purposes only. These drawings include the following figures, in which like numerals indicate like parts:

FIG. 2 illustrates examples of the exosome proteins that are specific to certain tumors according to prior art;

DETAILED DESCRIPTION

Figure 1A:
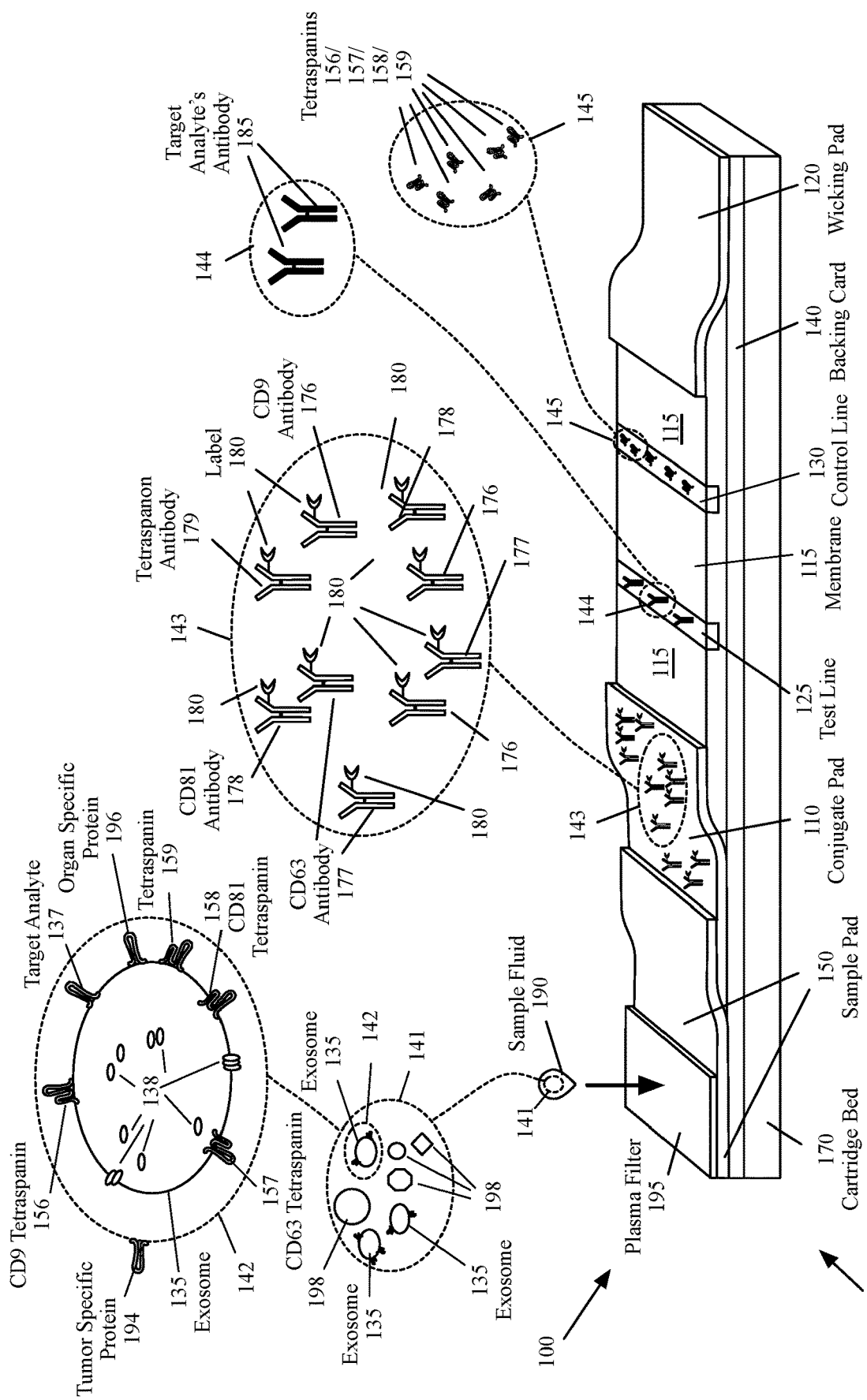
FIGS. 1A-1D are functional diagrams illustrating an LFA device and a method that that uses one or more antibodies specific to an exosome containing the target analyte as the detection antibodies and an antibody specific to the target analyte as the capture antibody, according to various aspects of the present disclosure.
Figure 1B:
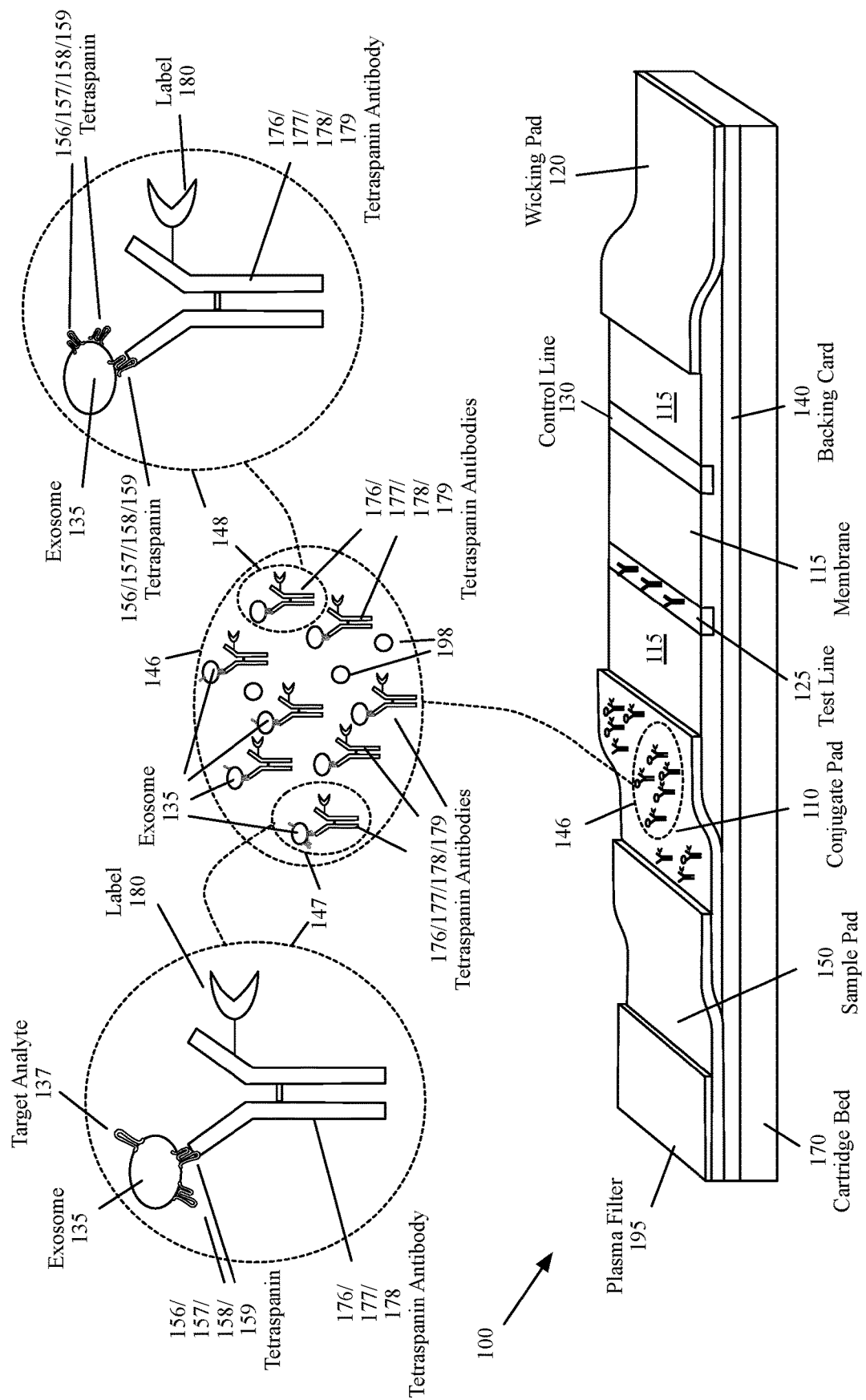
Figure 1C:
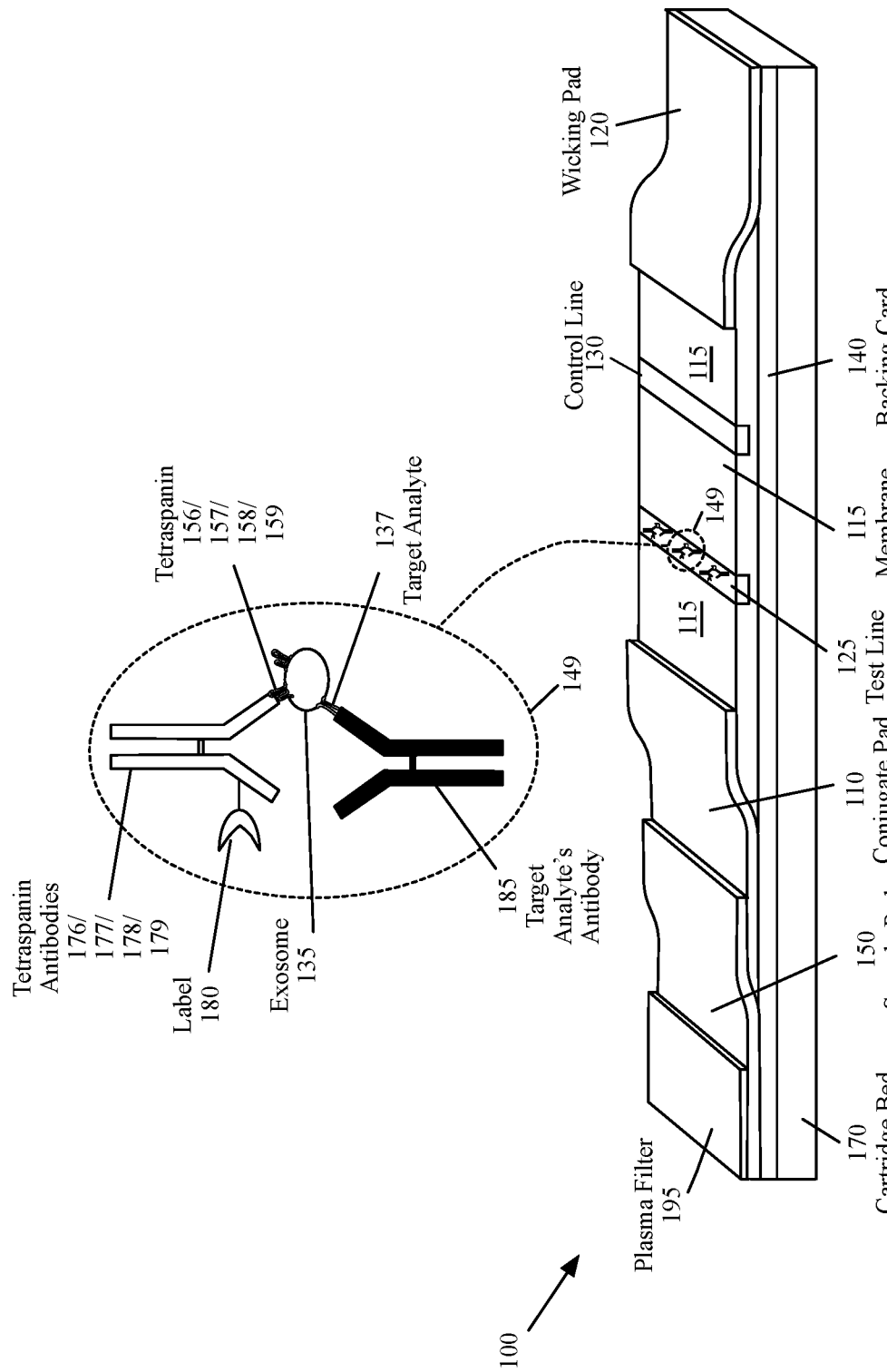
Figure 1D:
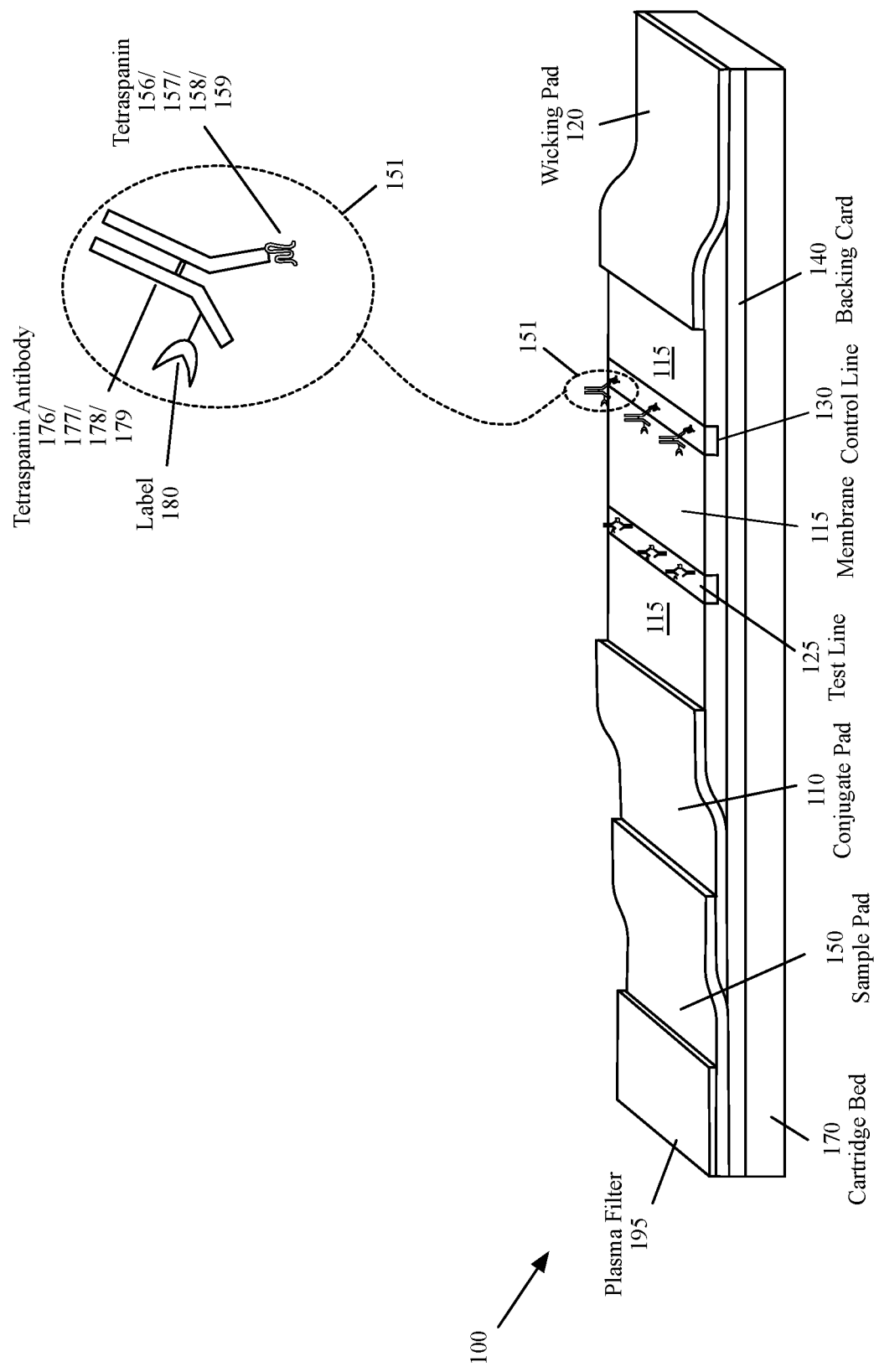

One aspect of the present embodiments includes the realization that a sandwich format immunoassay requires two antibodies that are specific to the target analyte such that the antibodies, to a great extent, attach to the target analyte and do not attach to other molecules. Otherwise, the other molecules that also attach to the antibodies may become sources of error. For some target analytes, however, there may only be one specific antibody. One technique to detect the presence (or absence) of these target analytes is to use a competitive format assay device. The competitive format assay devices are, however, not as accurate as the sandwich format assay devices. Another drawback of the competitive format assay devices is the need to have the physical target analyte material itself in order to use it as the reference target analyte on the bottom of the plates (for ELISA devices) and to use it on the test line (for LFA devices).

Some of the present embodiments solve the aforementioned problems by using an antibody to capture exosomes in the sample liquid. Exosomes are extracellular vesicles that are released from cells. The exosomes may contain different proteins depending on their host cell. The most common exosome marker proteins include tetraspanin proteins, such as CD9, CD63, CD81, and CD82, which are present on the surface of the exosomes. The exosomes may also carry markers from the cells that release them. For some target analytes, such as, for example, and without limitations, cancer cells' proteins, the exosomes released by the cells may include the markers for the proteins that are the targets of an assay.

Some of the present embodiments provide a method and an immunoassay device that receive a quantity of fluid comprising a quantity of exosomes and detect the presence of a target analyte on the surface of the exosomes. The immunoassay device comprises a detection site and a capture site. The method and the immunoassay device perform a fluid transfer between the detection site and the capture site. The mechanism of the transfer of the fluid between the site where the detection action takes place and the site where the capture action takes place may be by capillary action (e.g., an LFA device or a microfluidic device), a microfluidic chip or medium, an automated liquid handling system (e.g., the liquid handling used in an automated ELISA device), an automated liquid handling system in combination with a microfluidic device, or manual transfer such as pipetting procedures used in standard ELISA. In some of these immunoassay devices the detection action and the capture action are performed on different sites on the device. For example, in the LFA devices, the detection action is performed on the conjugate pad and the capture action is performed on one or more test lines. In some of these immunoassay devices the detection action and the capture action may be performed on the same site of the device. For example, in the ELISA devices, the detection action and the capture action may be performed in the same well of the ELISA device.

The immunoassay devices of some of the present embodiments perform the detection action by using binding reagents (e.g., antibodies) to the tetraspanin, such as, CD9 protein, CD63 protein, CD81 protein, CD82 protein, etc., to detect exosomes in a sample liquid. These immunoassay devices may use one or more exosome binding reagents. Different exosomes may bind to one or more binding reagents for the CD9, CD63, CD81, CD82, etc., proteins. These immunoassay devices perform the capture action by using a second binding reagent (e.g., an antibody) that is specific to the target analyte, which is used to immobilize and capture the exosomes that carry the target analyte.

The immunoassay devices of some of the present embodiments perform the detection action by using a binding reagent (e.g., an antibody) specific to the target analyte to detect the target analyte in a sample liquid. These immunoassay devices perform the capture action by using one or more binding reagents (e.g., antibodies) to the tetraspanin, such as, CD9 protein, CD63 protein, CD81 protein, CD82 protein, etc., to immobilize and capture the exosomes that carry the target analyte. Different exosomes may bind to one or more antibodies for the CD9, CD63, CD81, CD82, etc., proteins.

Several non-limiting examples of these methods and immunoassay devices are described in Section I with reference to LFA devices and in Section II with reference to ELISA devices. The remaining detailed description describes the present embodiments with reference to the drawings. In the drawings, reference numbers label elements of the present embodiments. These reference numbers are reproduced below in connection with the discussion of the corresponding drawing features.

I. LFA Device that Captures a Target Analyte by Using an Antibody Specific to an Exosome Containing the Target Analyte FIGS. 1A-1D are functional diagrams illustrating an LFA device 100 and a method that uses one or more antibodies specific to an exosome containing the target analyte as the detection antibodies and an antibody specific to the target analyte as the capture antibody, according to various aspects of the present disclosure. The LFA device 100 may be a portable device (e.g., a handheld device or benchtop device) that is used to analyze a sample fluid 190 (also referred to as matrix) to determine the presence and/or the amount of one or more analytes (referred to as target analytes). The term analyte refers to the molecule detected by the immunoassay device.

With reference to FIGS. 1A-1D, the LFA device 100 may include a replaceable cartridge that may be intended for single use. For example, the components shown in FIGS. 1A-1D may be part of a disposable cartridge of the LFA device 100. The LFA device 100 may include a backing card 140 that may be used to assemble different portions of the sample pad 150, the conjugate pad 110, the membrane 115, and/or the wicking pad 120.

The backing card 140, in some embodiments, may be a continuous piece that may go under the pads 150, 110, 115, and 120. In other embodiments, each pad may have a separate backing card. For example, during the manufacturing of the device, a roll or sheet of backing material may be used such that the width of the roll or the sheet is the same as (or is cut to be the same as) the length of the lateral flow assay cartridge (i.e., in the pictured orientation, from the left end of the sample pad 150 to the right end of the wicking pad 120). The pads 115, 110, 150, and 120 are then placed on the backing card with the proper overlaps (e.g., as shown in FIGS. 1A-1D). The pads may, for example, be connected to the backing card with a two sided tape or a glue. The pads and the attached backing card may then be cut into separate strips and each strip may be used to make a different LFA device.

Alternatively, each pad may be separately connected to a corresponding backing card. The pads with the corresponding backing cards may then be assembled over each other with the proper overlaps to make a LFA device. The LFA device 100 may include a housing. In FIGS. 1A-1D, only a portion of the housing that includes the cartridge bed 170 is shown for clarity.

The sample fluid 190 applied to the LFA device 100 may include human or animal bodily fluid, such as, for example, and without limitations, one or more of blood, urine, serum, plasma, saliva, sweat, milk, mucous, semen, vaginal or urethral secretions, cerebrospinal fluid, etc. The sample may naturally be a liquid, may be a liquid diluted with another liquid, such as water, or may have originally been in a solid form (e.g., a tissue sample) and is treated to be in liquid form for application to the LFA device 100. The target analytes, in some of the present embodiments, may be substances such as, for example, and without limitations, proteins, haptens, enzymes, hormones, infectious disease agents, immunoglobulins, polynucleotides, steroids, drugs, nucleic acids, markers for gene mutations, antigens, simple organic molecules, etc.

The LFA device 100 may include a sample pad (also referred to as sample strip or sample receiving member) 150. The sample pad 150 may be made of natural and/or synthetic porous, microporous, mesoporous, or macroporous materials capable of receiving a sample fluid and laterally conducting the sample fluid toward the conjugate pad 110 by capillary action. The sample pad 150 may be made of a material such as, for example, and without limitations, cellulose, nitrocellulose, paper, silica, cotton, glass (e.g., glass fiber), or synthetic material (e.g., polyester, polyethylene, polymers, rayon, nylon, etc.). Depending on the type of the sample (e.g., urine, saliva, blood, serum, plasma, sweat, milk, mucous, semen, vaginal or urethral secretions, cerebrospinal fluid, etc.), the sample pad 150 may be treated by a buffer (e.g., an organic compound such as tris or tris(hydroxymethyl)aminomethane) to mitigate sample variabilities (pH, protein concentration, viscosity, salt concentration, etc.). During the manufacture of the sample pad 150, the buffer compound may be coated, impregnated, or otherwise applied or deposited on the sample pad 150 and then dried. The embodiments that the sample fluid includes blood may include a plasma filter 195.

The LFA device 100 may include a conjugate pad 110 that is fluidically connected (i.e., capable of receiving fluid by capillary action) to the sample pad 150. In the depicted embodiment, the sample pad 150 is in contact with and partially covers the conjugate pad 110. In other embodiments, the sample pad 150 may be in more contact or less contact with the conjugate pad 110 in order to provide slower or faster binding reagent and/or conjugate release respectively. A sample fluid that is applied to the sample pad 150 may be laterally transferred from the sample pad 150 to the conjugate pad 110 by capillary action.

The conjugate pad 110 may be made of natural and/or synthetic porous, microporous, mesoporous, or macroporous materials capable of receiving the sample fluid from the sample pad 150. The conjugate pad 110 may be made of material such as, for example, and without limitations, glass (e.g., glass fiber), cellulose, nitrocellulose, paper, silica, cotton, or synthetic material (e.g., polyester, polyethylene, polymers, rayon, nylon, etc.).

In the example of FIGS. 1A-1D, the sample fluid 190 may be a fluid such as, for example, and without limitations, blood, urine, serum, plasma, saliva, sweat, milk, mucous, semen, vaginal or urethral secretions, cerebrospinal fluid. As shown in the expanded view 141 of FIG. 1A, the sample fluid 190 may include, among other components, the exosomes 135. When the sample fluid 190 includes blood, the other components 198 may include, for example, red blood cells, white blood cells, platelets, plasma, etc.

The exosomes 135 are extracellular vesicles that are produced by most cells. The exosomes may be found in blood, urine, or cerebrospinal fluid. The exosomes may also be released in vitro by cultured cells into their growth medium. The exosomes are typically between 30 to 150 nanometers (nm) in diameter. In malignancies, such as cancer, the exosomes released by the cancerous cells may include proteins that may be used as target analytes to diagnose cancer.

As shown in the expanded view 142 of FIG. 1A, an exosome 135 may contain a vast array of different proteins depending on the host cell. The components of the exosome is further modulated by the cellular state (e.g., stress, activation, or inhibition of specific pathways). Tetraspanins, such as CD9 156, CD63 157, CD81 158, and CD82 (not shown), which are the most common canonical exosome marker proteins, and/or other type of tetraspanins may be present on the surface of the exosome. There are 34 tetraspanins in mammals, 33 of which have been identified in humans. Tetraspanin 159 shown in the expanded view 142 refers to any of the 34 tetraspanins in mammals, including, but not limited to CD9 156, CD63 157, CD81 158, and CD82.

Other components 138 of an exosome may include different enzymes, lipids, transcription factors, cytoskeletons, etc. If an exosome is released by a malignant tumor or an infected cell, the exosome may also contain proteins 137 that may be used as general markers to identify malignancies. The exosome released by a malignant tumor, or an infected cell, may also contain tumor-specific proteins 194 that may be used to identify specific tumors. The exosome released by an organ may contain organ-specific proteins 196 that may be used to identify the organ.

Multiple tetraspanins of the same type (e.g., multiple CD9 marker proteins 156, multiple CD63 marker proteins 157, multiple CD81 marker proteins 158, multiple CD82 marker proteins, etc.), multiple tetraspanins of the different types, and/or multiple target analyte proteins 137 may be present on a single exosome 135. As described herein, the immunoassays of the present embodiments may use the exosomes to capture and identify the target analytes 137 such as the proteins (or other markers) related to different malignancies.

As shown in the expanded view 143 of FIG. 1A, the conjugate pad 110 may contain one or more different types of binding reagents 176-179 that are capable of binding to different types of tetraspanins 156-159 on the surface of exosomes 135 in the sample fluid 190. The binding reagents may be, for example, and without limitations, different types of tetraspanin antibodies. Although several examples of tetraspanin antibodies, target analyte antibodies, tumor-specific protein antibodies, and organ-specific protein antibodies are used herein, it should be noted that some of the LFA devices of the present embodiments may use binding reagents on the conjugate pads, on the test lines, on/or on the control lines that are not antibodies.

In addition to, or in lieu of, the antibodies 176-178 for the three types of tetraspanins 156-158, the conjugate pad 110 may include antibodies for other types of exosome tetraspanins. The tetraspanin antibody 179 shown in the expanded view 143 refers to the antibody of a tetraspanin, including, but not limited to the CD9 antibody, the CD63 antibody, the CD81 antibody, the CD82 antibody, etc.

The conjugate pad 110 may include antibodies for one or more types of tetraspanins. For example, depending on the type of test performed by the LFA 100, the conjugate pad 110 may include antibodies for one or more of CD9, CD63, CD81, CD82, or other types of tetraspanins. Accordingly, the present embodiments do not necessarily use antibodies for all types of exosome's tetraspanins and may use a single antibody or a combination of any number of the tetraspanins antibodies, depending on the test being performed.

The binding reagent 176-179 may be coupled to a label 180 (also referred to as conjugate, detection conjugate, probe, detector nanoparticle, or tag) which, in its natural state, is readily visible either to the naked eye or with the aid of an optical filter. The label 180 may be made of small particles (e.g., nanoparticles), such as, for example, and without limitations, metallic sols (e.g., colloidal gold or gold sol), dye sols, colored latex particles, carbon, fluorescent particles, europium labels, etc. During the manufacture of the conjugate pad 110, the labeled binding reagent may be coated, impregnated, or otherwise applied or deposited on the conjugate pad 110 and then dried.

After the sample fluid 190 flows from the sample pad 150 into the conjugate pad 110, the sample fluid 190 may solubilize the labeled binding reagent. If the sample fluid contains the exosomes and the exosomes contain at least one of the tetraspanins 159 (e.g., the tetraspanins 156-158 or other tetraspanins, which are not shown) for which the conjugate pad 100 includes an antibody, the exosomes may bind with the labeled binding reagents (e.g., the binding reagents 176-179) and may form an immunocomplex. The labeled binding reagents that do not bind with the exosomes (e.g., when the sample fluid does not include exosomes with tetraspanins for which the conjugate pad includes antibodies or there is excess labeled binding reagent) flow downstream toward the membrane 115 by capillary action. The sample fluid and any other material in the flow path (e.g., unbound labeled binding reagents, wash fluid, etc.) are herein referred to as fluid material.

Depending on the type of test performed by the LFA device, the device may not include separate sample and conjugate pads, and may only include the conjugate pad 110 in some embodiments. Although the sample pad 150 is shown to go over the conjugate pad 110, in some embodiments, the conjugate pad 110 may go over the sample pad 150.

The LFA device 100 may include a membrane 115 and one or more test lines (only one test line 125 is shown for simplicity) that may be embedded in the membrane. The LFA device 100 may optionally include a control line 130 that may be embedded in the membrane 115. The membrane 115 may be made of a material such as, for example, and without limitations, cellulose, nitrocellulose, paper, silica, cotton, glass (e.g., glass fiber), or synthetic material (e.g., polyester, polyethylene, polymers, rayon, nylon, etc.) that allow the fluid material to flow downstream from the conjugate pad 110 into the membrane 115 and from the membrane 115 toward the wicking pad 120 by capillary action. Although the conjugate pad 110 is shown to go over the membrane 115, in some embodiments, the membrane 115 may go over the conjugate pad 110.

The test line 125 may be made of a porous material such as, for example, and without limitations, cellulose, nitrocellulose, paper, silica, cotton, glass (e.g., glass fiber), or synthetic material (e.g., polyester, polyethylene, polymers, rayon, nylon, etc.). The test line 125, in a sandwich assay format, may contain an unlabeled binding reagent that is immobilized on the test line 125 and does not flow downstream when porous material of the test line is moistened (e.g., by the fluid material). As shown in the expanded view 144, the unlabeled binding reagent that is immobilized on the test line 125 is the target analyte's antibody 185.

The LFA device 100 may optionally include a control line 130 that may be embedded in the membrane 115. The control line 130 may be made of a porous material such as, for example, and without limitation, cellulose, nitrocellulose, paper, silica, cotton, glass (e.g., glass fiber), or synthetic material (e.g., polyester, polyethylene, polymers, rayon, nylon, etc.). In a sandwich assay format, the control line 130 may contain an immobilized antibody that binds to the free labeled binding reagents (e.g., the free labeled tetraspanins antibodies 176-179) resulting in a colored control line 130, which confirms that the test has operated correctly regardless of whether or not the target analyte has been present in the sample.

As shown in the expanded view 145, the immobilized antibody on the control line 130 may be an immunocomplex that includes one or more types of exosome's tetraspanins (e.g., CD9 156, C63 157, CD81 158, CD82, etc.). In general, the control line of the LFA devices of the present embodiments may contain an immobilized binding reagent (e.g., an immobilized antibody) against the class of the binding reagents (e.g., antibodies) that are included on the conjugate pad 110. For example, when the antibodies on the conjugate pad are of Immunoglobin G (IgG) class, the control line may include an immobilized anti-IgG antibody. In addition to, or in lieu of the immunocomplex that includes one or more types of exosome's tetraspanins, the control line 130 may include antibodies against the class of the tetraspanins that are included on the conjugate pad 110.

The fluid material that do not bind to the test line 125 or the control line 130 may continue to flow from the membrane 115 into the wicking pad 120 to absorb the fluid material that are not taken up by the test line 125 and the control line 130 while maintaining the capillary flow from the membrane 125 into the wicking pad 120. The wicking pad 120 may be made of a porous material such as, for example, and without limitations, cellulose, nitrocellulose, paper, silica, cotton, glass (e.g., glass fiber), or synthetic material (e.g., polyester, polyethylene, polymers, rayon, nylon, etc.). Depending on the type of test performed by the LFA device, the device may not include a wicking pad 120. Although the wicking pad 120 is shown to go over the membrane 115, in some embodiments, the membrane 115 may go over the wicking pad 120.

FIGS. 1A-1D, as shown, include four stages 101-104. In stage 101 (FIG. 1A), the sample fluid 190 is applied on the sample pad 150. When the sample fluid 190 includes blood, the LFA 100 may have the plasma filter 195 and the sample fluid 190 may be applied to the plasma filter 195. In the embodiments that do not include a sample pad 150, the sample fluid 190 may be applied to the conjugate pad 110 (or applied to a plasma filter located on the conjugate pad when the sample fluid includes blood).

In stage 102 (FIG. 1B), the fluid material may have reached the conjugate pad 110. As shown in the expanded view 146, the tetraspanins (e.g., the tetraspanins 156-159) on the surface of the exosomes 135 in the fluid material may bind with the corresponding tetraspanin antibodies (e.g., the tetraspanin antibodies 176-179). In stage 102, some of the exosomes 135 (e.g., as shown in the expanded view 147) may contain the target analyte 137 on their surface while some of the exosomes 135 (e.g., as shown in the expanded view 148) may not contain the target analyte 137. It should be noted that, depending on the condition of the subject (e.g., a person or an animal) from which the sample fluid 190 (FIG. 1A) is drawn, there may or may not be any exosome with the target analyte 137 in the sample fluid.

The exosomes 135 that are bound with the corresponding tetraspanin antibodies 176-179 may form immunocomplexes. The immunocomplexes and the rest of the fluid material 198 may continue to move, by capillary action, from the conjugate pad 110 to the membrane 115.

In stage 103 (FIG. 1C), the fluid material may have reached the test line 125. As shown in the expanded view 149, the target analyte's antibodies 185 that are immobilized on the test line may bind with the target analyte 137 on the exosomes 135 that have been bound to the tetraspanin antibodies (e.g., the tetraspanin antibodies 176-179) through one of their tetraspanins (e.g., the tetraspanins 156-159). The binding results in a second immunocomplex (the immunocomplex shown in the expanded view 149). The label 180 on the immobilized second immunocomplex colors the test line 125.

The intensity of the colored test line is correlated with the density of the target analyte 137 on the surface of the exosomes 135 in the sample fluid. The second immunocomplex includes the exosomes 135 that are bound (through the target analyte 137 on their surface) with the immobilized target analyte's antibody 185, and (through one of the tetraspanins 156-159 on their surface) with one of the labelled tetraspanins antibodies 176-179. When the sample fluid does not include the target analyte, no immunocomplex binds with the immobilized antibody on the test line 125. As a result, the test line 125 does not change color.

The exosomes that lack the target analyte 137 on their surface may not bind to the immobilized tetraspanin antibodies 176-179 on the test line 125 and may continue to move, with the rest of the fluid material, toward the control line 130 and the wicking pad 120.

In stage 104 (FIG. 1D), the fluid material may have reached the control line 130. As shown in the expanded view 151, the free labeled tetraspanins antibodies (e.g., the 176-179 tetraspanins antibodies) in the fluid material may bind to the immobilized tetraspanins (e.g., the corresponding tetraspanins 156-159). This binding may result in a colored control line, which confirms that the test has operated correctly regardless of whether or not the target analyte has been present in the sample fluid.

Some embodiments of the LFA device may include multiple test lines. In some of these embodiments, some of the test lines may be used to detect exosome proteins that are specific to certain tumors and/or specific to certain organs. An organ-specific protein is defined as a protein whose expression is significantly elevated in one or more specific human organs. The organ-specific proteins may be implicated in human diseases related to the corresponding organs. A tumor-specific protein is defined as a protein whose expression is significantly elevated in one or more specific tumors.

FIG. 2 illustrates examples of the exosome proteins that are specific to certain tumors according to prior art. With reference to FIG. 2, the exosome proteins column 211 of table 200 identifies the name of the exosome proteins. The tumor column 212 identifies the type of tumor(s) that correspond(s) to the exosome proteins of column 211. The body fluid column identifies the body fluid where the exosome proteins have been found.

With reference to FIG. 2, some of the exosome proteins 211, such as Glypican-1 220 may be indicative of a tumor in more than one organ (in this example breast, pancreas, colon, and rectum). Some of the exosome proteins 211, such as PSA 230, may also be an organ-specific protein that may be present in the exosomes released from healthy prostate cells.

FIGS. 3A-3F are functional diagrams illustrating an LFA device 300 and a method that uses one or more antibodies specific to an exosome containing the target analyte as the detection antibodies and includes multiple test lines for capturing a set of one or more organ-specific or tumor-specific proteins and a target analyte, according to various aspects of the present disclosure. The LFA device 300 may be a portable device (e.g., a handheld device or benchtop device) that is used to analyze a sample fluid 190 to determine the presence and/or the amount of one or more analytes, one or more tumor-specific proteins, and/or one or more organ-specific proteins.

With reference to FIGS. 3A-3F, the LFA device 300 may include a test line 125 to detect a target analyte 137. The target analyte 137, in some embodiments, may be a protein that is a general marker that identifies malignancies. The test line 125 of the LFA device 300 may be similar to the test line 125 of the LFA device 100, described above. In addition to the test line 125, the LFA device 300 may include n (where n is an integer greater than or equal to 1) test lines 321-322 to detect organ-specific and/or tumor-specific proteins. The test lines 321-322 may be made of a porous material, as described above, with reference to the test line 125 of the LFA device 100.

Figure 3A:
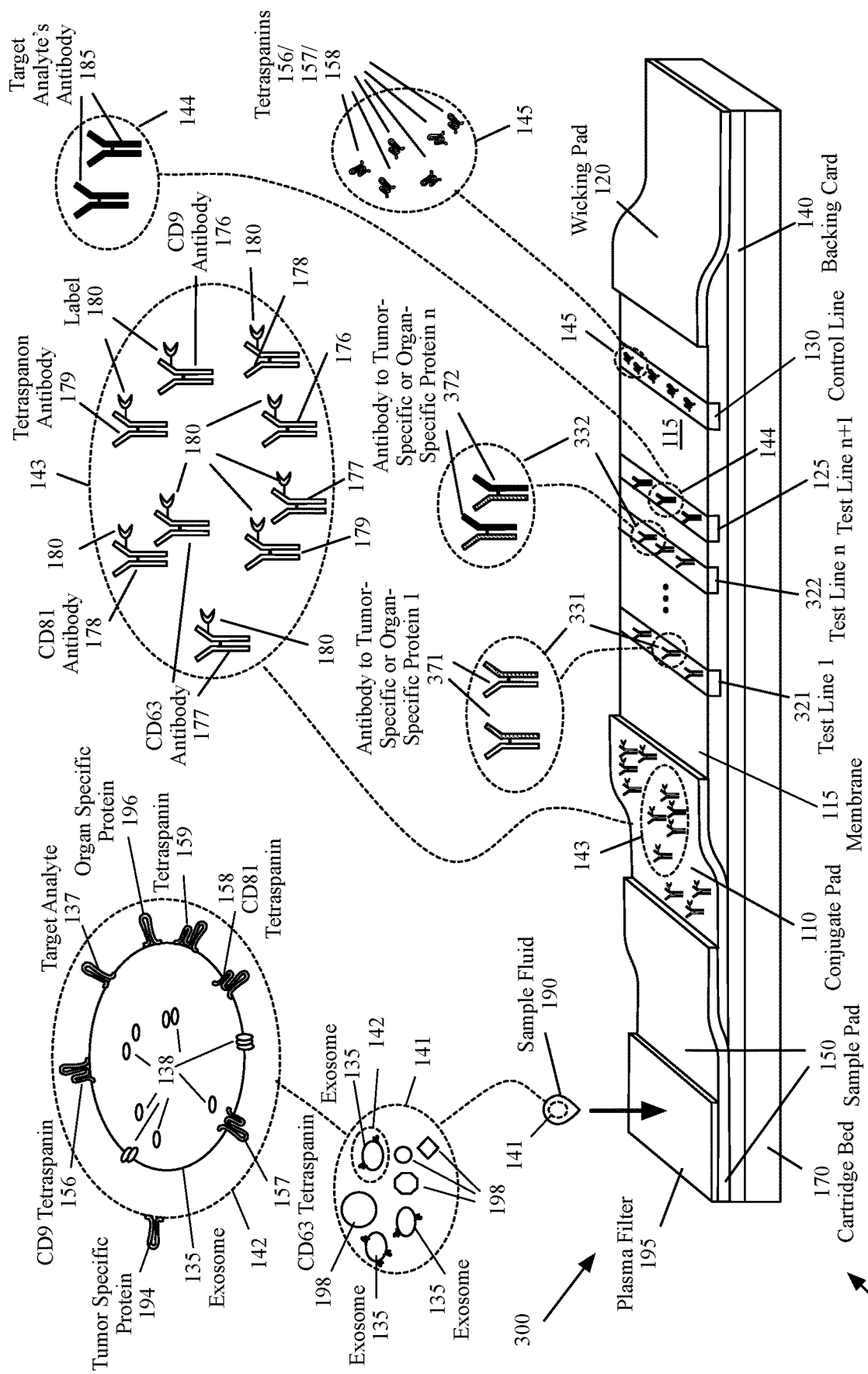
FIGS. 3A-3F are functional diagrams illustrating an LFA device and a method that uses one or more antibodies specific to an exosome containing the target analyte as the detection antibodies and includes multiple test lines for capturing a set of one or more organ-specific or tumor-specific proteins and a target analyte, according to various aspects of the present disclosure.
Figure 3B:
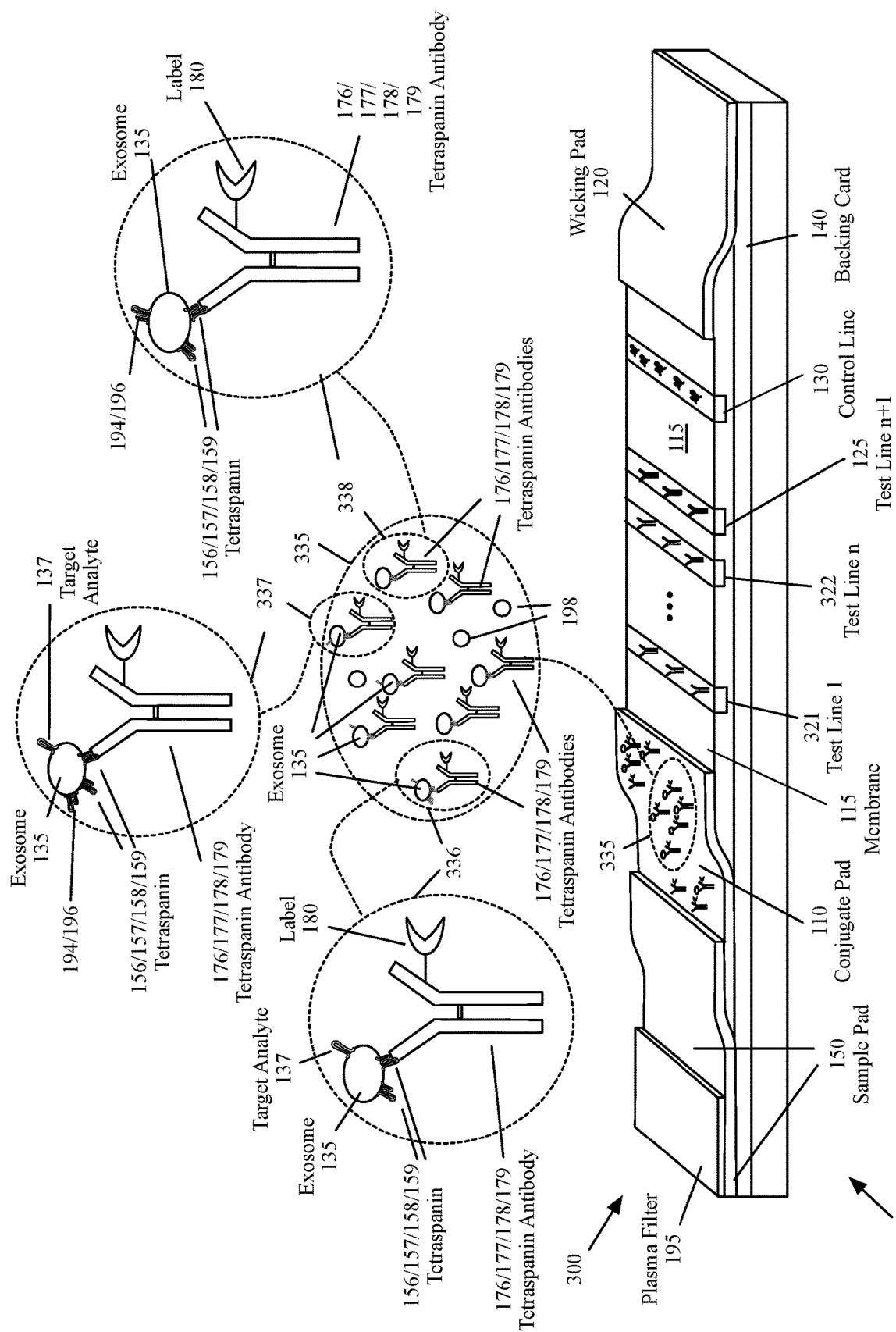
Figure 3C:
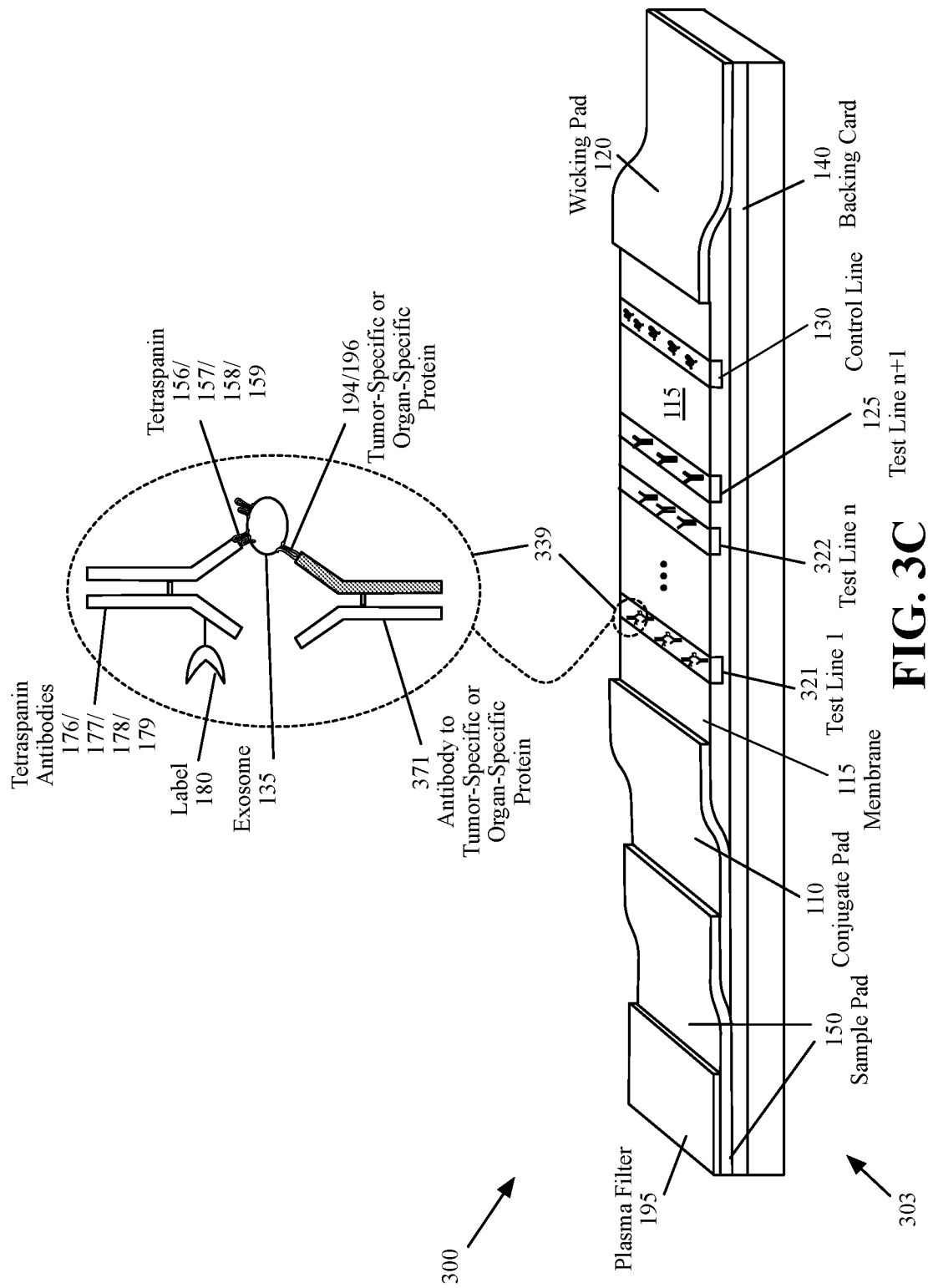
Figure 3D:
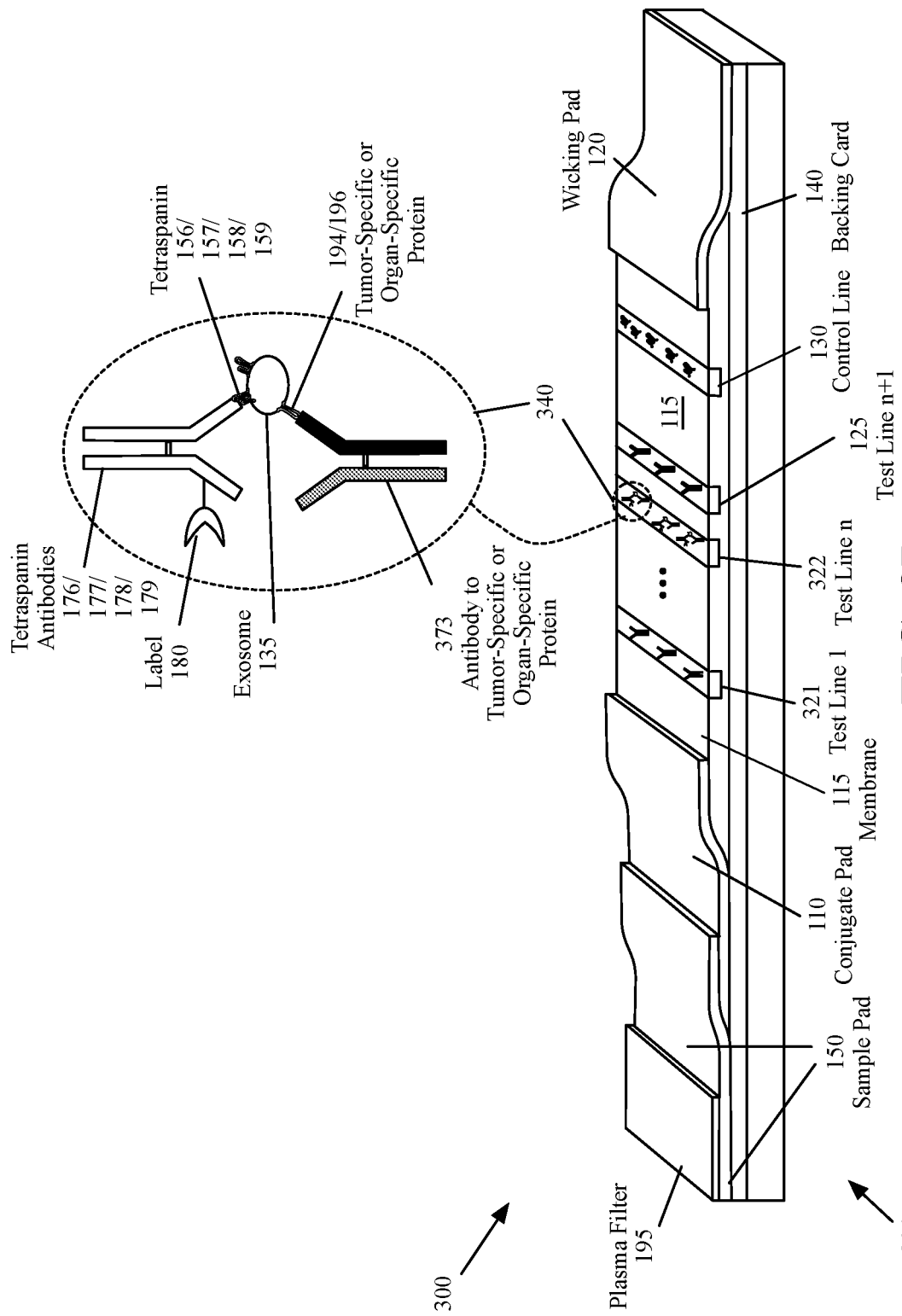
Figure 3E:
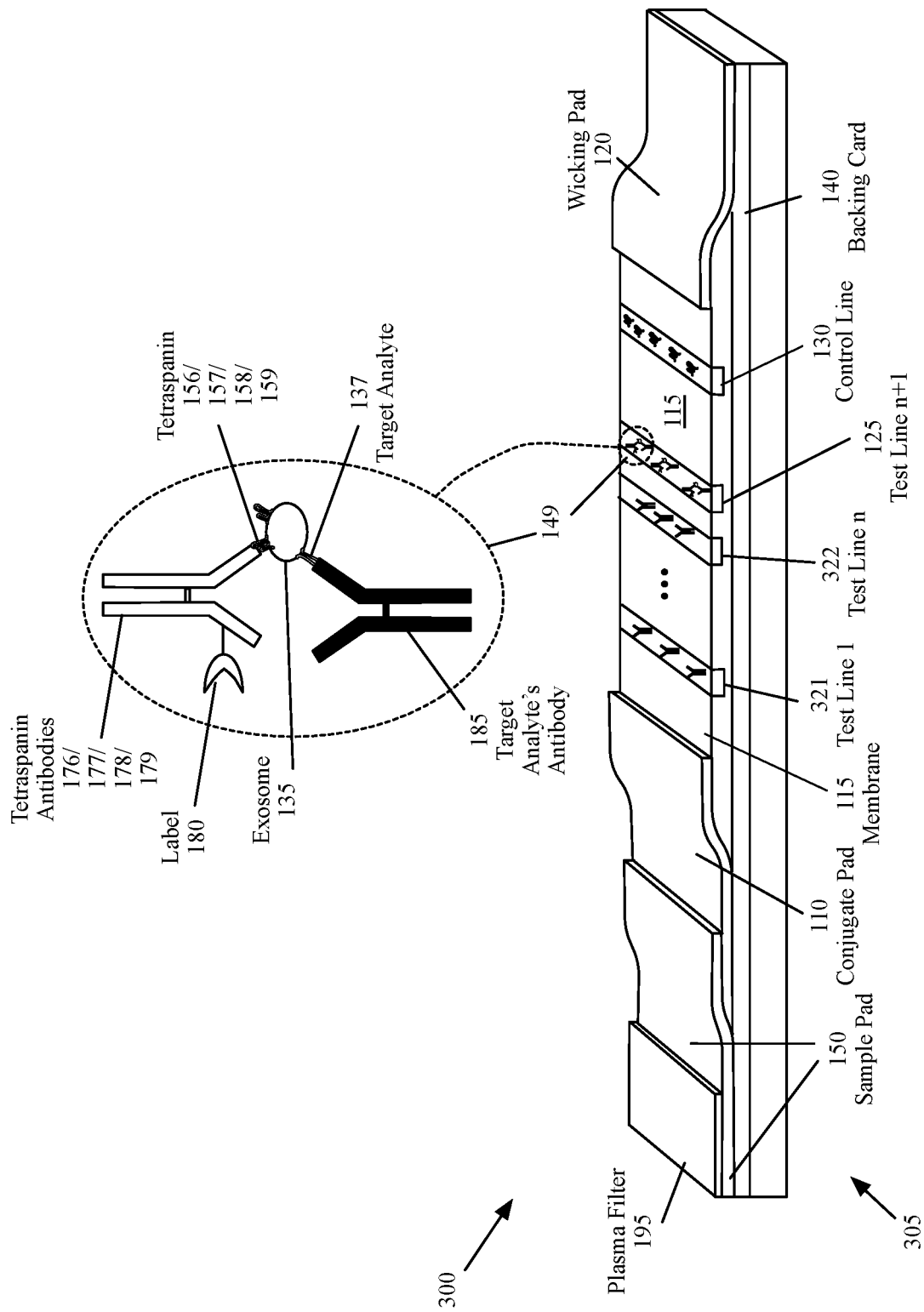
Figure 3F:
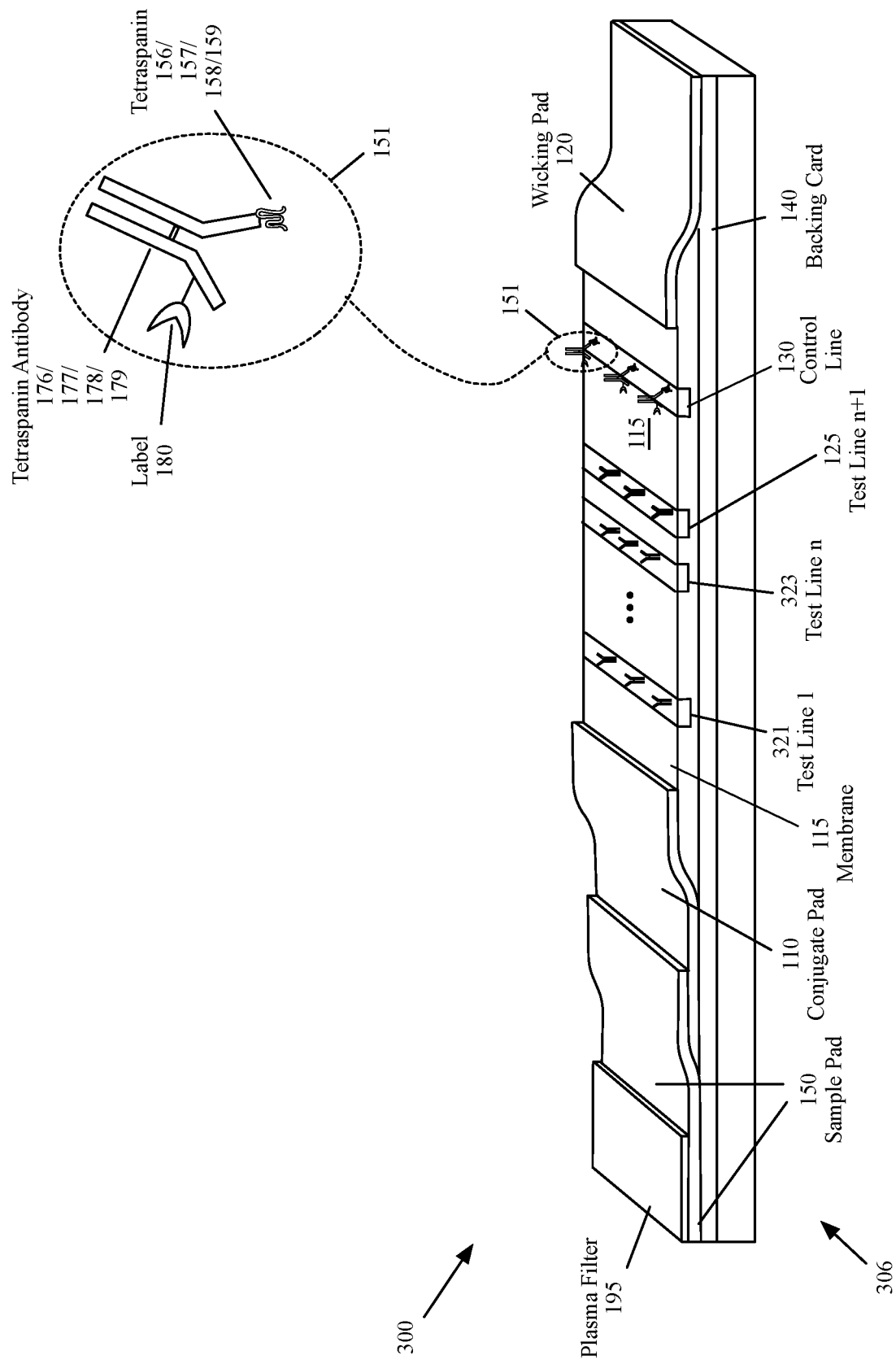

FIGS. 3A-3F, as shown, include six stages 301-307. In stage 301 (FIG. 3A), the sample fluid 190 may be applied to the sample pad 150. When the sample fluid 190 includes blood, the LFA 300 may have the plasma filter 195 and the sample fluid 190 may be applied to the plasma filter 195. In the embodiments that do not include a sample pad 150, the sample fluid 190 may be applied to the conjugate pad 110 (or applied to a plasma filter located on the conjugate pad when the sample fluid includes blood). The expanded views 141-145 of FIG. 3A illustrate similar items as the corresponding expanded views of FIG. 1A.

The unlabeled binding reagent that is immobilized on each test lines 321-322 may be an antibody 371-372 to an organ-specific protein, such as the organ-specific protein 196, or a tumor-specific protein, such as the tumor-specific protein 194. As described above, some proteins may act both as tumor-specific and organ-specific proteins. The LFA device 300 may be configured such that the organ-specific proteins or the tumor-specific proteins that bind to the immobilized antibodies 371-372 are different proteins.

With reference to FIG. 3A, a quantity of an antibody 371 to an organ-specific protein or a tumor-specific protein may be immobilized on the test line 321 (as shown in the expanded view 331), a quantity of an antibody 372 to an organ-specific protein or a tumor-specific protein may be immobilized on the test line 322 (as shown in the expanded view 332), etc. Although two test lines 321-322 are shown for capturing the tumor-specific or organ-specific proteins, different embodiments of the LFA device 300 may include any number of one or more test lines similar to the test lines 321-322 for capturing the tumor-specific or organ-specific proteins. Other components of the LFA device 300 may be similar to the corresponding components of the LFA device 100 described above with reference to FIGS. 1A-1D).

In stage 302 (FIG. 3B), the fluid material may have reached the conjugate pad 110. As shown in the expanded view 335, the tetraspanins (e.g., the tetraspanins 156-159) on the surface of the exosomes 135 in the fluid material may bind with the corresponding tetraspanin antibodies (e.g., the tetraspanin antibodies 176-179). In stage 302, some of the exosomes 135 (e.g., as shown in the expanded views 336 and 337) may contain the target analyte 137 on their surface while some of the exosomes 135 (e.g., as shown in the expanded view 338) may not contain the target analyte 137. Furthermore, some of the exosomes 135 (e.g., as shown in the expanded views 337 and 338) may contain one or more tumor-specific proteins 194 and/or one or more organ-specific proteins 196 on their surface while some of the exosomes 135 (e.g., as shown in the expanded view 336) may not contain any tumor-specific proteins or organ-specific proteins on their surface. It should be noted that, depending on the condition of the subject (e.g., a person or an animal) from which the sample fluid 190 (FIG. 1A) is drawn, the sample fluid may or may not include any exosome with the target analyte 137, a tumor-specific protein 194, or an organ-specific protein 196 on its surface.

In stage 302 (FIG. 3B) the exosomes 135 that are bound with the corresponding tetraspanin antibodies 176-179 may form immunocomplexes. The immunocomplexes and the rest of the fluid material 198 may continue to move, by capillary action, from the conjugate pad 110 to the membrane 115.

In stage 303 (FIG. 3C), the fluid material may have reached the test line 321. As shown in the expanded view 339, the tumor-specific or organ-specific antibodies 371 that are immobilized on the test line 321 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). The binding results in a second immunocomplex (the immunocomplex shown in the expanded view 339). The label 180 on the immobilized second immunocomplex colors the test line 321.

The intensity of the colored test line 321 is correlated with the density of the tumor-specific or organ-specific protein on the surface of the exosomes 135 in the sample fluid that correspond to the immobilized antibody 371. The second immunocomplex includes the exosomes 135 that are bound (through the tumor-specific protein 194 or the organ-specific protein 196 on their surface) with the immobilized antibodies 371, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 371, no immunocomplex binds with the immobilized antibody 371 on the test line 321. As a result, the test line 321 does not change color.

The exosomes that lack the tumor-specific protein 194 or the organ-specific protein 196 that corresponds to the immobilized antibodies 371 on their surface may not bind to the immobilized antibodies 371 on the test line 321 and may continue to move, with the rest of the fluid material, toward the test line 342. It should be noted that some embodiments of the LFA device 300 may only include the test lines 341 and 125. These embodiments may not include stage 304. In these embodiments, the unbound material may move from the list line 321 toward the test line 125, as described below with reference to stage 305.

In stage 304 (FIG. 3D), the fluid material may have reached the test line 322. As shown in the expanded view 340, the tumor-specific or organ-specific antibodies 372 that are immobilized on the test line 322 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). It should be noted that the tumor-specific protein 194 or organ-specific protein 196 that correspond to the antibody 372 that is immobilized on the test line 322 is different than the tumor-specific protein 194 or organ-specific protein 196 that correspond to the antibody 371 that is immobilized on the test line 321. The binding on the test line 342 results in a third immunocomplex (the immunocomplex shown in the expanded view 340). The label 180 on the immobilized third immunocomplex colors the test line 322.

The intensity of the colored test line 322 is correlated with the density of the tumor-specific or organ-specific protein on the surface of the exosomes 135 in the sample fluid that correspond to the immobilized antibody 372. The third immunocomplex includes the exosomes 135 that are bound (through the tumor-specific protein 194 or the organ-specific protein 196 on their surface) with the immobilized antibodies 372, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 372, no immunocomplex binds with the immobilized antibody 372 on the test line 322. As a result, the test line 322 does not change color.

The exosomes that lack the tumor-specific protein 194 or the organ-specific protein 196 that corresponds to the immobilized antibodies 372 on their surface may not bind to the immobilized antibodies 372 on the test line 322 and may continue to move, with the rest of the fluid material, toward the test line 125. It should be noted that some embodiments of the LFA device 300 may include more than two (e.g., three or more) test lines 341-342 to capture tumor-specific and/or organ-specific proteins. These embodiments may include additional stages similar to the 304.

In stage 305 (FIG. 3E), the fluid material may have reached the test line 125. As shown in the expanded view 149, the target analyte's antibodies 185 that are immobilized on the test line may bind with the target analyte 137 on the exosomes 135 that have been bound to the tetraspanin antibodies (e.g., the tetraspanin antibodies 176-179) through one of their tetraspanins (e.g., the tetraspanins 156-159). The binding results in an immunocomplex (the immunocomplex shown in the expanded view 149). The label 180 on the immobilized second immunocomplex colors the test line 125.

The intensity of the colored test line is correlated with the density of the target analyte 137 on the surface of the exosomes 135 in the sample fluid. The immunocomplex in the expanded view 149 includes the exosomes 135 that are bound (through the target analyte 137 on their surface) with the immobilized target analyte's antibody 185, and (through one of the tetraspanins 156-159 on their surface) with one of the labelled tetraspanins antibodies 176-179. When the sample fluid does not include the target analyte, no immunocomplex binds with the immobilized antibody on the test line 125. As a result, the test line 125 does not change color.

The exosomes that lack the target analyte 137 on their surface may not bind to the immobilized tetraspanin antibodies 176-179 on the test line 125 and may continue to move, with the rest of the fluid material, toward the control line 130 and the wicking pad 120.

In stage 306 (FIG. 3F), the fluid material may have reached the control line 130. As shown in the expanded view 151, the free labeled tetraspanins antibodies (e.g., the 176-179 tetraspanins antibodies) in the fluid material may bind to the immobilized tetraspanins (e.g., the corresponding tetraspanins 156-159). This binding may result in a colored control line, which confirms that the test has operated correctly regardless of whether or not the target analyte has been present in the sample fluid. The fluid material that do not bind to the control line 130 may continue to flow from the membrane 115 into the wicking pad 120 to absorb the fluid material that are not taken up by the test line 125 and the control line 130 while maintaining the capillary flow from the membrane 125 into the wicking pad 120.

With reference to FIGS. 3A-3F, the results of a test on the LFA device 300 may be interpreted as follows. When none of the test lines 321-322 and 125 are colored at the end of a test, neither the target analyte 137, nor the tumor-specific proteins, nor the organ-specific proteins whose antibodies where immobilized on the test lines 321-322 were present in the sample fluid 190 in detectable amounts. When the test line 125 is colored at the end of a test but none of the test lines 321-322 are colored, the target analyte 137 (e.g., and without limitation, a general marker of a malignancy such as cancer) is detected in the sample fluid but the malignancy may not be attributed to any specific tumor or specific organ.

When the test line 125 and at least one of the test lines 321-322 are colored at the end of a test, the target analyte 137 (e.g., and without limitation, a general marker of a malignancy such as cancer) is detected in the sample fluid.

In addition, the malignancy may be attributed with a high probability to the specific tumor(s) or the specific organ(s) whose exosome protein(s) 194/196 was/were captured on the colored test line(s) 321-322.

When the test line 125 is not colored but at least, one of the test lines 321-322 is colored at the end of a test, the target analyte 137 attributed to a malignancy is not detected. In this scenario, the test line(s) 321-322 may have been colored either due to the presence of the organ-specific proteins on the surface of exosomes released from a healthy organ or due to the detected exosome proteins being released by a tumor that does not have the general marker (i.e., the target analyte protein).

In the embodiment of FIGS. 3A-3F, multiple test lines 321-322 and 125 were placed on the same test strip that also includes the sample pad 150, the conjugate pad 110, the membrane 115, the control line 130, and the wicking pad 120. Some embodiments may place each of the test lines 321-322 and 125 on a separate test strip where each test strip may include a sample pad 150, a conjugate pad 110, a membrane 115, a control line 130, and a wicking pad 120. The multiple strips may be placed inside the same test cartridge.

FIGS. 4A-4D are functional diagrams illustrating an LFA device 400 and a method that uses one or more antibodies specific to an exosome containing the target analyte as the detection antibodies and includes multiple strips with test lines for capturing a set of one or more organ-specific or tumor-specific proteins and a target analyte, according to various aspects of the present disclosure. The LFA device 400 may be a portable device (e.g., a handheld device or benchtop device) that is used to analyze a sample fluid 190 to determine the presence and/or the amount of one or more analytes, one or more tumor-specific proteins, and/or one or more organ-specific proteins.

With reference to FIGS. 4A-4D, the LFA device 400 may include several test strips 481-483. Each two adjacent test strips may be separated by a gap 470 that may prevent any fluids from flowing from one test strip into the other. For clarity, the gaps 470 are shown proportionally wider that the other components of the LFA device 400.

The multiple test strip LFA device 400 may include a cartridge (only the cartridge's bed 170 is shown for clarity) that encompasses the test strips 481-483. Each of the test strips 481-483 may include a separate sample pad 150, a separate membrane 115, a separate test line 321-322 and 125, a separate control line 130, and a separate wicking pad 120.

The test line 125 may be located on the strip 483 and may be used to detect a target analyte 137. The target analyte 137, in some embodiments, may be a protein that is a general marker that identifies malignancies. The test line 125 of the LFA device 400 may be similar to the test line 125 of the LFA devices 100 and 300, described above.

In addition to the test line 125 located on the test strip 483, the LFA device 400 may include n (where n is an integer greater than or equal to 1) test lines 321-322 located on the corresponding test strips 481-482 to detect organ-specific and/or tumor-specific proteins. The test lines 321-322 may be made of a porous material, as described above, with reference to the test line 125 of the LFA devices 100 and 300.

Figure 4A:
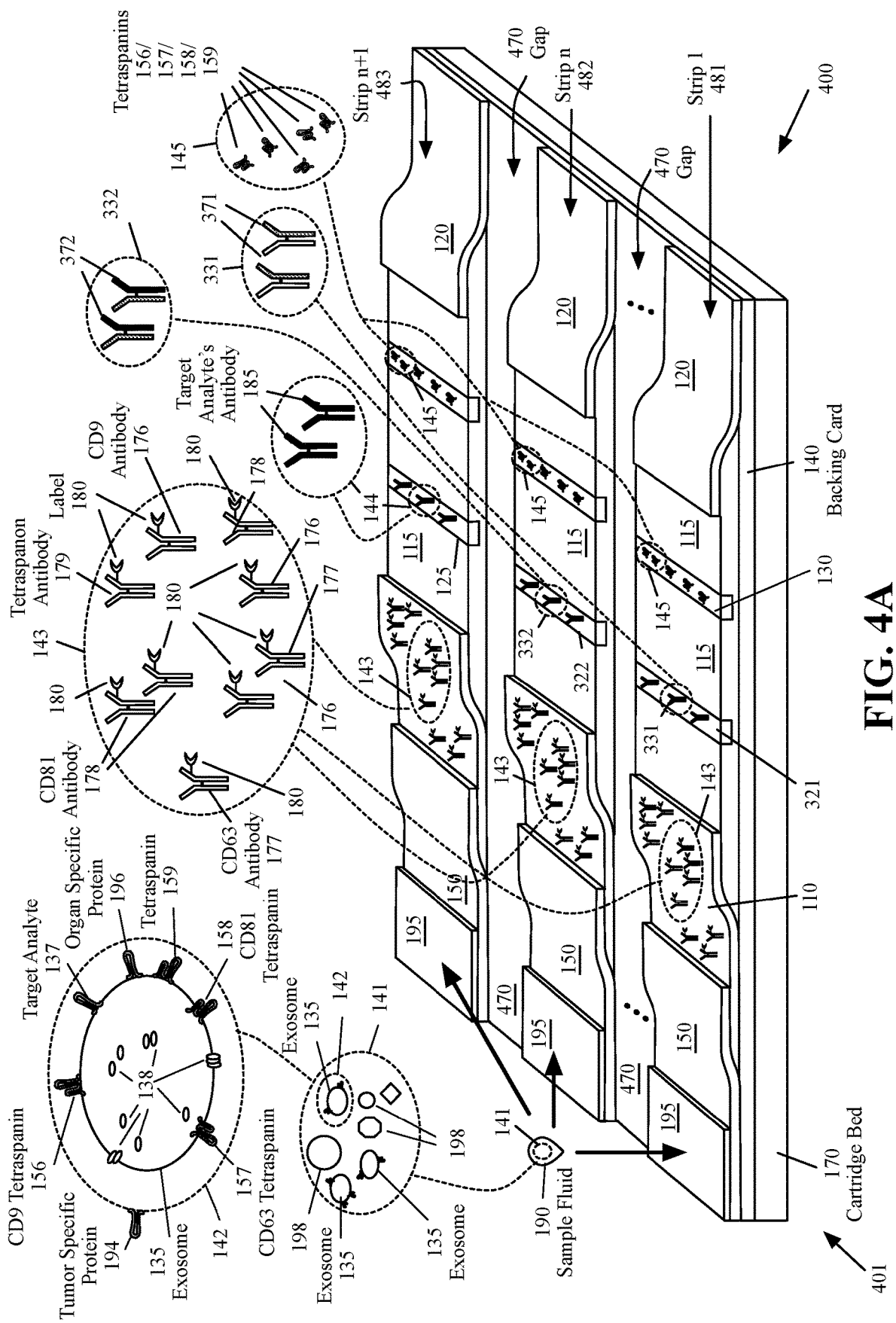
FIGS. 4A-4D are functional diagrams illustrating an LFA device and a method that that uses one or more antibodies specific to an exosome containing the target analyte as the detection antibodies and includes multiple strips with test lines for capturing a set of one or more organ-specific or tumor-specific proteins and a target analyte, according to various aspects of the present disclosure.
Figure 4B:
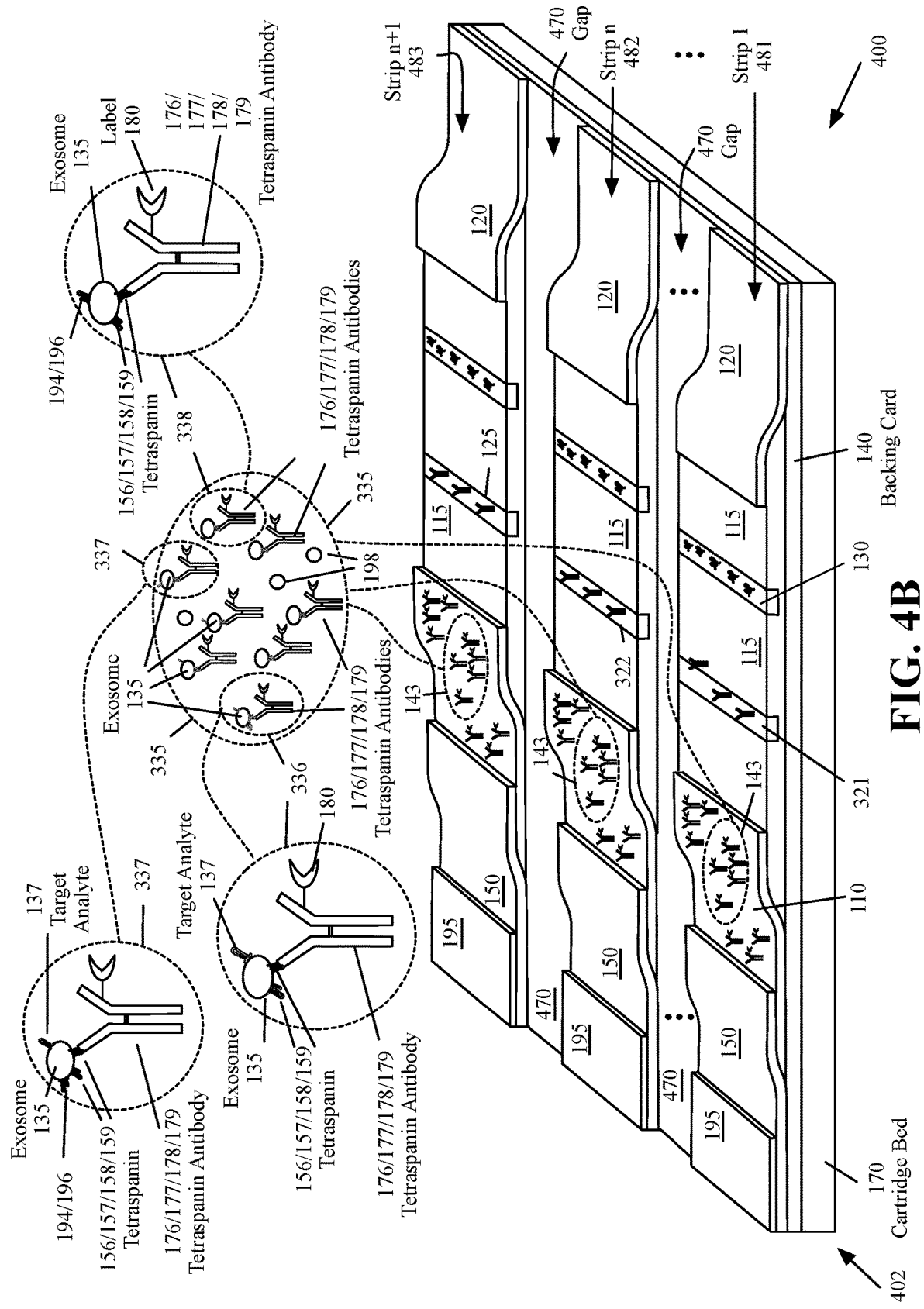
Figure 4C:
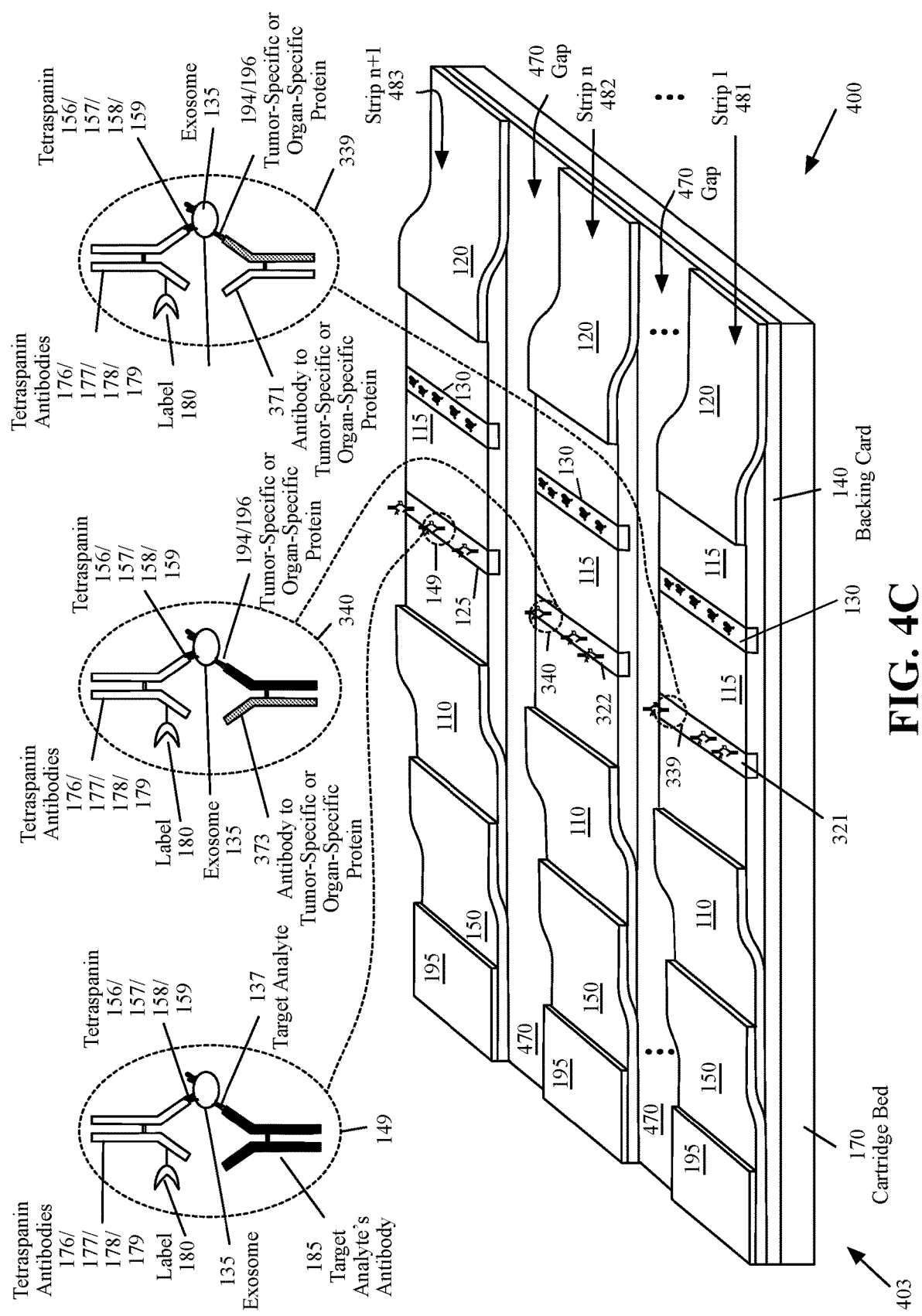
Figure 4D:
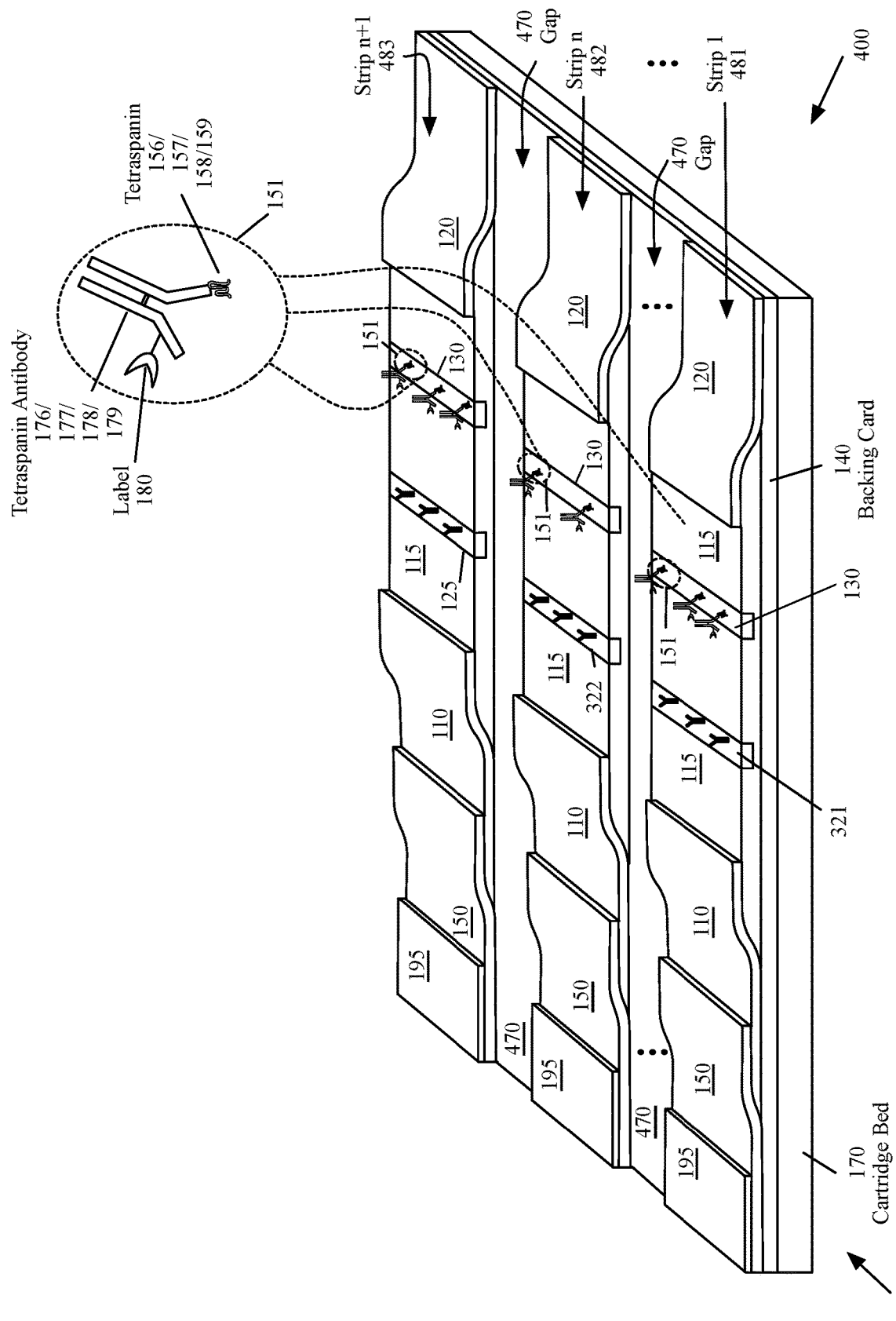

FIGS. 4A-4D, as shown, include four stages 401-404. In stage 401 (FIG. 4A), the sample fluid 190 may be applied to the sample pads 150 of each test strip 481-483. When the sample fluid 190 includes blood, the LFA 400 may have the plasma filters 195 on each test strip 481-483 and the sample fluid 190 may be applied to the plasma filters 195. In the embodiments that do not include a sample pad 150, the sample fluid 190 may be applied to the conjugate pads 110 (or applied to plasma filters located on the conjugate pads when the sample fluid includes blood). The expanded views 141-145 of FIG. 4A illustrate similar items as the corresponding expanded views of FIGS. 1A and 3A.

The unlabeled binding reagent that is immobilized on each test line 321-322 may be an antibody 371-372 to an organ-specific protein, such as the organ-specific protein 196, or a tumor-specific protein, such as the tumor-specific protein 194. As described above, some proteins may act both as tumor-specific and organ-specific proteins. The LFA device 400 may be configured such that the organ-specific proteins or the tumor-specific proteins that bind to the immobilized antibodies 371-372 are different proteins.

With reference to FIG. 4A, a quantity of an antibody 371 to an organ-specific protein or a tumor-specific protein may be immobilized on the test line 321 located on the test strip 481 (as shown in the expanded view 331), a quantity of an antibody 372 to an organ-specific protein or a tumor-specific protein may be immobilized on the test line 322 located on the test strip 482 (as shown in the expanded view 332), etc. Although two test strips 481-482 and the corresponding test lines 321-322 are shown for capturing the tumor-specific or organ-specific proteins, different embodiments of the LFA device 400 may include any number of one or more test strips and the corresponding test lines similar to the test strips 481-482 and the test lines 321-322 for capturing the tumor-specific or organ-specific proteins. Other components of the LFA device 400 may be similar to the corresponding components of the LFA devices 100 and 300 described above with reference to FIGS. 1A-1D and FIGS. 3A-3F).

In stage 402 (FIG. 4B), the fluid material may have reached the conjugate pads 110 of the test strips 481-483. As shown in the expanded view 335, the tetraspanins (e.g., the tetraspanins 156-159) on the surface of the exosomes 135 in the fluid material may bind with the corresponding tetraspanin antibodies (e.g., the tetraspanin antibodies 176-179).

In stage 402, some of the exosomes 135 (e.g., as shown in the expanded views 336 and 337) may contain the target analyte 137 on their surface while some of the exosomes 135 (e.g., as shown in the expanded view 338) may not contain the target analyte 137. Furthermore, some of the exosomes 135 (e.g., as shown in the expanded views 337 and 338) may contain one or more tumor-specific proteins 194 and/or one or more organ-specific proteins 196 on their surface while some of the exosomes 135 (e.g., as shown in the expanded view 336) may not contain any tumor-specific proteins or organ-specific proteins on their surface. It should be noted that, depending on the condition of the subject (e.g., a person or an animal) from which the sample fluid 190 (FIG. 1A) is drawn, the sample fluid may or may not include any exosome with the target analyte 137, a tumor-specific protein 194, or an organ-specific protein 196 on its surface.

In stage 402 (FIG. 4B) the exosomes 135 that are bound with the corresponding tetraspanin antibodies 176-179 may form immunocomplexes. The immunocomplexes and the rest of the fluid material 198 may continue to move, by capillary action, from the conjugate pad 110 of each test strip to the membrane 115 of the test strip.

In stage 403 (FIG. 4C), the fluid material may have reached the test lines 321-322 and 125. As shown in the expanded view 339, the tumor-specific or organ-specific antibodies 371 that are immobilized on the test line 321 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). The binding results in an immunocomplex (the immunocomplex shown in the expanded view 339). The label 180 on the immobilized immunocomplex colors the test line 321.

The intensity of the colored test line 321 is correlated with the density of the tumor-specific or organ-specific protein on the surface of the exosomes 135 in the sample fluid that correspond to the immobilized antibody 371. The immunocomplex shown in the expanded view 339 includes the exosomes 135 that are bound (through the tumor-specific protein 194 or the organ-specific protein 196 on their surface) with the immobilized antibodies 371, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 371, no immunocomplex binds with the immobilized antibody 371 on the test line 321. As a result, the test line 321 does not change color.

As shown in the expanded view 340, the tumor-specific or organ-specific antibodies 372 that are immobilized on the test line 322 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). It should be noted that the tumor-specific protein 194 or organ-specific protein 196 that correspond to the antibody 372 that is immobilized on the test line 322 is different than the tumor-specific protein 194 or organ-specific protein 196 that correspond to the antibody 371 that is immobilized on the test line 321. The binding on the test line 342 results in an immunocomplex (the immunocomplex shown in the expanded view 340). The label 180 on the immobilized immunocomplex colors the test line 322.

The intensity of the colored test line 322 is correlated with the density of the tumor-specific or organ-specific protein on the surface of the exosomes 135 in the sample fluid that correspond to the immobilized antibody 372. The immunocomplex shown in the expanded view 340 includes the exosomes 135 that are bound (through the tumor-specific protein 194 or the organ-specific protein 196 on their surface) with the immobilized antibodies 372, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 372, no immunocomplex binds with the immobilized antibody 372 on the test line 322. As a result, the test line 322 does not change color.

As shown in the expanded view 149, the target analyte's antibodies 185 that are immobilized on the test line may bind with the target analyte 137 on the exosomes 135 that have been bound to the tetraspanin antibodies (e.g., the tetraspanin antibodies 176-179) through one of their tetraspanins (e.g., the tetraspanins 156-159). The binding results in an immunocomplex (the immunocomplex shown in the expanded view 149). The label 180 on the immobilized second immunocomplex colors the test line 125.

The intensity of the colored test line 125 is correlated with the density of the target analyte 137 on the surface of the exosomes 135 in the sample fluid. The immunocomplex shown in the expanded view 149 includes the exosomes 135 that are bound (through the target analyte 137 on their surface) with the immobilized target analyte's antibody 185, and (through one of the tetraspanins 156-159 on their surface) with one of the labelled tetraspanins antibodies 176-179. When the sample fluid does not include the target analyte 137, no immunocomplex binds with the immobilized antibody on the test line 125. As a result, the test line 125 does not change color.

The exosomes that lack the tumor-specific protein 194 or the organ-specific protein 196 that corresponds to the immobilized antibodies 371 on their surface may not bind to the immobilized antibodies 371 on the test line 321 and may continue to move, with the rest of the fluid material, toward the control line 130 on the test strip 481.

The exosomes that lack the tumor-specific protein 194 or the organ-specific protein 196 that corresponds to the immobilized antibodies 372 on their surface may not bind to the immobilized antibodies 372 on the test line 322 and may continue to move, with the rest of the fluid material, toward the control line 130 on the test strip 482. It should be noted that some embodiments of the LFA device 400 may include more than two test lines 341-342 to capture tumor-specific and/or organ-specific proteins. These embodiments may include additional test strips similar to the test strips 481-482. Some embodiments of the LFA device 400 may include one test line 341 to capture tumor-specific and/or organ-specific proteins. These embodiments may not include the test strip 482.

In stage 404 (FIG. 4D), the fluid material may have reached the control lines 130 of the test strips 481-483. As shown in the expanded view 151, the free labeled tetraspanins antibodies (e.g., the 176-179 tetraspanins antibodies) in the fluid material may bind to the immobilized tetraspanins (e.g., the corresponding tetraspanins 156-159). This binding may result in a colored control lines 130, which confirms that the test has operated correctly regardless of whether or not the target analyte has been present in the sample fluid. The fluid material that do not bind to the control lines 130 may continue to flow from the membranes 115 of the test strips 481-483 into the wicking pads 120 of the test strips 481-483 to absorb the fluid material that are not taken up by the test line 125 and the control line 130 while maintaining the capillary flow from the membrane 125 into the wicking pad 120.

With reference to FIGS. 4A-4D, the results of a test on the LFA device 400 may be interpreted as follows. When none of the test lines 321-322 and 125 are colored at the end of a test, neither the target analyte 137, nor the tumor-specific proteins, nor the organ-specific proteins whose antibodies where immobilized on the test lines 321-322 were present in the sample fluid 190 in detectable amounts. When the test line 125 is colored at the end of a test but none of the test lines 321-322 are colored, the target analyte 137 (e.g., and without limitation, a general marker of a malignancy such as cancer) is detected in the sample fluid but the malignancy may not be attributed to any specific tumor or specific organ.

When the test line 125 and at least one of the test lines are colored 321-322 at the end of a test, the target analyte 137 (e.g., and without limitation, a general marker of a malignancy such as cancer) is detected in the sample fluid. In addition, the malignancy may be attributed with a high probability to the specific tumor(s) or the specific organ(s) whose exosome protein(s) 194/196 was/were captured on the colored test line(s) 321-322.

When the test line 125 is not colored but at least one of the test lines are colored 321-322 at the end of a test, the target analyte 137 attributed to a malignancy is not detected. In this scenario, the test line(s) 321-322 may have been colored either due to the presence of the organ-specific proteins on the surface of exosomes released from a healthy organ or due to the detected exosome proteins being released by a tumor that does not have the general marker (i.e., the target analyte protein).

In the embodiments of FIGS. 1A-1D, the conjugate pad 110 contains the labelled antibodies (e.g., the labelled antibodies 176-179) that act as detection antibodies and test line 130 contains the immobilized target analyte's antibody 185 that acts as the capture antibody. In other embodiments, such as the embodiments described below with reference to FIGS. 5A-5D, the roles of the capture and detection antibodies may be switched.

FIGS. 5A-5D are functional diagrams illustrating an LFA device 500 and a method that uses an antibody specific to the target analyte as the detection antibody and one or more antibodies specific to an exosome containing the target analyte as capture antibodies, according to various aspects of the present disclosure. The LFA device 500 may be a portable device (e.g., a handheld device or benchtop device) that is used to analyze a sample fluid 190 to determine the presence and/or the amount of one or more target analytes.

The LFA device 500 of FIGS. 5A-5D may include similar components and configuration as the LFA device 100 of FIGS. 1A-1D, except that the conjugate pad 110, the test line 125, and the control line 130 of the LFA device 500 contains different antibodies than the LFA device 100.

Figure 5A:
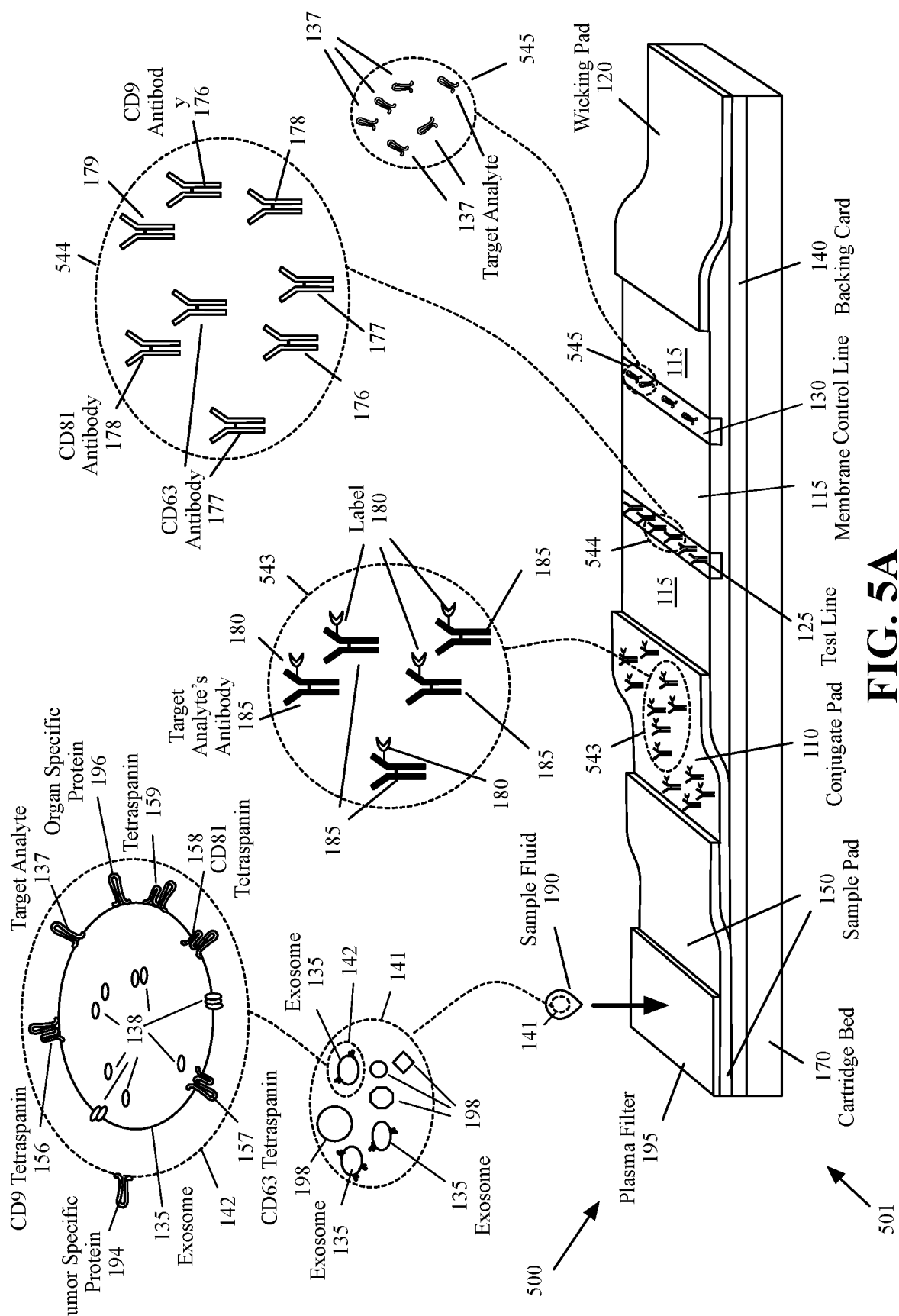
FIGS. 5A-5D are functional diagrams illustrating an LFA device and a method that that uses an antibody specific to the target analyte as the detection antibody and one or more antibodies specific to an exosome containing the target analyte as capture antibodies, according to various aspects of the present disclosure.
Figure 5B:
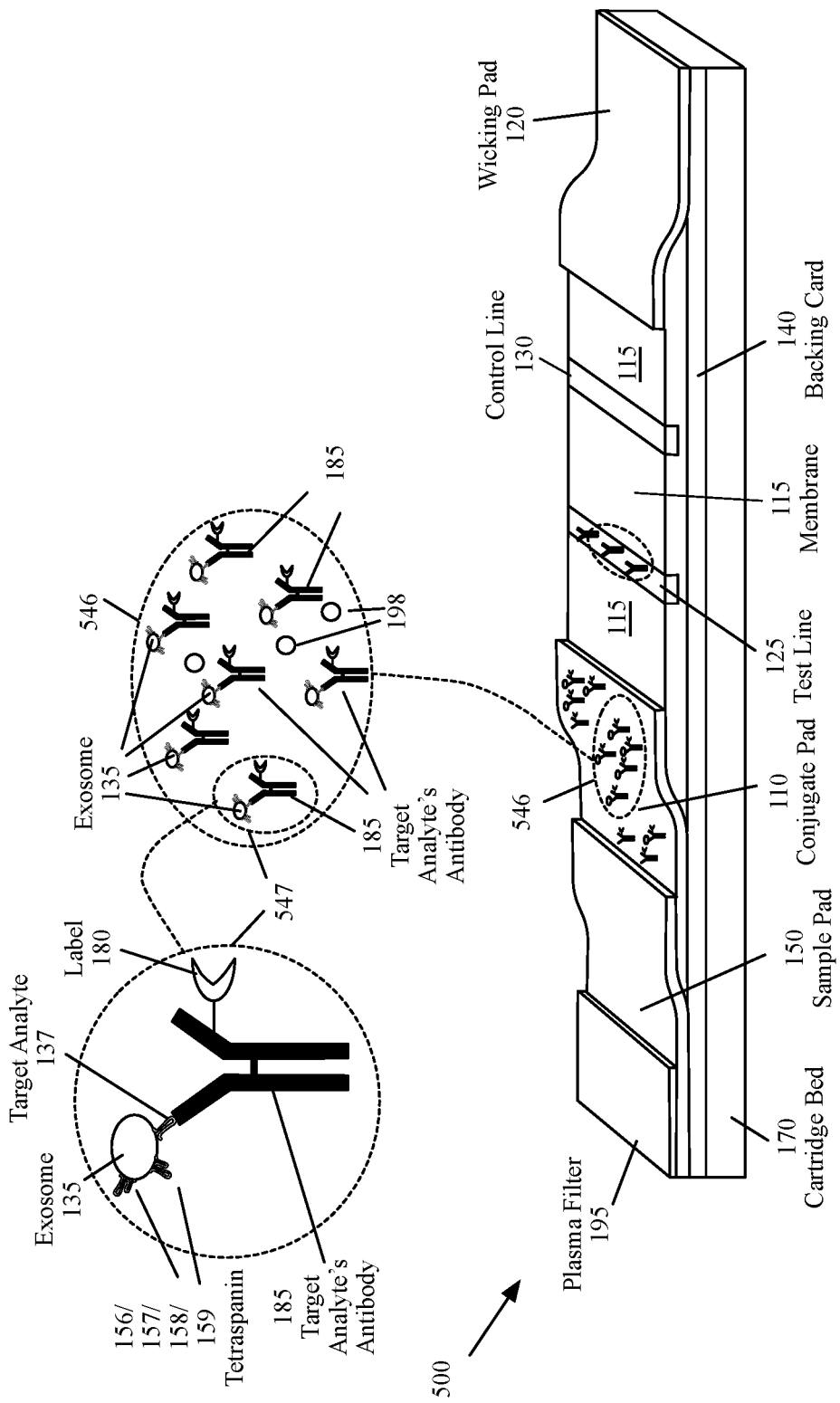
Figure 5C:
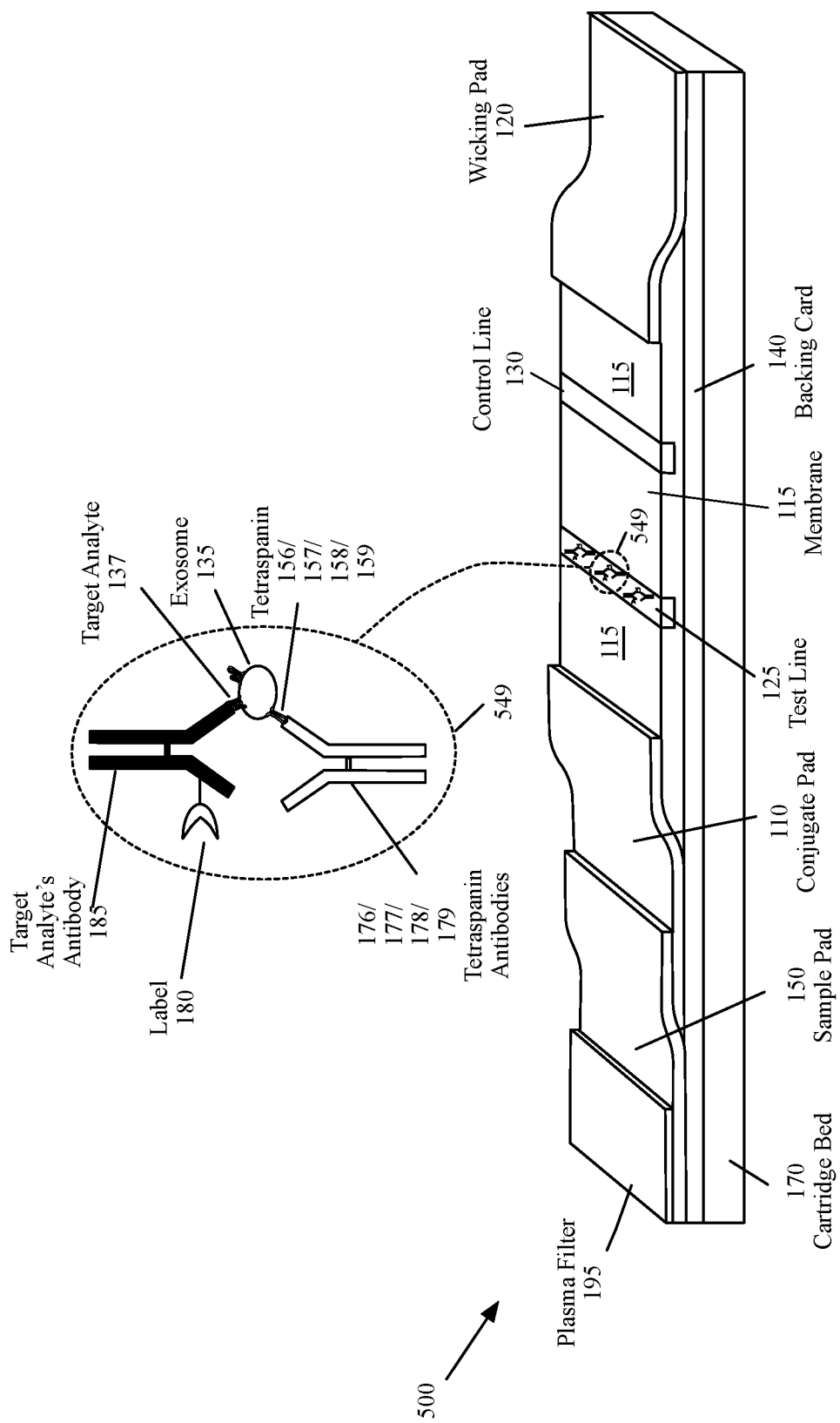
Figure 5D:
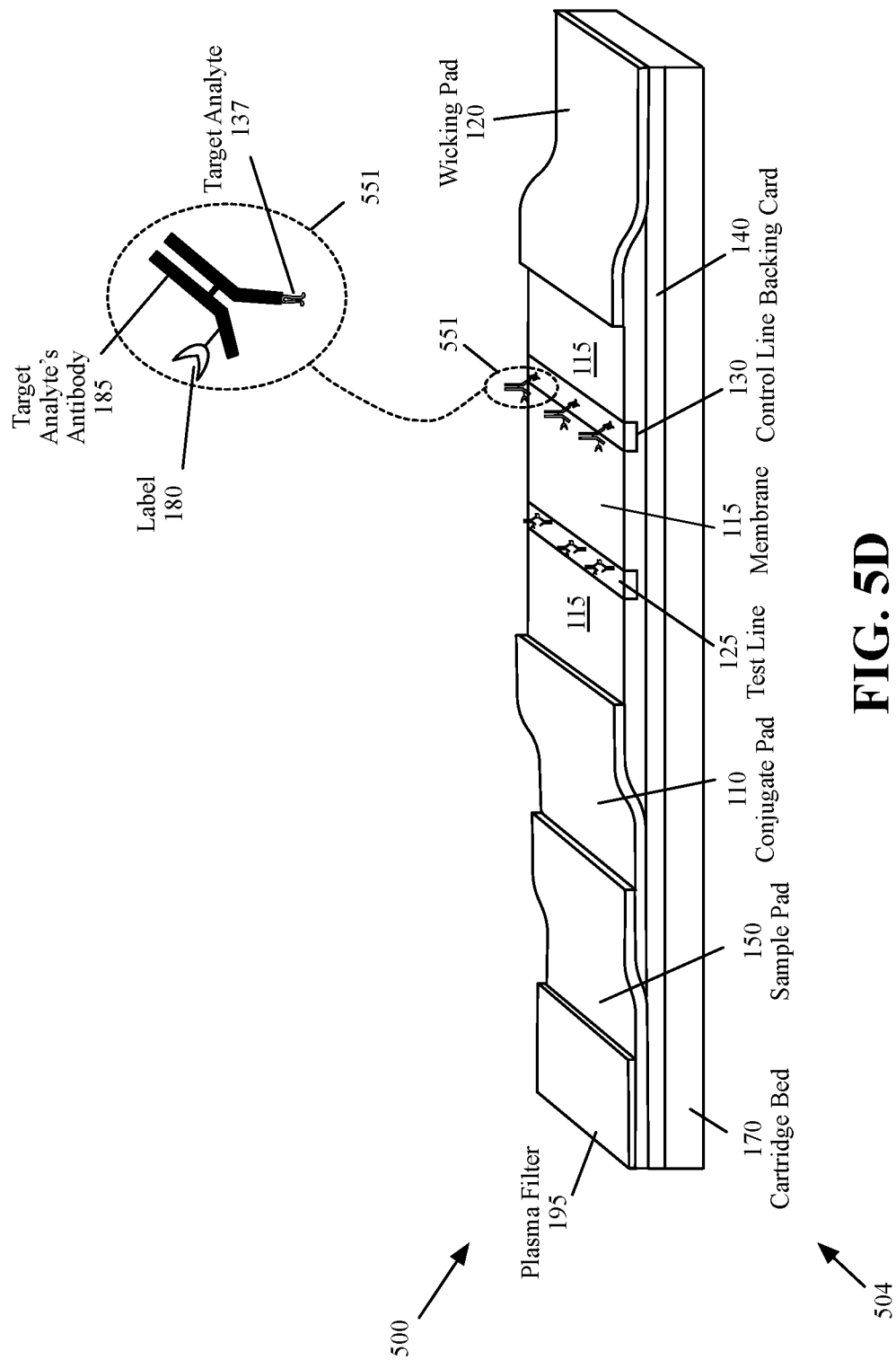

With reference to FIG. 5A, the sample fluid 190 may be similar to the sample fluid 190, the exosome 135 may be similar to the exosome 135, and the target analyte may be similar to the target analyte 137 described above with reference to FIGS. 1A-1D. As shown in the expanded view 543 of FIG. 5A, the conjugate pad 110 may contain the target analyte's antibody 185 as the binding reagent. The target analyte's antibody 185 may be coupled to a label 180 which, in its natural state, is readily visible either to the naked eye or with the aid of an optical filter. The label 180 may be made of small particles (e.g., nanoparticles), such as, without limitations, metallic sols (e.g., colloidal gold or gold sol), dye sols, colored latex particles, carbon, fluorescent particles, europium labels, etc. During the manufacture of the conjugate pad 110, the labeled binding reagent may be coated, impregnated, or otherwise applied or deposited on the conjugate pad 110 and then dried.

After the sample fluid 190 flows from the sample pad 150 into the conjugate pad 110, the sample fluid 190 may solubilize the labeled target analyte's antibody 185. If the sample fluid contains the exosomes 135 and the exosomes 135 contain the target analyte 137 as shown in the expanded view 142 of FIG. 5A, the target analytes 137 may bind to the labeled target analyte's antibody 185.

As shown in the expanded view 544, the test line 125 may contain the immobilized antibodies (e.g., the antibodies 176-179, etc.) for one or more corresponding tetraspanins (e.g., the CD9 tetraspanin 0156, the CD63 tetraspanin 157, the CD81 tetraspanin 158, etc.). The test line may include immobilized antibodies for other types of tetraspanins, which are not shown for clarity. Tetraspanin 159 shown in the expanded view 142 refers to any of the 34 tetraspanins in mammals, including, but not limited to CD9 156, CD63 157, CD81 158, and CD82. The tetraspanin antibody 179 shown in the expanded view 143 refers to the antibody of a tetraspanin, including, but not limited to the CD9 antibody, the CD63 antibody, the CD81 antibody, the CD82 antibody, etc.

As shown in the expanded view 545, the control line may contain the immobilized target analyte 137 in order to bind to the free labelled target analyte antibodies. In general, the control line of the LFA devices of the present embodiments may contain an immobilized antibody against the class of the antibodies that are included on the conjugate pad 110. For example, when the antibodies to the target analyte is of IgG class, the control line 130 of may include an immobilized anti-IgG antibody. In the example of the LFA device 500, in addition to, or in lieu of the immobilized target analyte, the control line 130 of the LFA device 500 may include antibodies against the IgG class of antibodies.

FIGS. 5A-5D, as shown, include four stages 501-504. In stage 501 (FIG. 2A), the sample fluid 190 is applied on the sample pad 150. When the sample fluid 190 includes blood, the LFA 500 may have the plasma filter 195 and the sample fluid 190 may be applied to the plasma filter 195. In the embodiments that do not include a sample pad 150, the sample fluid 190 may be applied to the conjugate pad 110 (or applied to a plasma filter located on the conjugate pad when the sample fluid includes blood).

In stage 502 (FIG. 5B), the fluid material may have reached the conjugate pad 110. As shown in the expanded views 546 and 547, the target analyte 137 on the surface of the exosomes 135 in the fluid material may bind with the target analyte antibody 185. It should be noted that, depending on the condition of the subject (e.g., a person or an animal) from which the sample fluid 190 (FIG. 5A) is drawn, there may or may not be any exosome with the target analyte 137 in the sample fluid.

The exosomes 135 with the target analyte 137 on their surface that are bound with the target analyte antibody 185 may form immunocomplexes. The immunocomplexes and the rest of the fluid material 198 may continue to move, by capillary action, from the conjugate pad 110 to the membrane 115.

In stage 503 (FIG. 5C), the fluid material may have reached the test line 125. As shown in the expanded view 549, the tetraspanin antibodies (e.g., the tetraspanin antibodies 176-179) that are immobilized on the test line 125 may bind with the tetraspanins 156-159 on the exosomes 135 that have been bound to the target analyte's antibodies 185.

The binding results in a second immunocomplex (the immunocomplex shown in the expanded view 549). The label 180 on the immobilized second immunocomplex colors the test line 125. Since the tetraspanins' antibodies 176-179 are immobilized on the test line 125, the exosomes that do not have the target analyte 137, and are not bound to a labelled target analyte's antibody, may also bind with the tetraspanins' antibodies 176-179 and become immobilized on the test line 125. The test line may, therefore, immobilize some particles that do not have a label. These unlabeled particles bind to, and consume, some of the immobilized tetraspanin antibodies 176-179 on the test line 125.

Accordingly, the test line 125 of the LFA device 500 of the present embodiment is designed such that enough tetraspanin antibodies 176-179 are immobilized on the test line 125 to allow for a percentage of the immobilized tetraspanin antibodies 176-179 to be consumed by the exosomes that do not carry a label and the test line still changes color when the sample fluid includes the target analyte. The amount of the immobilized tetraspanin antibodies 176-179 on the test line, in some embodiments, may be determined by a series of experimental tests to ensure the test line changes color when the target analyte is present in the sample fluid. The labeled target analyte's antibodies 185 that do not bind to the target analyte 137 may continue to move, with the rest of the fluid material, toward the control line 130 and the wicking pad 120.

In stage 504 (FIG. 5D), the fluid material may have reached the control line 130. As shown in the expanded view 551, the free labeled target analyte's antibodies 185 in the fluid material may bind to the immobilized target analyte 137 on the control line 130. This binding may result in a colored control line 130, which confirms that the test has operated correctly regardless of whether or not the target analyte has been present in the sample fluid.

As described above, some embodiments of the LFA device may include multiple test lines. In some of these embodiments, some of the test lines may be used to detect exosome proteins that are specific to certain tumors and/or specific to certain organs. FIGS. 6A-6F are functional diagrams illustrating an LFA device 600 and a method that uses an antibody specific to the target analyte as the detection antibody and includes multiple test lines for capturing a set of one or more organ-specific or tumor-specific proteins and a target analyte, according to various aspects of the present disclosure. The LFA device 600 may be a portable device (e.g., a handheld device or benchtop device) that is used to analyze a sample fluid 190 to determine the presence and/or the amount of one or more analytes, one or more tumor-specific proteins, and/or one or more organ-specific proteins.

With reference to FIGS. 6A-6F, the LFA device 600 may include a test line 125 to detect a target analyte 137. The target analyte 137, in some embodiments, may be a protein that is a general marker that identifies malignancies. The test line 125 of the LFA device 600 may be similar to the test line 125 of the LFA devices 100, 300, and 500, described above. In addition to the test line 125, the LFA device 600 may include n (where n is an integer greater than or equal to 1) test lines 321-322 to detect organ-specific and/or tumor-specific proteins. The test lines 321-322 of the LFA device 600 may be similar to the test lines 321-322 of LFA device 300 of FIGS. 3A-3F.

Figure 6A:
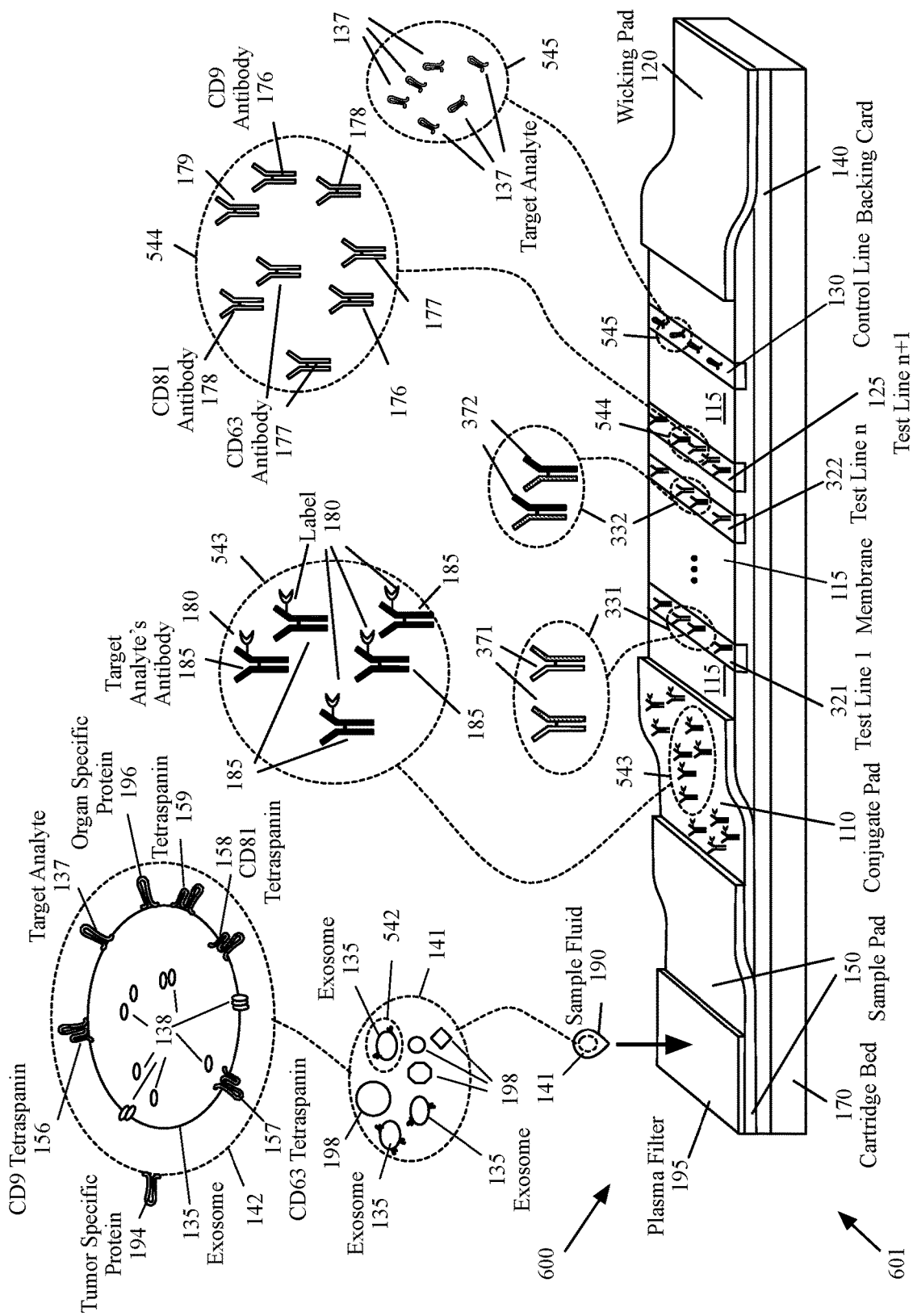
FIGS. 6A-6F are functional diagrams illustrating an LFA device and a method that that uses an antibody specific to the target analyte as the detection antibody and includes multiple test lines for capturing a set of one or more organ-specific or tumor-specific proteins and a target analyte, according to various aspects of the present disclosure.
Figure 6B:
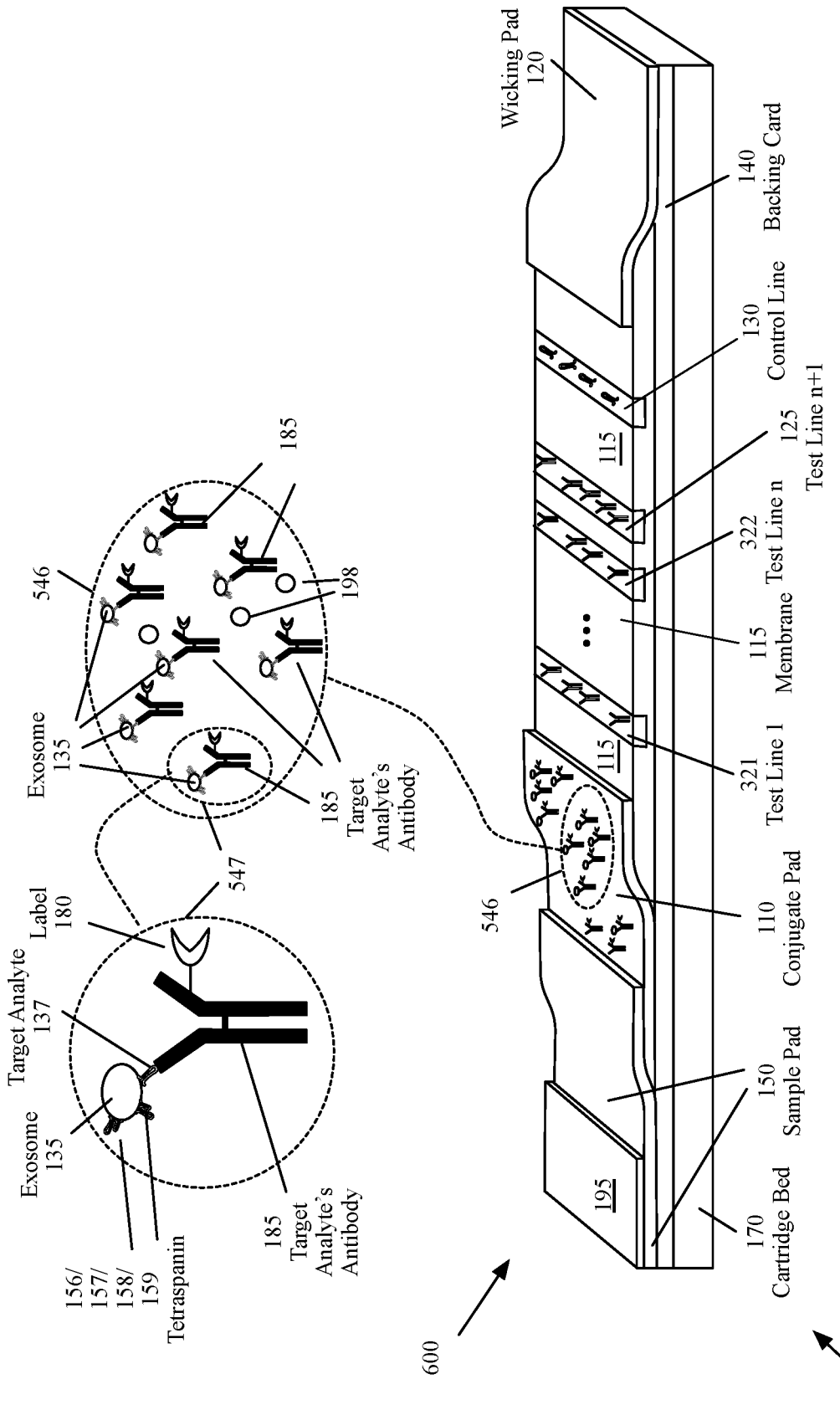
Figure 6C:
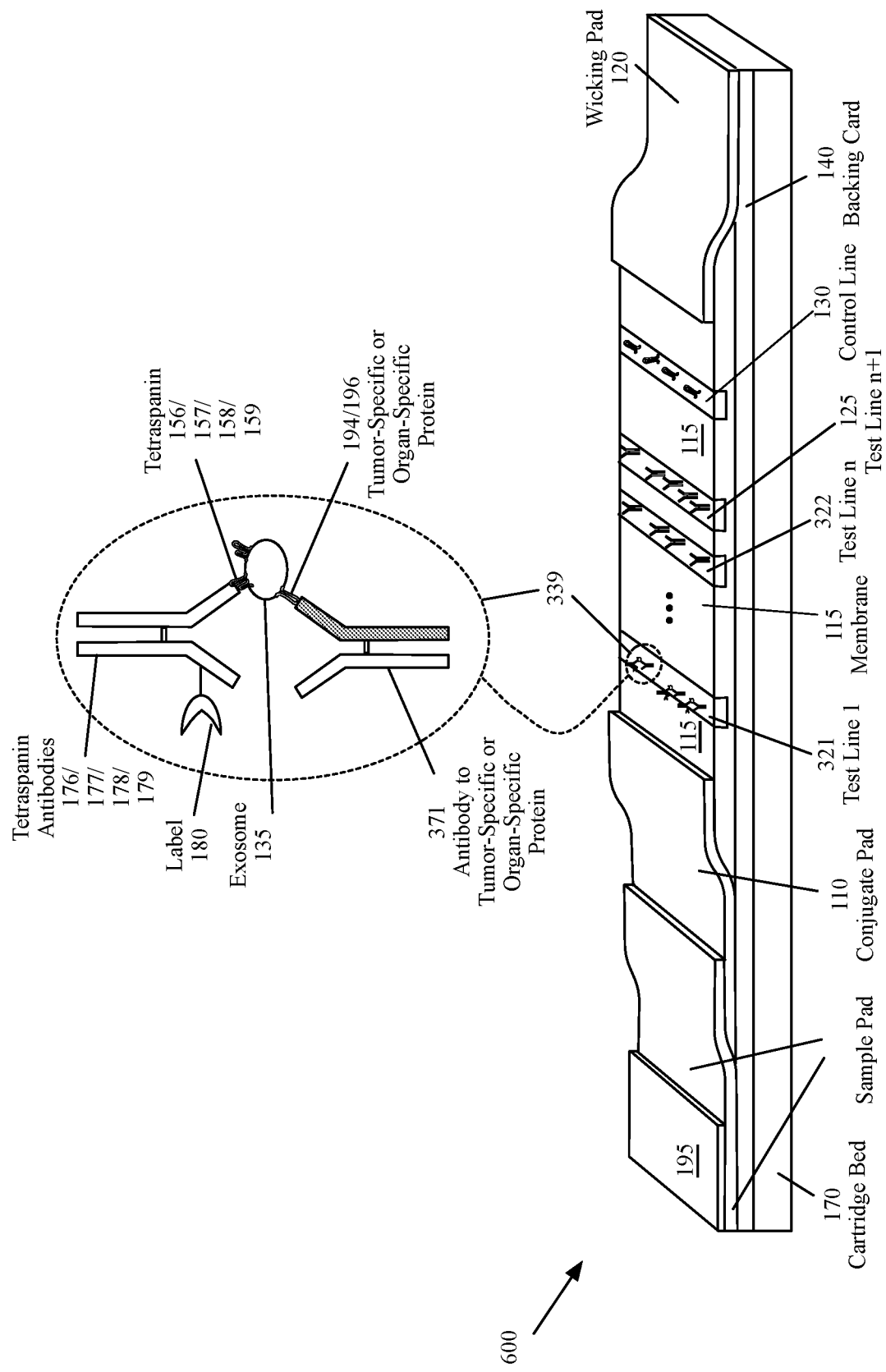
Figure 6D:
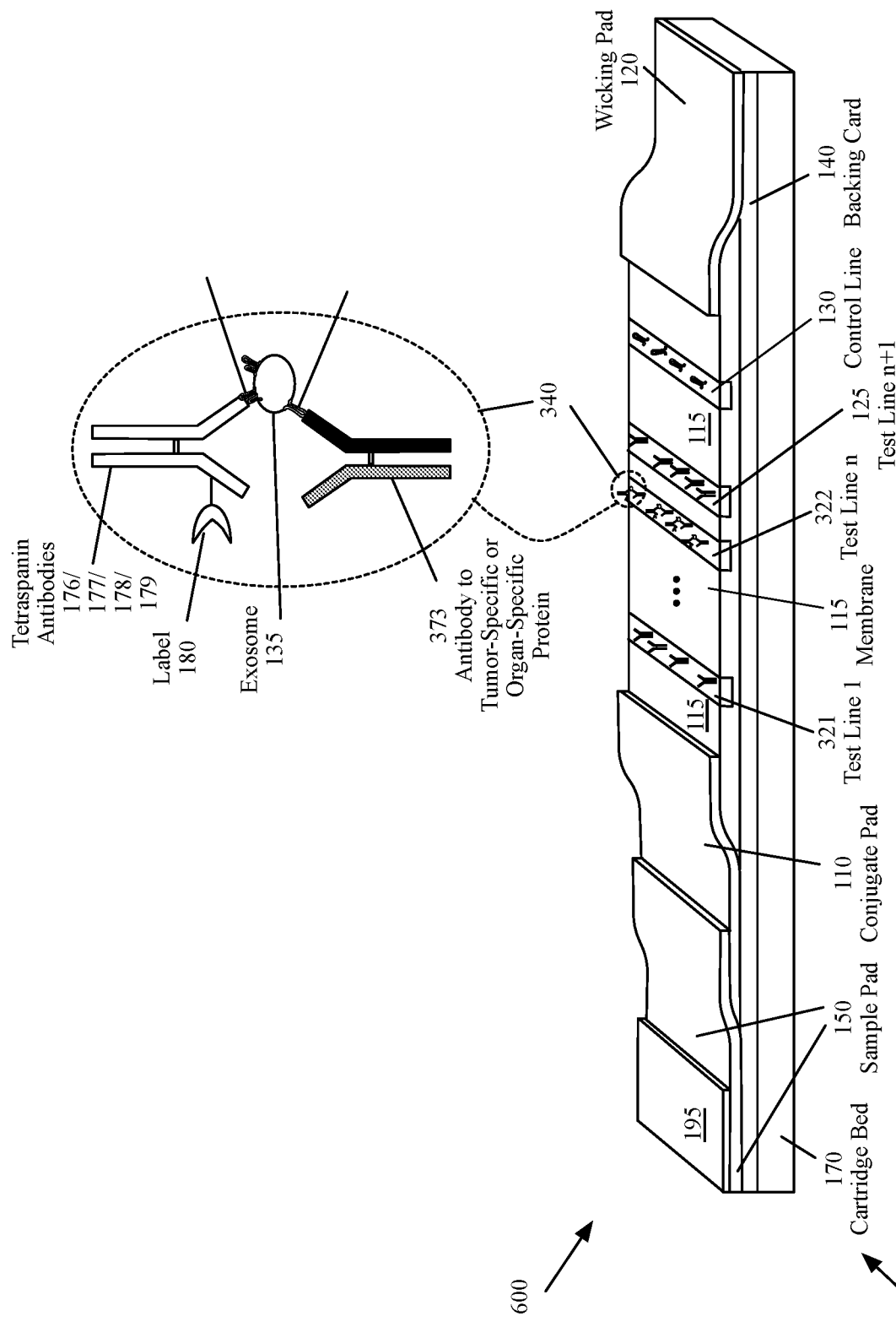
Figure 6E:
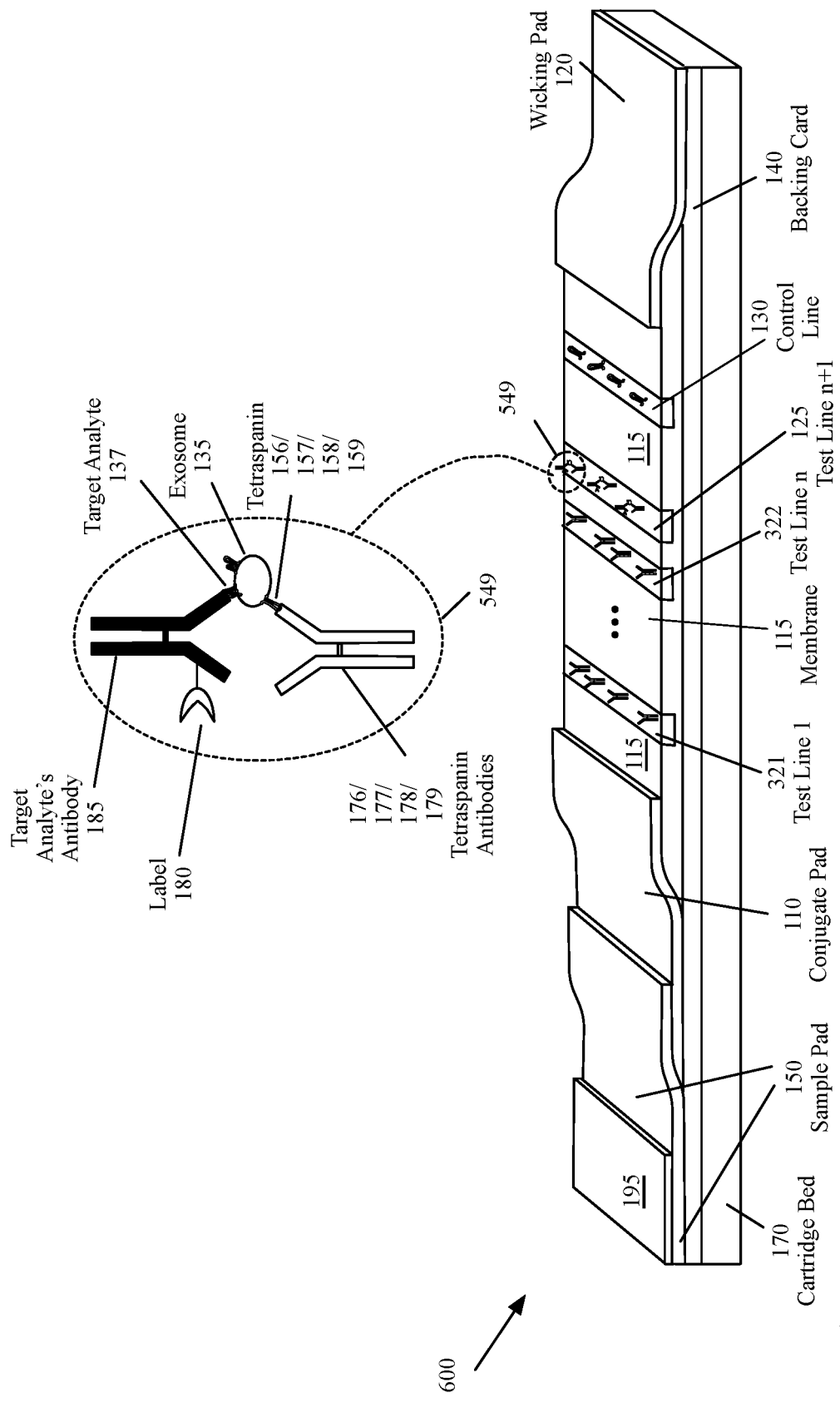
Figure 6F:
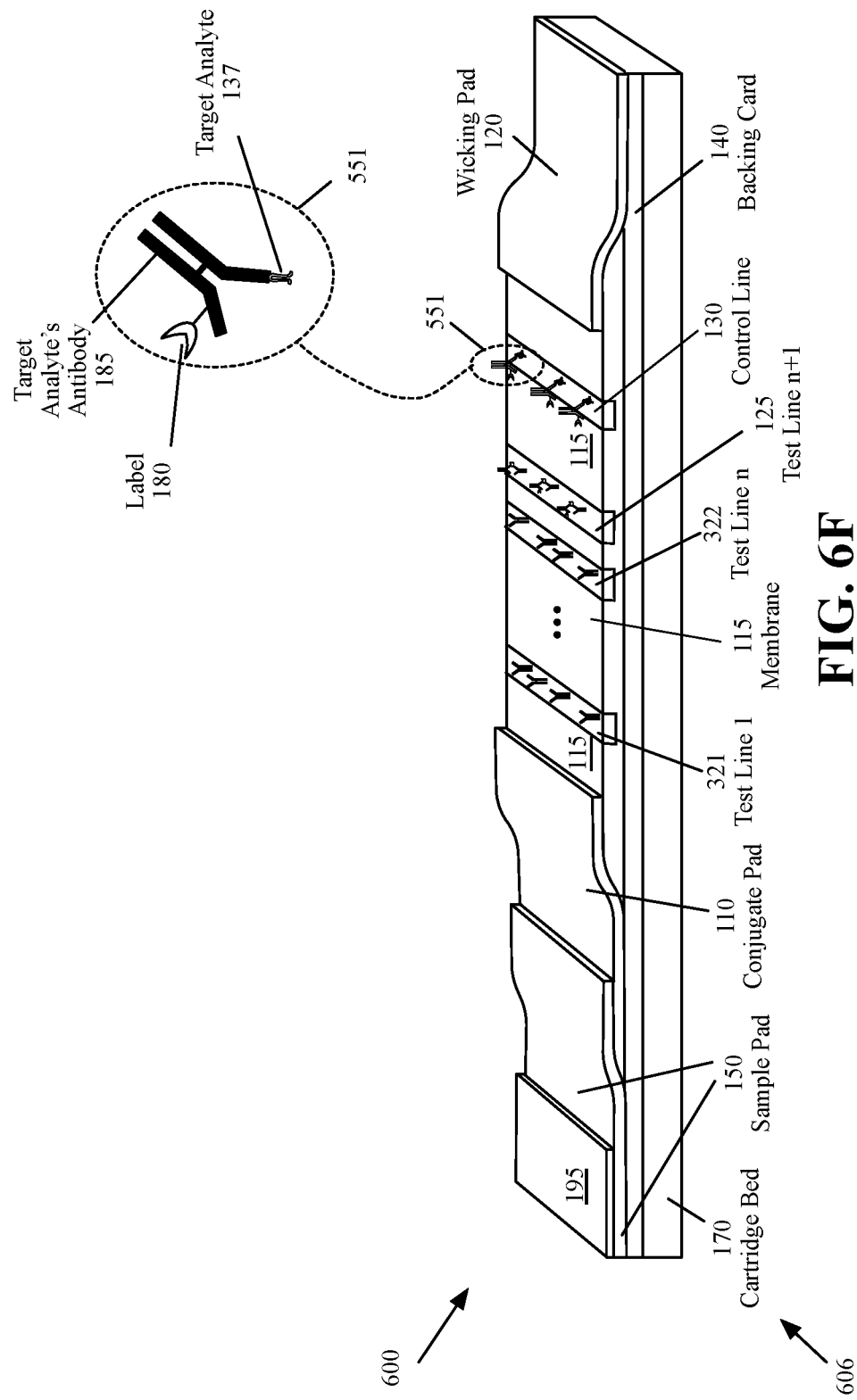

FIGS. 6A-6F, as shown, include six stages 601-607. In stage 601 (FIG. 6A), the sample fluid 190 may be applied to the sample pad 150. When the sample fluid 190 includes blood, the LFA device 600 may have the plasma filter 195 and the sample fluid 190 may be applied to the plasma filter 195. In the embodiments that do not include a sample pad 150, the sample fluid 190 may be applied to the conjugate pad 110 (or applied to a plasma filter located on the conjugate pad when the sample fluid includes blood). The expanded views 141-145 of FIG. 6A illustrate similar items as the corresponding expanded views of FIGS. 1A, 3A, and 5A.

The unlabeled binding reagent that is immobilized on each test line 321-322 may be an antibody 371-372 to an organ-specific protein, such as the organ-specific protein 196, or a tumor-specific protein, such as the tumor-specific protein 194. As described above, some proteins may act both as tumor-specific and organ-specific proteins. The LFA device 600 may be configured such that the organ-specific proteins or the tumor-specific proteins that bind to the immobilized antibodies 371-372 are different proteins.

With reference to FIG. 6A, a quantity of an antibody 371 to an organ-specific protein or a tumor-specific protein may be immobilized on the test line 321 (as shown in the expanded view 331), a quantity of an antibody 372 to an organ-specific protein or a tumor-specific protein may be immobilized on the test line 322 (as shown in the expanded view 332), etc. Although two test lines 321-322 are shown for capturing the tumor-specific or organ-specific proteins, different embodiments of the LFA device 600 may include any number of one or more test lines similar to the test lines 321-322 for capturing the tumor-specific or organ-specific proteins. Other components of the LFA device 600 may be similar to the corresponding components of the LFA devices 100, 300, and 500 described above.

In stage 602 (FIG. 6B), the fluid material may have reached the conjugate pad 110. As shown in the expanded views 546 and 547, the target analyte 137 on the surface of the exosomes 135 in the fluid material may bind with the target analyte antibody 185. It should be noted that, depending on the condition of the subject (e.g., a person or an animal) from which the sample fluid 190 (FIG. 5A) is drawn, there may or may not be any exosome with the target analyte 137 in the sample fluid.

The exosomes 135 with the target analyte 137 on their surface that are bound with the target analyte antibody 185 may form immunocomplexes. The immunocomplexes and the rest of the fluid material 198 may continue to move, by capillary action, from the conjugate pad 110 to the membrane 115.

In stage 603 (FIG. 6C), the fluid material may have reached the test line 321. As shown in the expanded view 339, the tumor-specific or organ-specific antibodies 371 that are immobilized on the test line 321 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). The binding results in a second immunocomplex (the immunocomplex shown in the expanded view 339). The label 180 on the immobilized second immunocomplex colors the test line 321.

The intensity of the colored test line 321 is correlated with the density of the tumor-specific or organ-specific protein on the surface of the exosomes 135 in the sample fluid that correspond to the immobilized antibody 371. The second immunocomplex includes the exosomes 135 that are bound (through the tumor-specific protein 194 or the organ-specific protein 196 on their surface) with the immobilized antibodies 371, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 371, no immunocomplex binds with the immobilized antibody 371 on the test line 321. As a result, the test line 321 does not change color.

The exosomes that lack the tumor-specific protein 194 or the organ-specific protein 196 that corresponds to the immobilized antibodies 371 on their surface may not bind to the immobilized antibodies 371 on the test line 321 and may continue to move, with the rest of the fluid material, toward the test line 342. It should be noted that some embodiments of the LFA device 600 may only include the test lines 341 and 125. These embodiments may not include stages 604. In these embodiments, the unbound material may move from the list line 321 toward the test line 125, as described below with reference to stage 305.

In stage 604 (FIG. 6D), the fluid material may have reached the test line 322. As shown in the expanded view 340, the tumor-specific or organ-specific antibodies 372 that are immobilized on the test line 322 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). It should be noted that the tumor-specific protein 194 or organ-specific protein 196 that correspond to the antibody 372 that is immobilized on the test line 322 is different than the tumor-specific protein 194 or organ-specific protein 196 that correspond to the antibody 371 that is immobilized on the test line 321. The binding on the test line 342 results in a third immunocomplex (the immunocomplex shown in the expanded view 340). The label 180 on the immobilized third immunocomplex colors the test line 322.

The intensity of the colored test line 322 is correlated with the density of the tumor-specific or organ-specific protein on the surface of the exosomes 135 in the sample fluid that correspond to the immobilized antibody 372. The third immunocomplex includes the exosomes 135 that are bound (through the tumor-specific protein 194 or the organ-specific protein 196 on their surface) with the immobilized antibodies 372, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 372, no immunocomplex binds with the immobilized antibody 372 on the test line 322. As a result, the test line 322 does not change color.

The exosomes that lack the tumor-specific protein 194 or the organ-specific protein 196 that corresponds to the immobilized antibodies 372 on their surface may not bind to the immobilized antibodies 372 on the test line 322 and may continue to move, with the rest of the fluid material, toward the test line 343. It should be noted that some embodiments of the LFA device 600 may include more than two test lines 341-342 to capture tumor-specific and/or organ-specific proteins. These embodiments may include additional stages similar to the 304.

In stage 605 (FIG. 6E), the fluid material may have reached the test line 125. As shown in the expanded view 549, the tetraspanin antibodies (e.g., the tetraspanin antibodies 176-179) that are immobilized on the test line 125 may bind with the tetraspanins 156-159 on the exosomes 135 that have been bound to the target analyte's antibodies 185. The binding results in an immunocomplex (the immunocomplex shown in the expanded view 549). The label 180 on the immobilized immunocomplex colors the test line 125.

Since the tetraspanins' antibodies 176-179 are immobilized on the test line 125, the exosomes that do not have the target analyte 137, and are not bound to a labelled target analyte's antibody, may also bind with the tetraspanins' antibodies 176-179 and become immobilized on the test line 125. The test line may, therefore, immobilize some particles that do not have a label. These unlabeled particles bind to, and consume, some of the immobilized tetraspanin antibodies 176-179 on the test line 125.

Accordingly, the test line 125 of the LFA device 600 of the present embodiment is designed such that enough tetraspanin antibodies 176-179 are immobilized on the test line 125 to allow for a percentage of the immobilized tetraspanin antibodies 176-179 to be consumed by the exosomes that do not carry a label and the test line still changes color when the sample fluid includes the target analyte. The amount of the immobilized tetraspanin antibodies 176-179 on the test line, in some embodiments, may be determined by a series of experimental tests to ensure the test line changes color when the target analyte is present in the sample fluid.

When the sample fluid does not include the target analyte, no immunocomplex binds with the immobilized antibody on the test line 125. As a result, the test line 125 does not change color. The labeled target analyte's antibodies 185 that do not bind to the target analyte 137 may continue to move, with the rest of the fluid material, toward the control line 130 and the wicking pad 120.

In stage 606 (FIG. 6F), the fluid material may have reached the control line 130. As shown in the expanded view 551, the free labeled target analyte's antibodies 185 in the fluid material may bind to the immobilized target analyte 137 on the control line 130. This binding may result in a colored control line 130, which confirms that the test has operated correctly regardless of whether or not the target analyte has been present in the sample fluid. The fluid material that do not bind to the control line 130 may continue to flow from the membrane 115 into the wicking pad 120 to absorb the fluid material that are not taken up by the test line 125 and the control line 130 while maintaining the capillary flow from the membrane 125 into the wicking pad 120.

With reference to FIGS. 6A-6D, the results of a test on the LFA device 600 may be interpreted as follows. When none of the test lines 321-322 and 125 are colored at the end of a test, neither the target analyte 137 nor the tumor-specific proteins, nor the organ-specific proteins whose antibodies where immobilized on the test lines 321-322 were present in the sample fluid 190 in detectable amounts. When the test line 125 is colored at the end of a test but none of the test lines 321-322 are colored, the target analyte 137 (e.g., and without limitation, a general marker of a malignancy such as cancer) is detected in the sample fluid but the malignancy may not be attributed to any specific tumor or specific organ.

When the test line 125 and at least one of the test lines are colored 321-322 at the end of a test, the target analyte 137 (e.g., and without limitation, a general marker of a malignancy such as cancer) is detected in the sample fluid. In addition, the malignancy may be attributed with a high probability to the specific tumor(s) or the specific organ(s) whose exosome protein(s) 194/196 was/were captured on the colored test line(s) 321-322.

When the test line 125 is not colored but at least, one of the test lines are colored 321-322 at the end of a test, the target analyte 137 attributed to a malignancy is not detected. In this scenario, the test line(s) 321-322 may have been colored either due to the presence of the organ-specific proteins on the surface of exosomes released from a healthy organ or due to the detected exosome proteins being released by a tumor that does not have the general marker (i.e., the target analyte protein).

In the embodiment of FIGS. 6A-6F, multiple test lines 321-322 and 125 were placed on the same test strip that also includes the sample pad 150, the conjugate pad 110, the membrane 115, the control line 130, and the wicking pad 120. Some embodiments may place each test lines 321-322 and 125 on a separate strip where each strip may include a sample pad 150, a conjugate pad 110, a membrane 115, a control line 130, and a wicking pad 120. The multiple strips may be placed inside the same test cartridge.

FIGS. 7A-7D are functional diagrams illustrating an LFA device 700 and a method that uses an antibody specific to the target analyte as the detection antibody and includes multiple test strips with test lines for capturing a set of one or more organ-specific or tumor-specific proteins and a target analyte, according to various aspects of the present disclosure. The LFA device 700 may be a portable device (e.g., a handheld device or benchtop device) that is used to analyze a sample fluid 190 to determine the presence and/or the amount of one or more analytes, one or more tumor-specific proteins, and/or one or more organ-specific proteins.

With reference to FIGS. 7A-7D, the LFA device 700 may include several test strips 781-783. Each two adjacent test strips may be separated by a gap 770 that may prevent any fluids from flowing from one test strip into the other. The multiple strip LFA device 700 may include a cartridge (only the cartridge's bed 170 is shown for clarity) that encompasses both of the test strips 781-783. Each of the test strips 781-783 may include separate sample pads 150, separate membranes 115, separate test lines 321-322 and 125, separate control lines 130, and separate wicking pads 120.

The test line 125 may be located on the strip 783 and may be used to detect a target analyte 137. The target analyte 137, in some embodiments, may be a protein that is a general marker that identifies malignancies. The test line 125 of the LFA device 700 may be similar to the test line 125 of the LFA devices 100 and 300, described above.

In addition to the test line 125 located on the test strip 783, the LFA device 700 may include n (where n is an integer greater than or equal to 1) test lines 321-322 located on the corresponding test strips 781-782 to detect organ-specific and/or tumor-specific proteins. The test lines 321-322 may be made of a porous material, as described above, with reference to the test line 125 of the LFA devices 100, 300, 400, and 500.

Figure 7A:
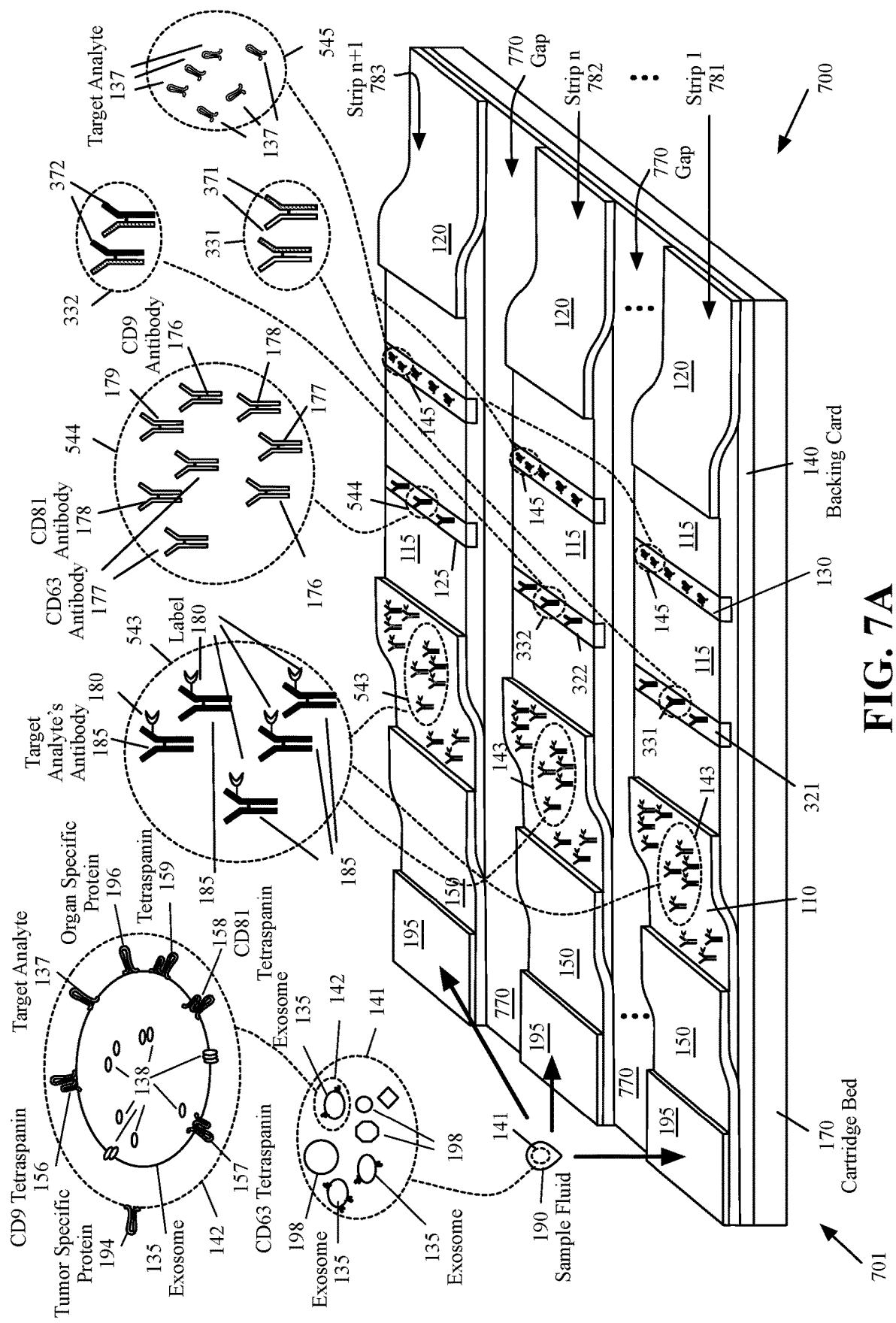
FIGS. 7A-7D are functional diagrams illustrating an LFA device and a method that that uses an antibody specific to the target analyte as the detection antibody and includes multiple test strips with test lines for capturing a set of one or more organ-specific or tumor-specific proteins and a target analyte, according to various aspects of the present disclosure.
Figure 7B:
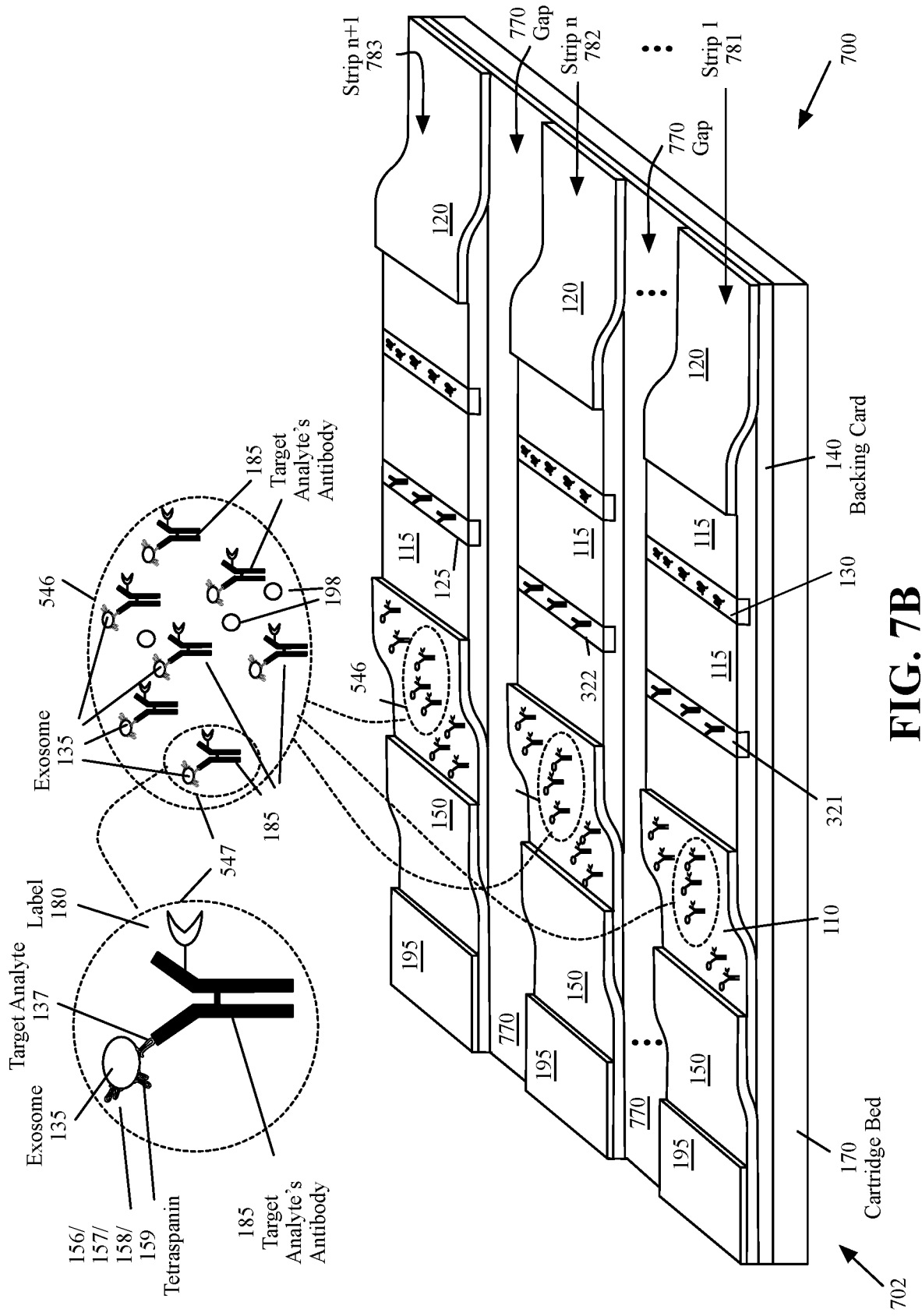
Figure 7C:
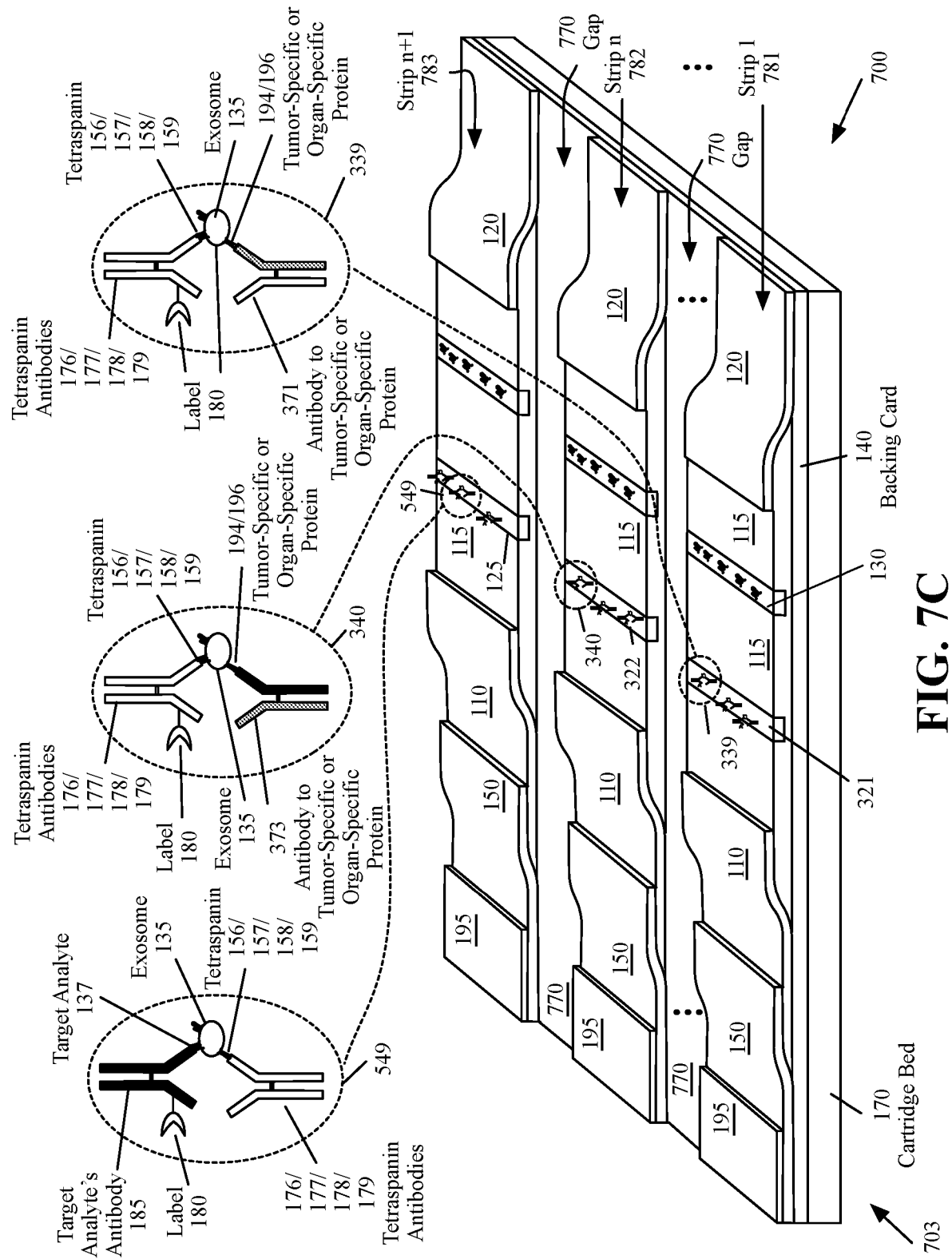
Figure 7D:
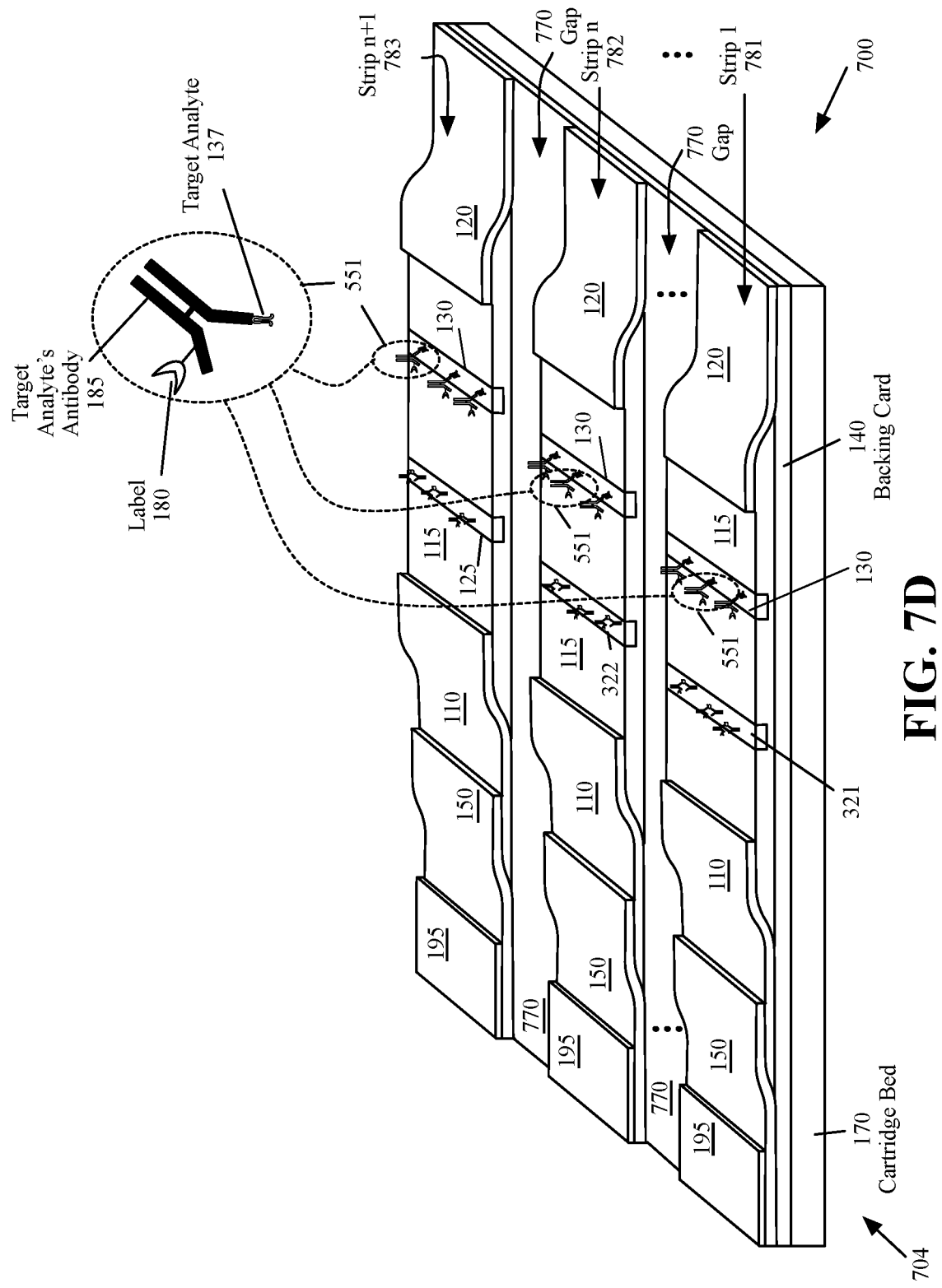

FIGS. 7A-7D, as shown, include four stages 701-704. In stage 701 (FIG. 7A), the sample fluid 190 may be applied on the sample pads 150 of each test strip 781-783. When the sample fluid 190 includes blood, the LFA 700 may have the plasma filters 195 on each test strip 781-783 and the sample fluid 190 may be applied to the plasma filters 195. In the embodiments that do not include a sample pad 150, the sample fluid 190 may be applied to the conjugate pads 110 (or applied to plasma filters located on the conjugate pads when the sample fluid includes blood). The expanded views 141-145 of FIG. 7A illustrate similar items as the corresponding expanded views of FIGS. 1A, 3A, 5A, and 6A.

The unlabeled binding reagent that is immobilized on each test line 321-323 may be an antibody 371-372 to an organ-specific protein, such as the organ-specific protein 196, or a tumor-specific protein, such as the tumor-specific protein 194. As described above, some proteins may act both as tumor-specific and organ-specific proteins. The LFA device 700 may be configured such that the organ-specific proteins or the tumor-specific proteins that bind to the immobilized antibodies 371-372 are different proteins.

With reference to FIG. 7A, a quantity of an antibody 371 to an organ-specific protein or a tumor-specific protein may be immobilized on the test line 321 located on the test strip 781 (as shown in the expanded view 331), a quantity of an antibody 372 to an organ-specific protein or a tumor-specific protein may be immobilized on the test line 322 located on the test strip 782 (as shown in the expanded view 332), etc. Although two test strips 781-782 and the corresponding test lines 321-322 are shown for capturing the tumor-specific or organ-specific proteins, different embodiments of the LFA device 700 may include any number of one or more test strips and the corresponding test lines similar to the test strips 781-782 and the test lines 321-322 for capturing the tumor-specific or organ-specific proteins. Other components of the LFA device 700 may be similar to the corresponding components of the LFA devices 100, 300, 500, and 600 described above with reference to FIGS. 1A-1D and FIGS. 3A-3F).

In stage 702 (FIG. 7B), the fluid material may have reached the conjugate pads 110 of the test strips 781-783. As shown in the expanded views 546 and 547, the target analyte 137 on the surface of the exosomes 135 in the fluid material may bind with the target analyte antibody 185. It should be noted that, depending on the condition of the subject (e.g., a person or an animal) from which the sample fluid 190 (FIG. 5A) is drawn, there may or may not be any exosome with the target analyte 137 in the sample fluid.

The exosomes 135 with the target analyte 137 on their surface that are bound with the target analyte antibody 185 may form immunocomplexes. The immunocomplexes and the rest of the fluid material 198 may continue to move, by capillary action, from the conjugate pad 110 to the membrane 115.

In stage 703 (FIG. 7C), the fluid material may have reached the test lines 321-322 and 125. As shown in the expanded view 339, the tumor-specific or organ-specific antibodies 371 that are immobilized on the test line 321 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). The binding results in an immunocomplex (the immunocomplex shown in the expanded view 339). The label 180 on the immobilized second immunocomplex colors the test line 321.

The intensity of the colored test line 321 is correlated with the density of the tumor-specific or organ-specific protein on the surface of the exosomes 135 in the sample fluid that correspond to the immobilized antibody 371. The immunocomplex shown in the expanded view 339 includes the exosomes 135 that are bound (through the tumor-specific protein 194 or the organ-specific protein 196 on their surface) with the immobilized antibodies 371, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 371, no immunocomplex binds with the immobilized antibody 371 on the test line 321. As a result, the test line 321 does not change color.

As shown in the expanded view 340, the tumor-specific or organ-specific antibodies 372 that are immobilized on the test line 322 may bind with the corresponding tumor-specific protein 194 or organ-specific protein 196 on the exosomes 135 that have been bound to the tetraspanin antibodies (e.g., the tetraspanin antibodies 176-179) through one of their tetraspanins (e.g., the tetraspanins 156-159). It should be noted that the tumor-specific protein 194 or organ-specific protein 196 that correspond to the antibody 372 that is immobilized on the test line 322 is different than the tumor-specific protein 194 or organ-specific protein 196 that correspond to the antibody 371 that is immobilized on the test line 321. The binding on the test line 342 results in an immunocomplex (the immunocomplex shown in the expanded view 340). The label 180 on the immobilized immunocomplex colors the test line 322.

The intensity of the colored test line 322 is correlated with the density of the tumor-specific or organ-specific protein on the surface of the exosomes 135 in the sample fluid that correspond to the immobilized antibody 372. The immunocomplex shown in the expanded view 340 includes the exosomes 135 that are bound (through the tumor-specific protein 194 or the organ-specific protein 196 on their surface) with the immobilized antibodies 372, and are bound (through one of the tetraspanins 156-159 on their surface) with one of the labelled tetraspanins antibodies 176-179. When the sample fluid does not include the tumor-specific protein 194 or the organ-specific protein 196 that corresponds to the immobilized antibodies 372, no immunocomplex binds with the immobilized antibody 372 on the test line 322. As a result, the test line 322 does not change color.

As shown in the expanded view 549, the tetraspanin antibodies (e.g., the tetraspanin antibodies 176-179) that are immobilized on the test line 125 may bind with the tetraspanins 156-159 on the exosomes 135 that have been bound to the target analyte's antibodies 185. The binding results in an immunocomplex (the immunocomplex shown in the expanded view 549). The label 180 on the immobilized immunocomplex colors the test line 125.

Since the tetraspanins' antibodies 176-179 are immobilized on the test line 125, the exosomes that do not have the target analyte 137, and are not bound to a labelled target analyte's antibody, may also bind with the tetraspanins' antibodies 176-179 and become immobilized on the test line 125. The test line may, therefore, immobilize some particles that do not have a label. These unlabeled particles bind to, and consume, some of the immobilized tetraspanin antibodies 176-179 on the test line 125.

Accordingly, the test line 125 of the LFA device 700 of the present embodiment is designed such that enough tetraspanin antibodies 176-179 are immobilized on the test line 125 to allow for a percentage of the immobilized tetraspanin antibodies 176-179 to be consumed by the exosomes that do not carry a label and the test line still changes color when the sample fluid includes the target analyte. The amount of the immobilized tetraspanin antibodies 176-179 on the test line, in some embodiments, may be determined by a series of experimental tests to ensure the test line changes color when the target analyte is present in the sample fluid.

When the sample fluid does not include the target analyte, no immunocomplex binds with the immobilized antibody on the test line 125. As a result, the test line 125 does not change color. The labeled target analyte's antibodies 185 that do not bind to the target analyte 137 may continue to move, with the rest of the fluid material, toward the control line 130 and the wicking pad 120.

The exosomes that lack the tumor-specific protein 194 or the organ-specific protein 196 that corresponds to the immobilized antibodies 371 on their surface may not bind to the immobilized antibodies 371 on the test line 321 and may continue to move, with the rest of the fluid material, toward the control line 130 on the test strip 781.

The exosomes that lack the tumor-specific protein 194 or the organ-specific protein 196 that corresponds to the immobilized antibodies 372 on their surface may not bind to the immobilized antibodies 372 on the test line 322 and may continue to move, with the rest of the fluid material, toward the control line 130 on the test strip 782. It should be noted that some embodiments of the LFA device 700 may include more than two test lines 341-342 to capture tumor-specific and/or organ-specific proteins. These embodiments may include additional test strips similar to the test strips 781-782. Some embodiments of the LFA device 700 may include one test line 341 to capture tumor-specific and/or organ-specific proteins. These embodiments may not include the test strip 782.

In stage 704 (FIG. 7D), the fluid material may have reached the control lines 130 of the test strips 781-783. As shown in the expanded view 551, the free labeled target analyte's antibodies 185 in the fluid material may bind to the immobilized target analyte 137 on the control line 130. This binding may result in a colored control line 130, which confirms that the test has operated correctly regardless of whether or not the target analyte has been present in the sample fluid.

The fluid material that do not bind to the control lines 130 may continue to flow from the membranes 115 of the test strips 781-783 into the wicking pads 120 of the test strips 781-783 to absorb the fluid material that are not taken up by the test line 125 and the control line 130 while maintaining the capillary flow from the membrane 125 into the wicking pad 120.

With reference to FIGS. 7A-7D, the results of a test on the LFA device 700 may be interpreted as follows. When none of the test lines 321-322 and 125 are colored at the end of a test, neither the target analyte 137 nor the tumor-specific proteins, nor the organ-specific proteins whose antibodies where immobilized on the test lines 321-322 were present in the sample fluid 190 in detectable amounts. When the test line 125 is colored at the end of a test but none of the test lines 321-322 are colored, the target analyte 137 (e.g., and without limitation, a general marker of a malignancy such as cancer) is detected in the sample fluid but the malignancy may not be attributed to any specific tumor or specific organ.

When the test line 125 and at least one of the test lines are colored 321-322 at the end of a test, the target analyte 137 (e.g., and without limitation, a general marker of a malignancy such as cancer) is detected in the sample fluid. In addition, the malignancy may be attributed with a high probability to the specific tumor(s) or the specific organ(s) whose exosome protein(s) 194/196 was/were captured on the colored test line(s) 321-322.

When the test line 125 is not colored but at least, one of the test lines are colored 321-322 at the end of a test, the target analyte 137 attributed to a malignancy is not detected. In this scenario, the test line(s) 321-322 may have been colored either due to the presence of the organ-specific proteins on the surface of exosomes released from a healthy organ or due to the detected exosome proteins being released by a tumor that does not have the general marker (i.e., the target analyte protein).

II. ELISA Device that Detects and Captures a Target Analyte by Using an Antibody Specific to an Exosome Containing the Target Analyte FIGS. 8A-8I are functional diagrams illustrating an ELISA device 800 and a method that detects and captures a target analyte by using antibodies specific to exosomes containing the target analyte and an immobilized antibody specific to the target analyte, according to various aspects of the present disclosure. The ELISA device 800 may be a portable device (e.g., a handheld device or benchtop device) that is typically used in a lab environment to analyze a sample fluid to determine the presence and/or the amount of one or more target analytes.

The ELISA device 800 may include a microplate 810. The microplate 810 may include different numbers of wells (or cavities) 820. For example, the microplate in a sandwich format ELISA device may include, 96, 384, 1536, etc., wells. In the example of FIGS. 8A-8I, the ELISA device 800 includes 96 wells arranged in 8 rows and 12 columns.

The microplate 810 may be made of plastic material, such as, for example, and without limitations, polystyrene, a derivative of polystyrene, polyvinyl chloride (PVC), etc. Different wells 820 may include samples from the same or different subjects. For example, two or more wells may be used to include sample fluids taken from the same person at different times and/or may include different concentration of samples taken from the same person. Two or more wells may include sample fluids from different persons. The same test may be performed in parallel on the samples in all wells 820.

FIGS. 8A-8I, as shown, include nine stages 801-809. As shown in the expanded view 841 in stage 801 (FIG. 8A), the target analyte's antibody 185 may be immobilized on the bottom of one or more of the wells 820. The target analyte's antibody 185 may be applied as a suitably diluted coating buffer in stage 801 to one or more wells 820 that may be used for a test. The coating buffer may be incubated until adsorbed to the surface of the wells 820. Adsorption may occur passively as the result of hydrophobic interactions between the amino acids side chains on the antibody 185 and the plastic surface of the wells 820. The adsorption may be dependent on time, temperature, and the pH of the coating buffer, as well as the concentration of the antibody 185.

In stage 802 (FIG. 8B), the sample fluid 190 may be added to the well(s) 820 that is/are used in the test. As shown in the expanded view 842, the sample fluid may have a similar composition as the sample fluid of FIG. 1A. As shown in the expanded view 843, the exosomes 135 may have similar composition as the exosomes described above with reference to FIG. 1A.

In stage 803 (FIG. 8C), the exosomes in the fluid sample that include the target analyte 137 on their surface may bind with the immobilized target analyte antibodies 185 in the well(s) 820. As shown in the expanded view 844, exosomes, such as the exosome 835, that do not include the target analyte on their surface, may not bind with the immobilized target analyte antibodies 185. The fluid sample may be left a suitable time in the well(s) 820 in order for the target analyte 137 to bind with the immobilized target analyte antibodies 185.

In stage 804 (FIG. 8D), the unbound material 198 and 835 (FIG. 8C) may be washed away. In some embodiments, washing may be performed one or more times by applying a washing buffer to thoroughly remove the unbound material. As shown in the expanded view 845, only the exosomes 135 with the target analyte 137 bound to the immobilized target analyte's antibodies 185 may be left in the well(s) 820 at the end of stage 804.

Figure 8A:
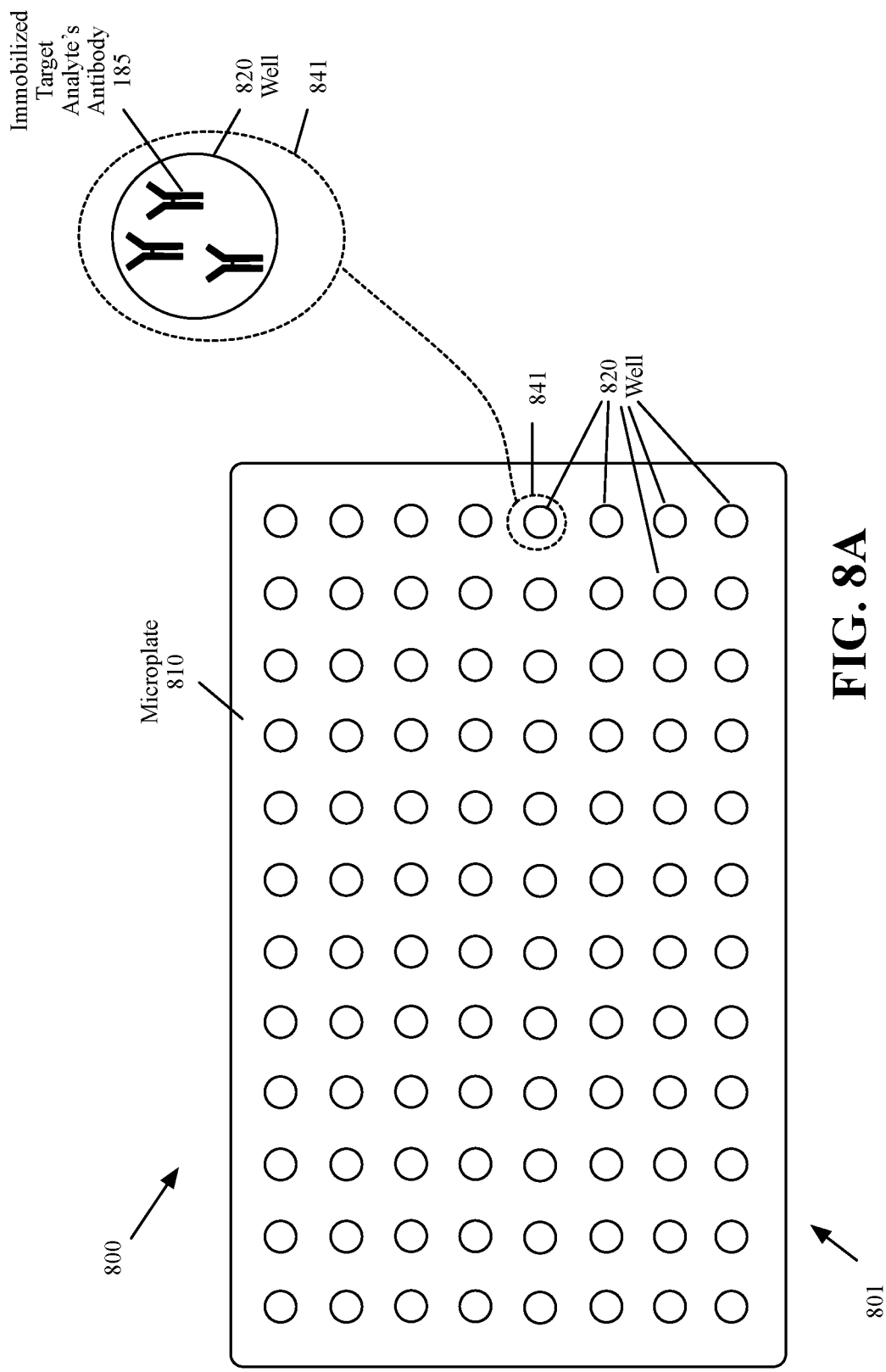
FIGS. 8A-8I are functional diagrams illustrating an ELISA device and a method that detects and captures a target analyte by using antibodies specific to exosomes containing the target analyte and an immobilized antibody specific to the target analyte, according to various aspects of the present disclosure.
Figure 8B:
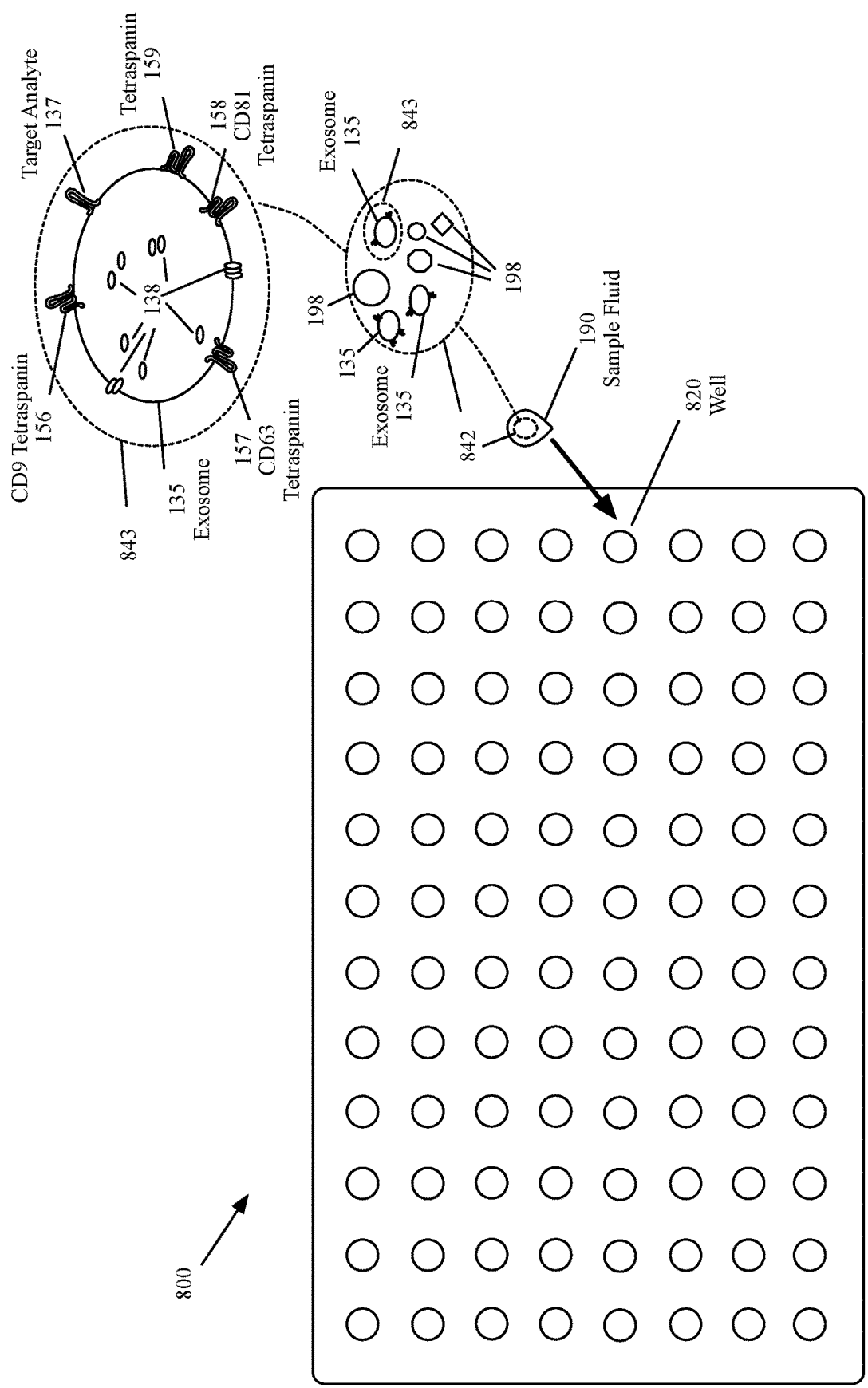
Figure 8C:
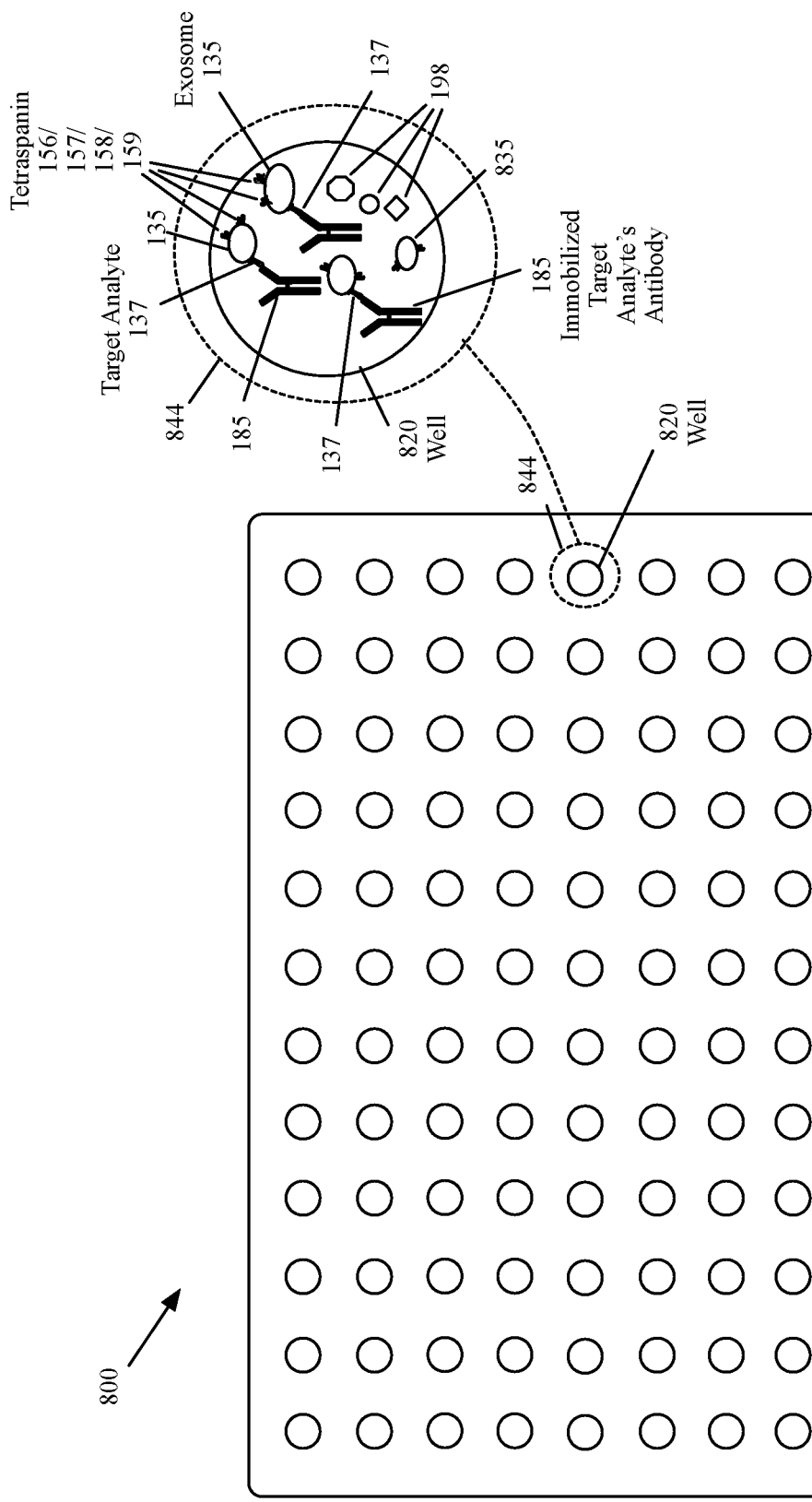
Figure 8D:
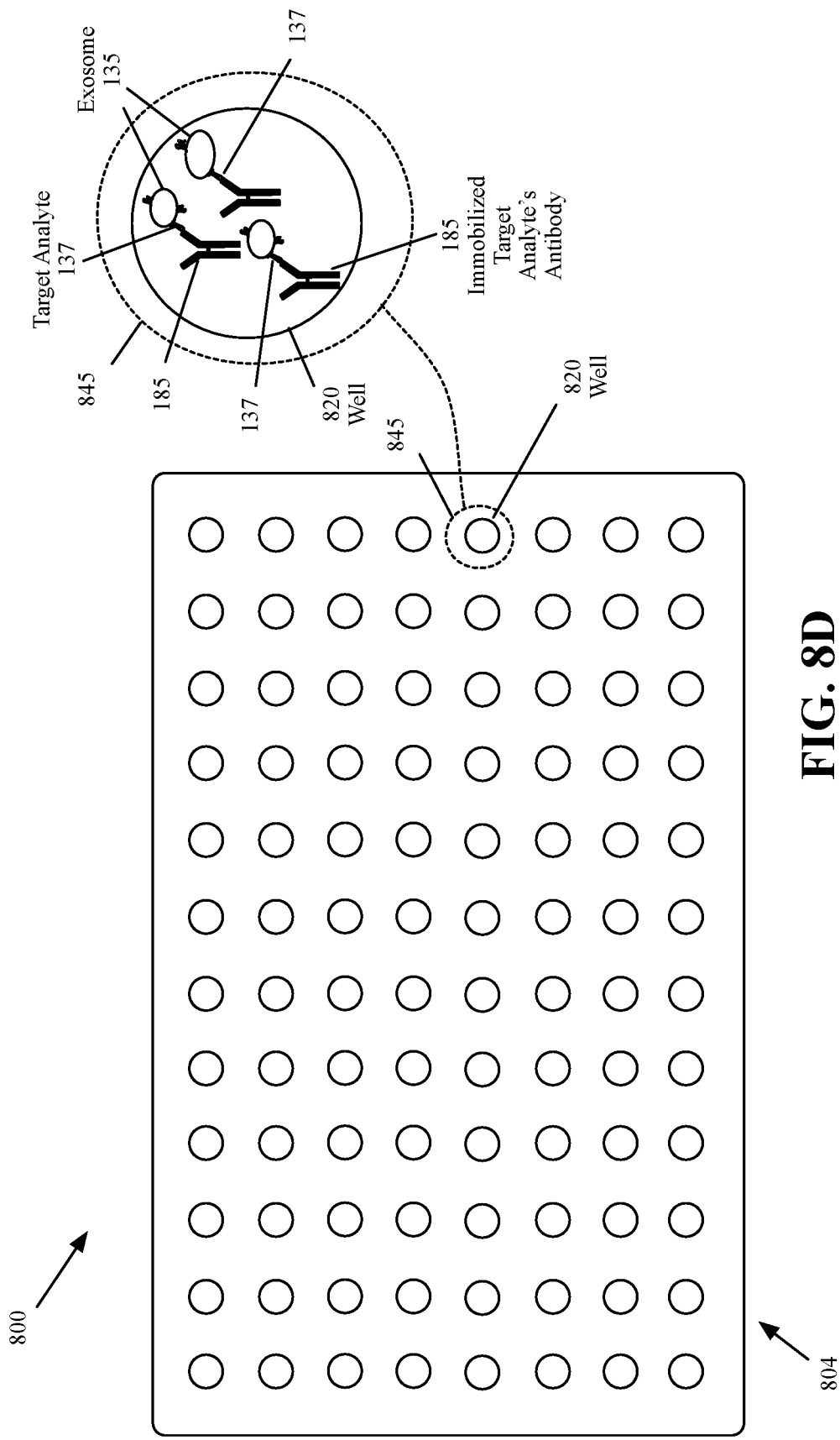
Figure 8E:
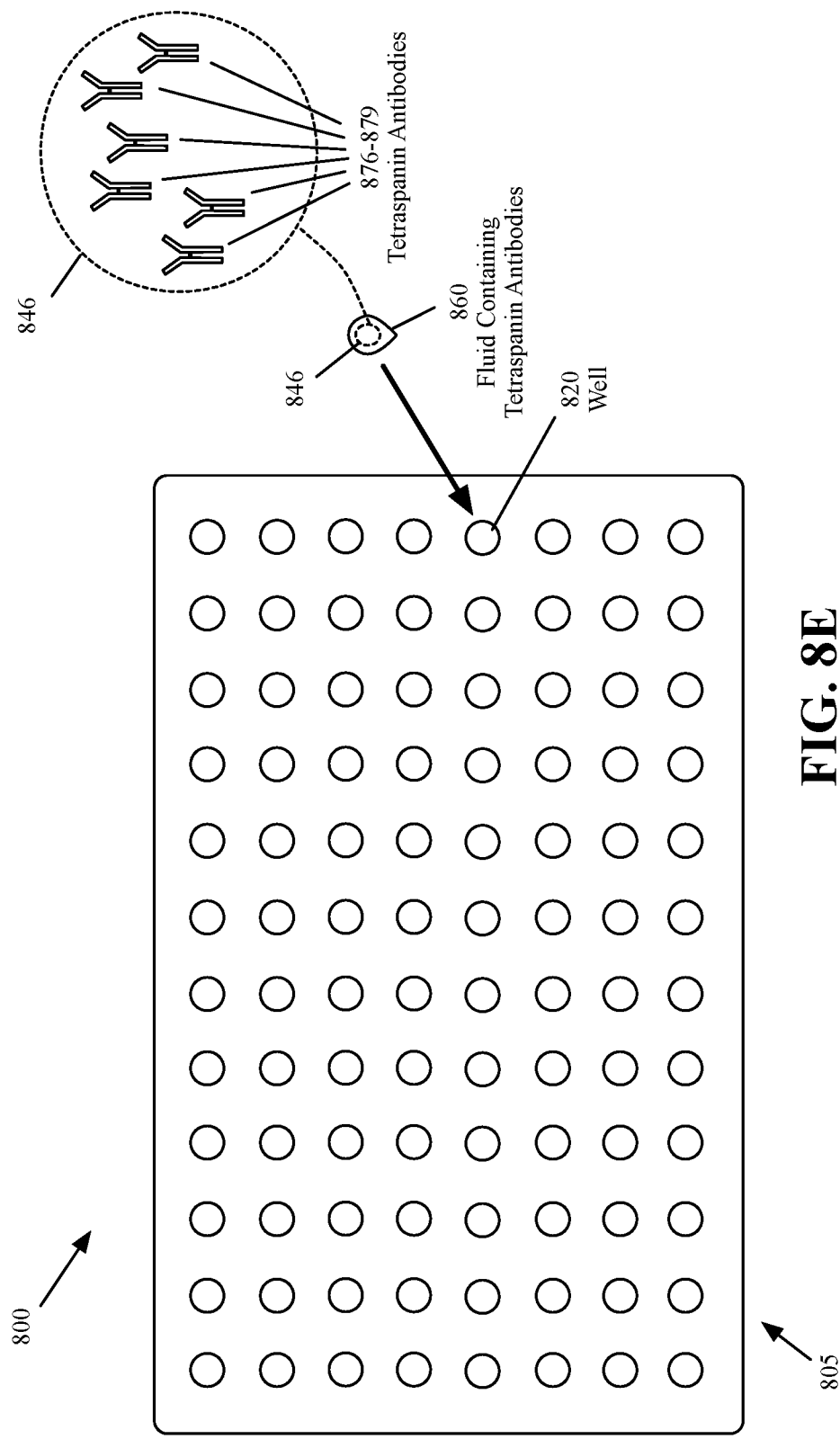
Figure 8F:
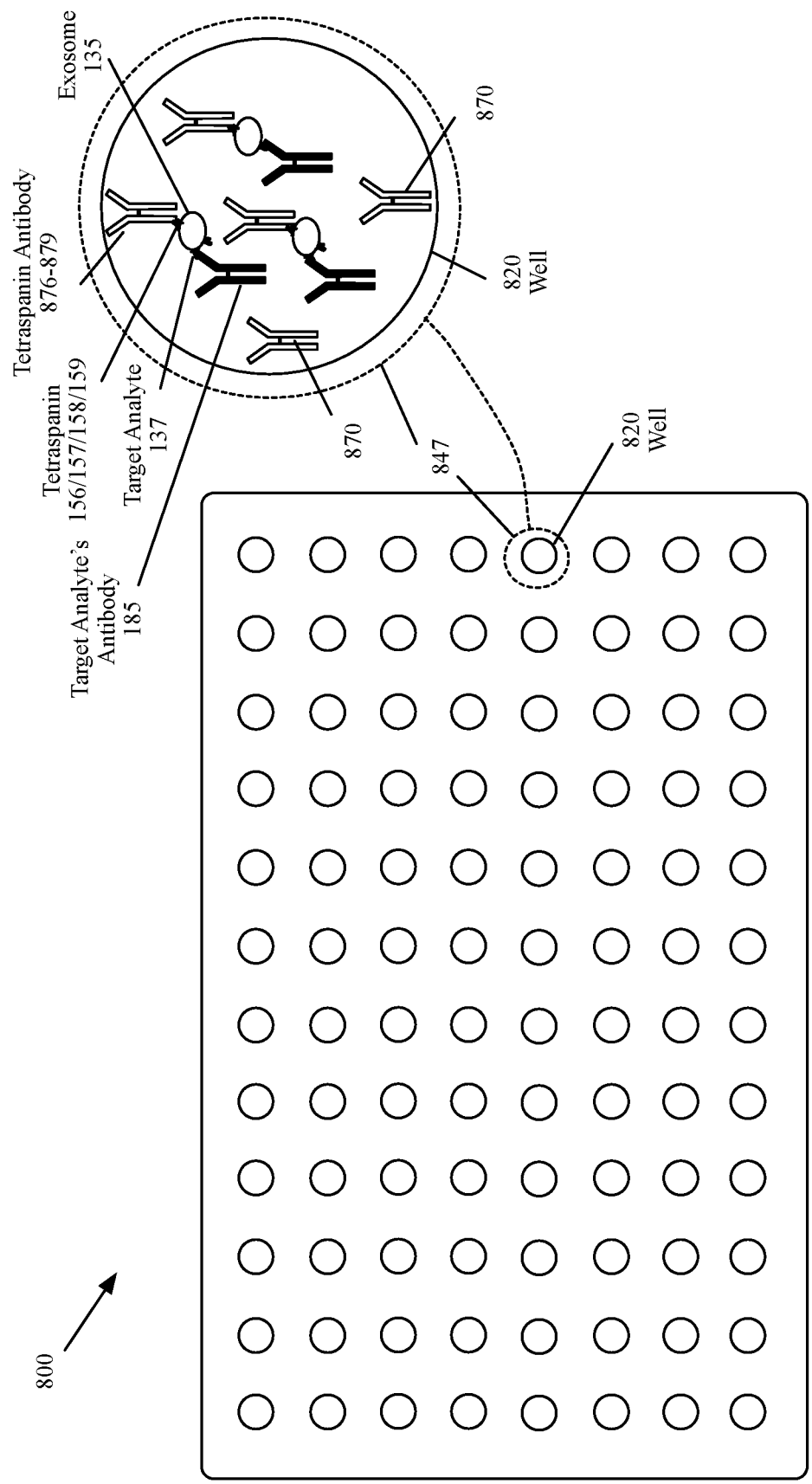
Figure 8G:
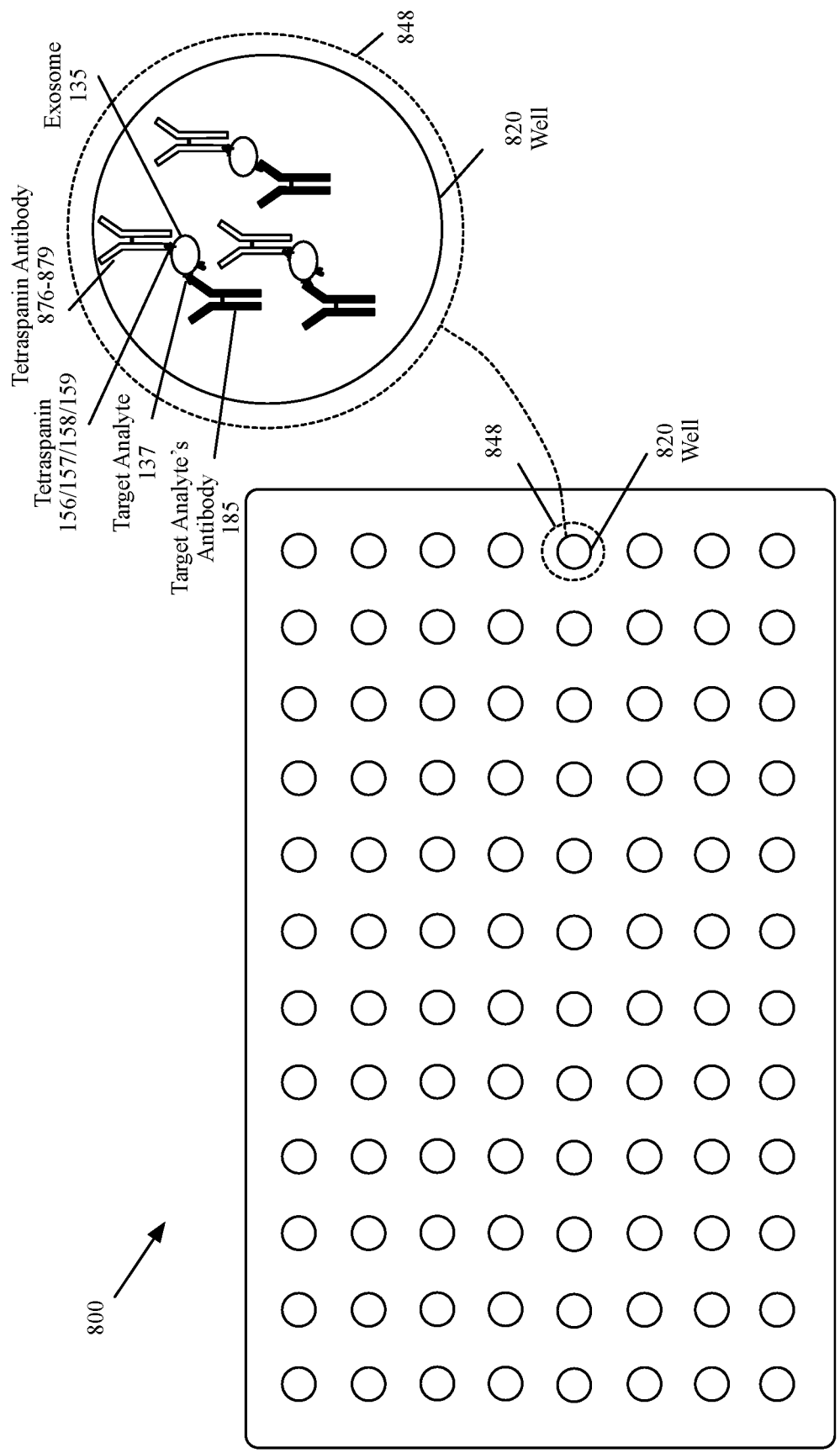
Figure 8H:
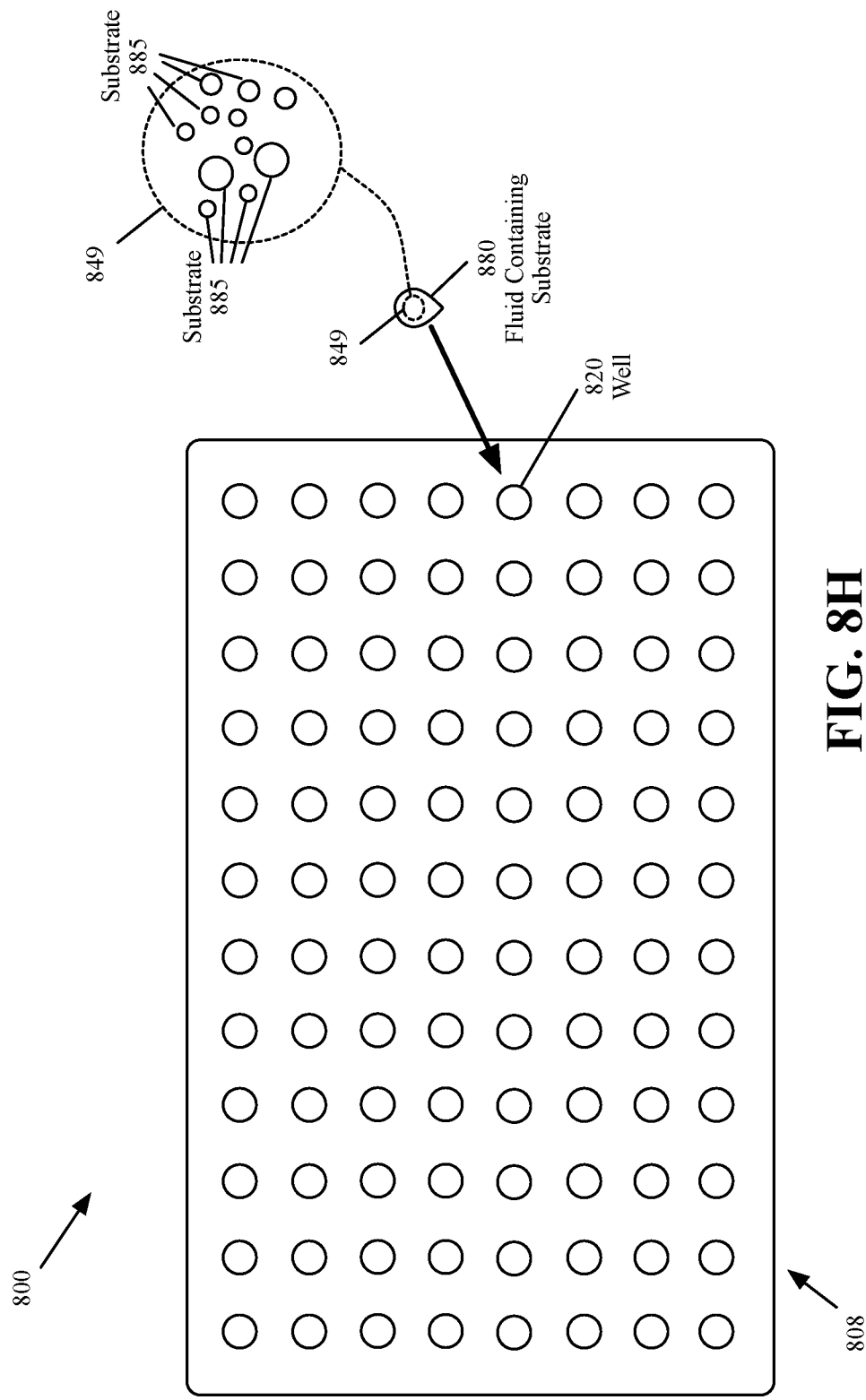
Figure 8I:
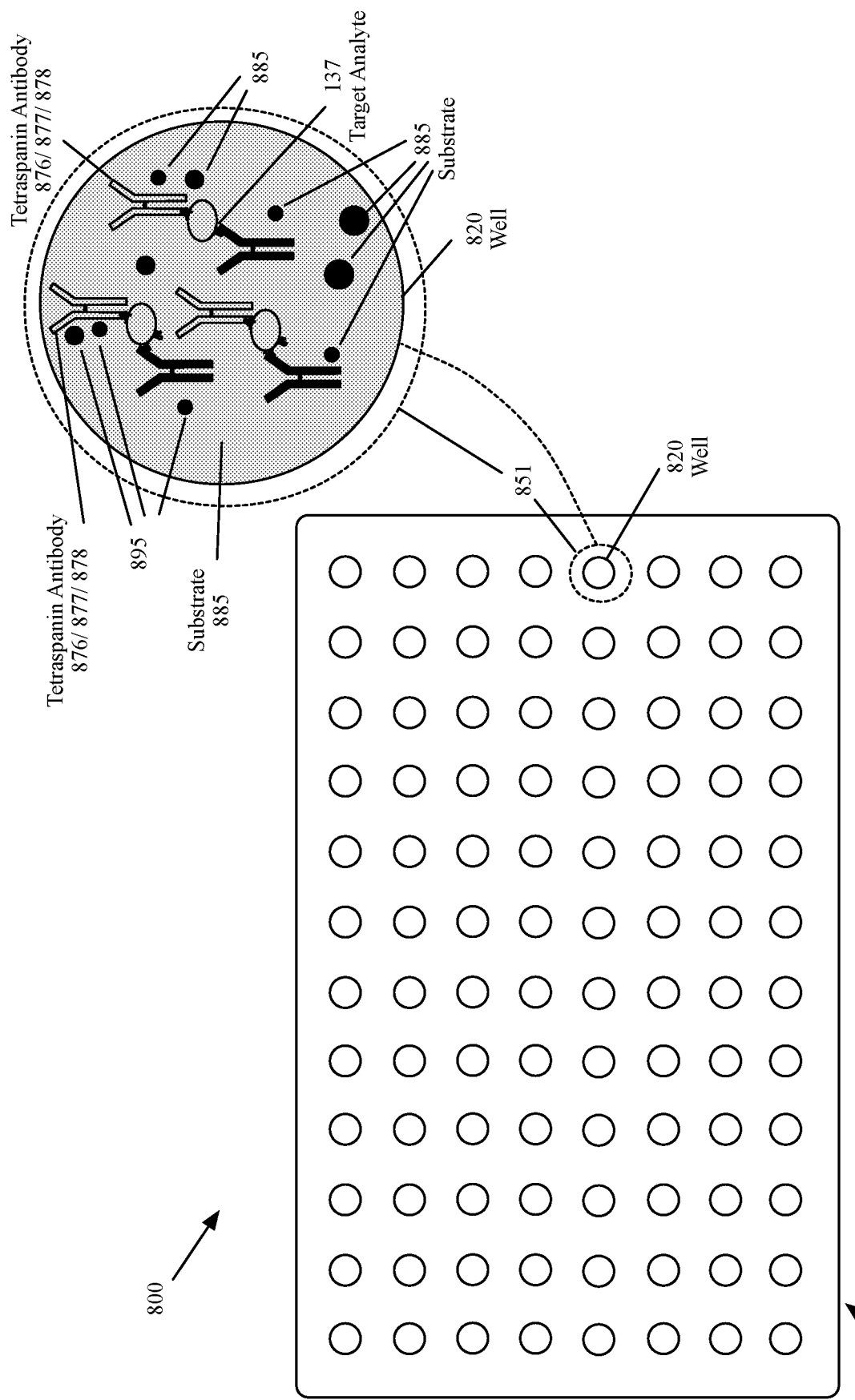
Figure 9A:
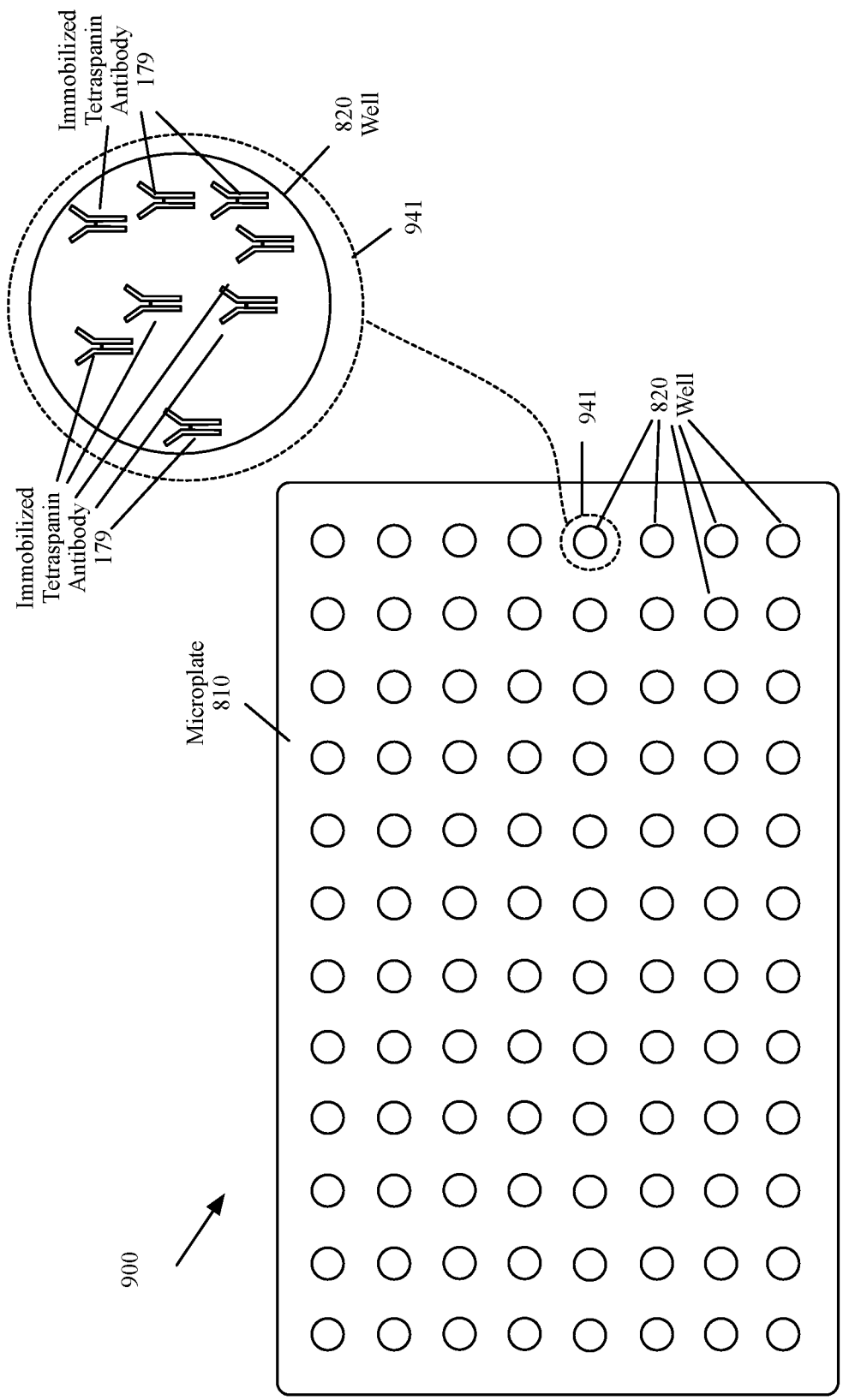
FIGS. 9A-9I are functional diagrams illustrating an ELISA device and a method that detects and captures a target analyte by using immobilized antibodies specific to exosomes containing the target analyte and an antibody specific to the target analyte, according to various aspects of the present disclosure.
Figure 9B:
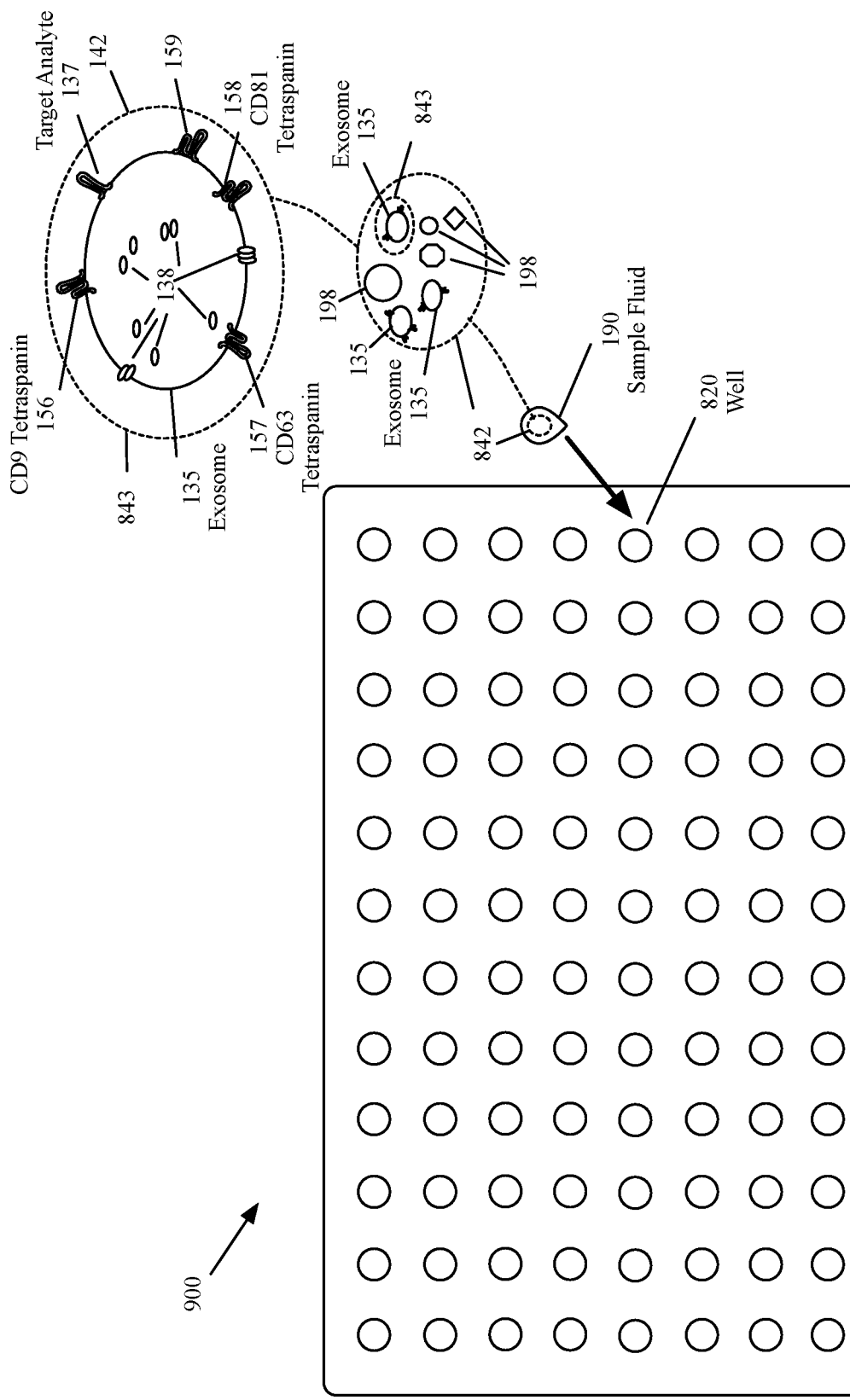
Figure 9C:
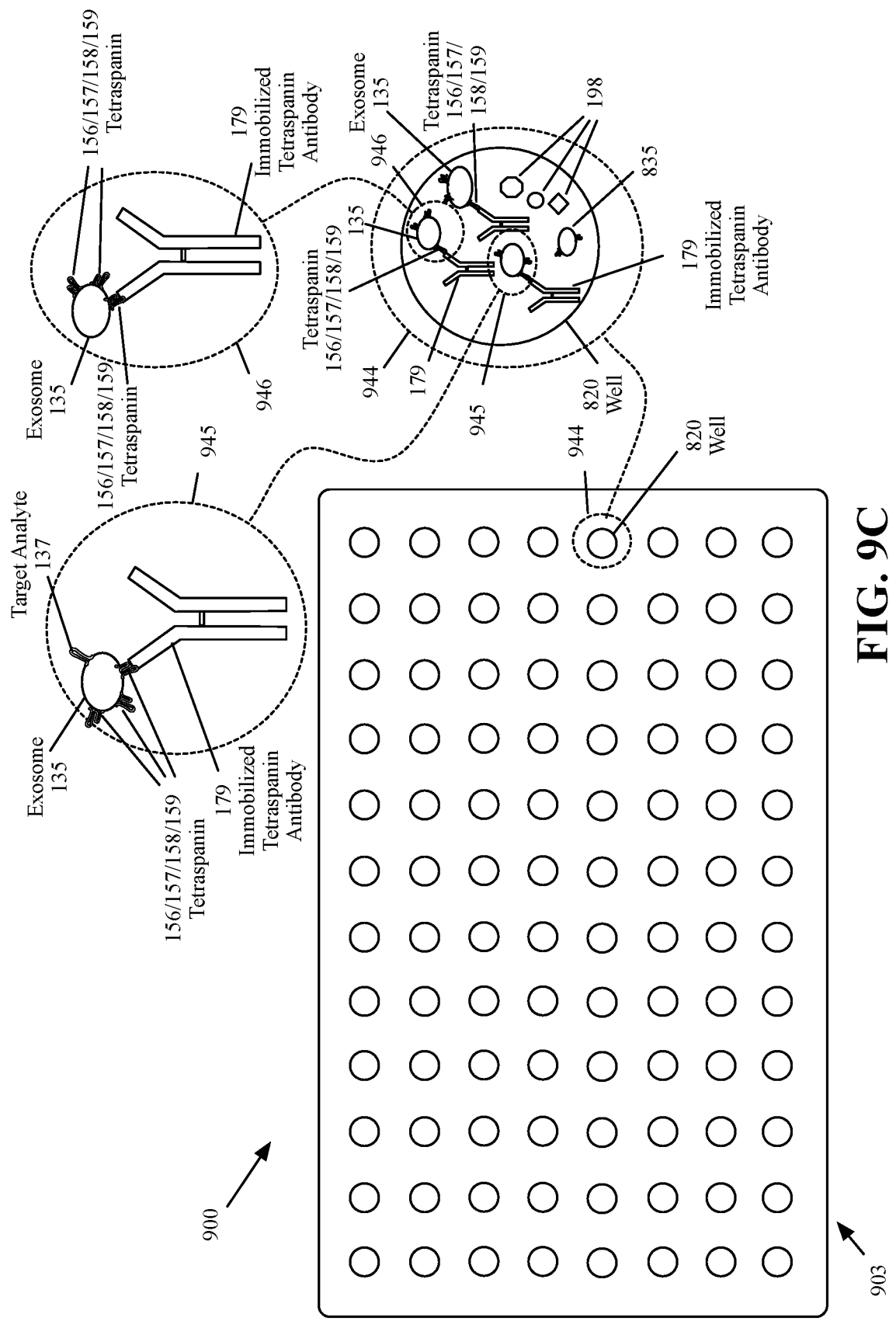
Figure 9D:
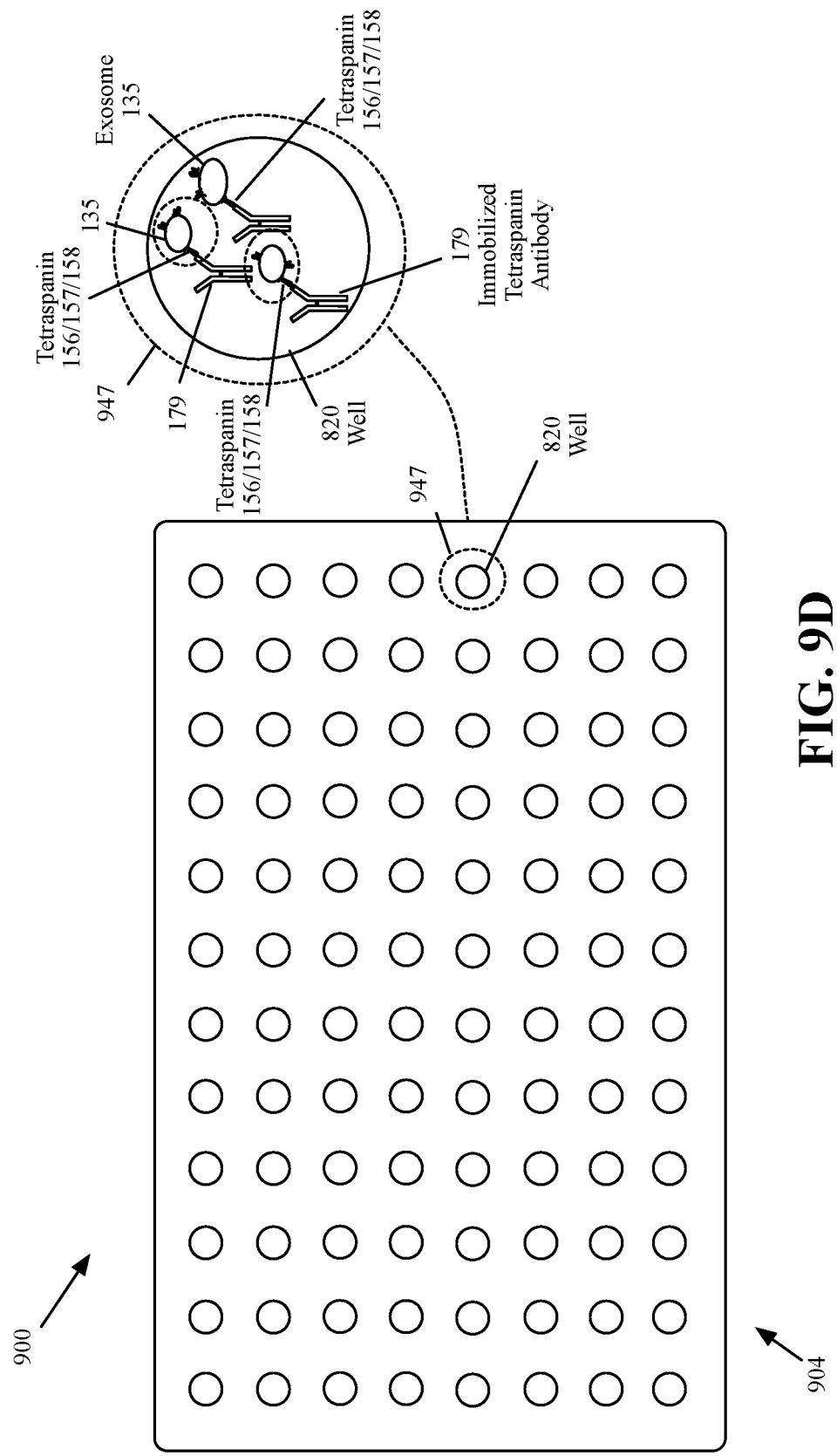
Figure 9E:
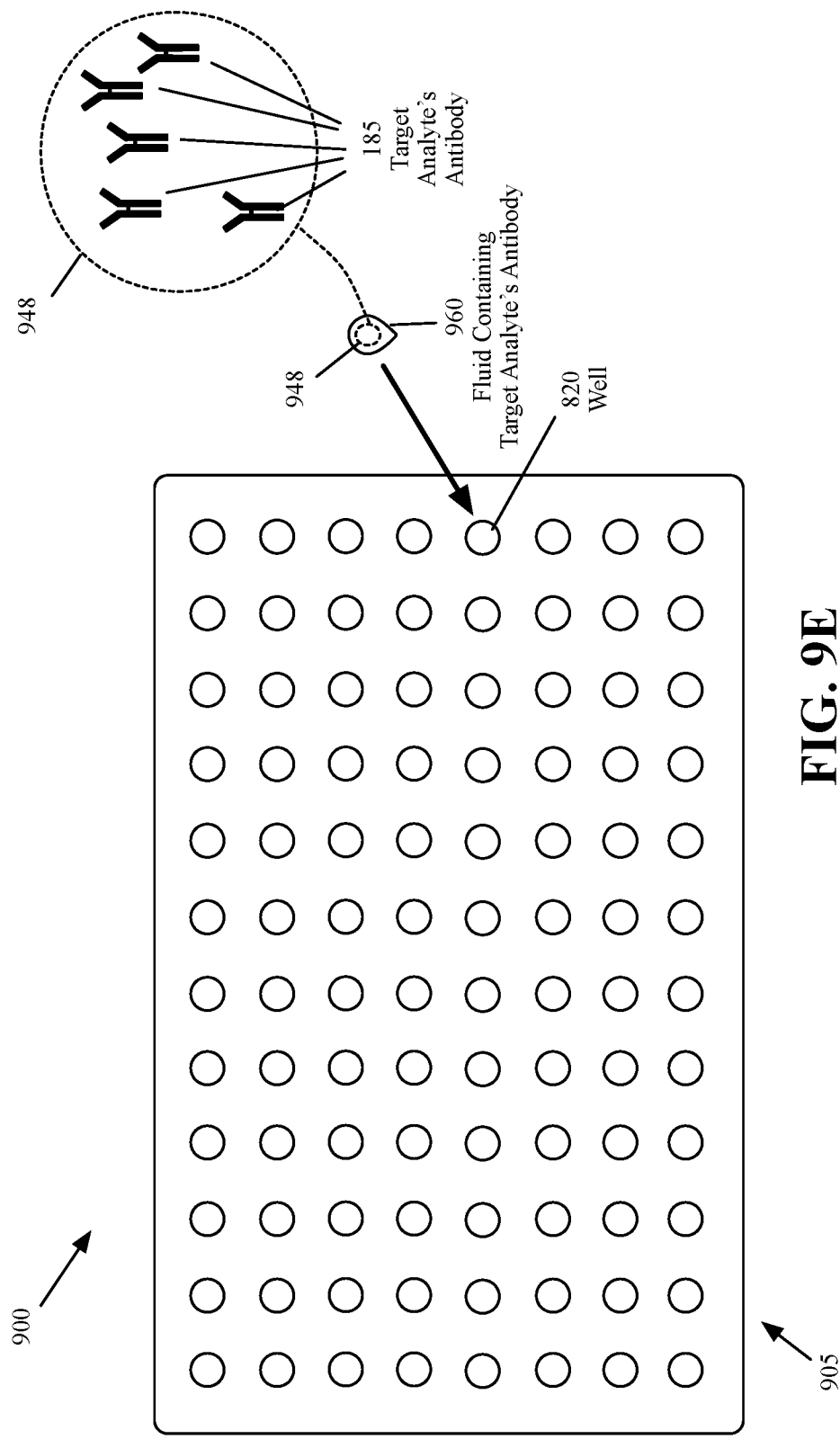
Figure 9F:
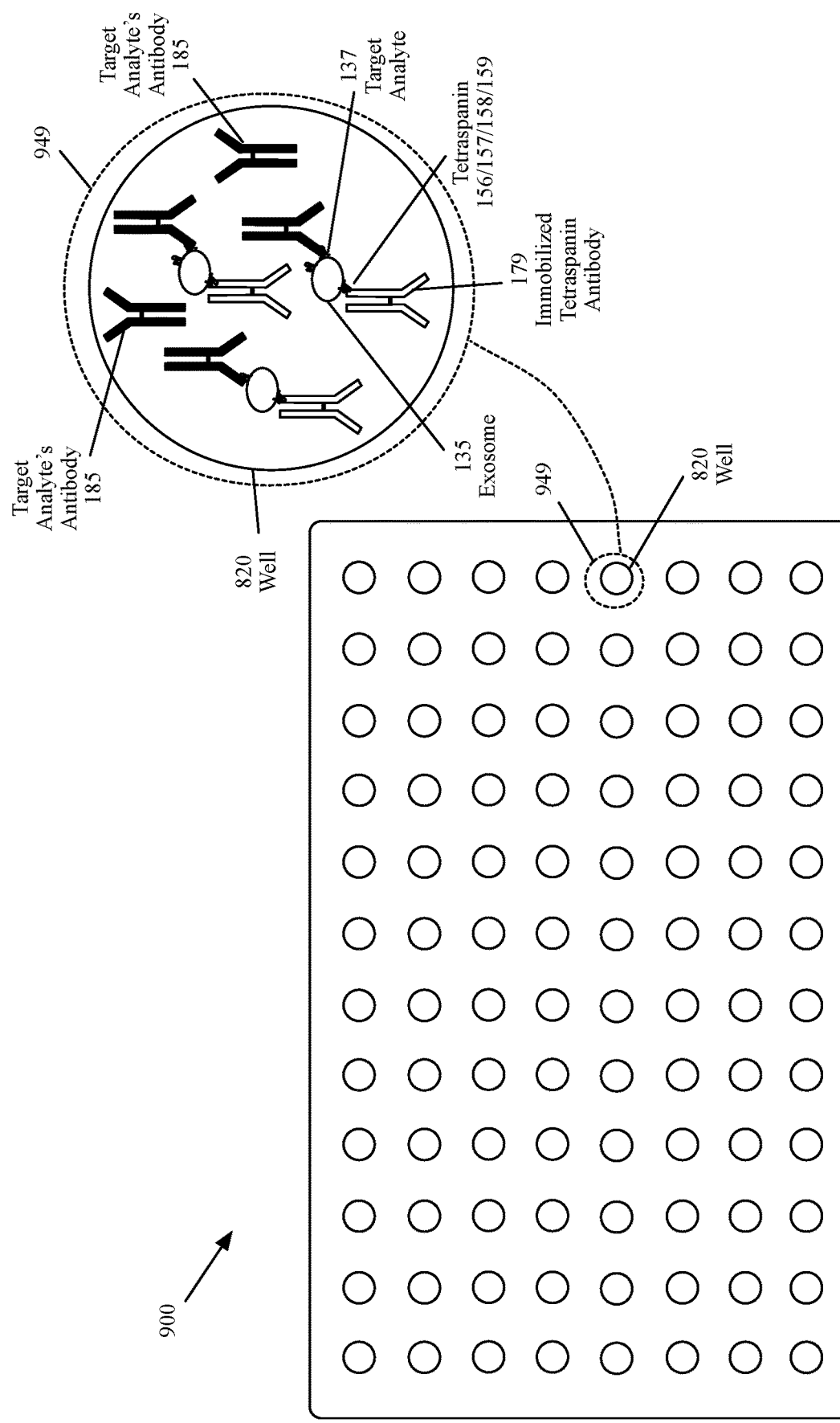
Figure 9G:
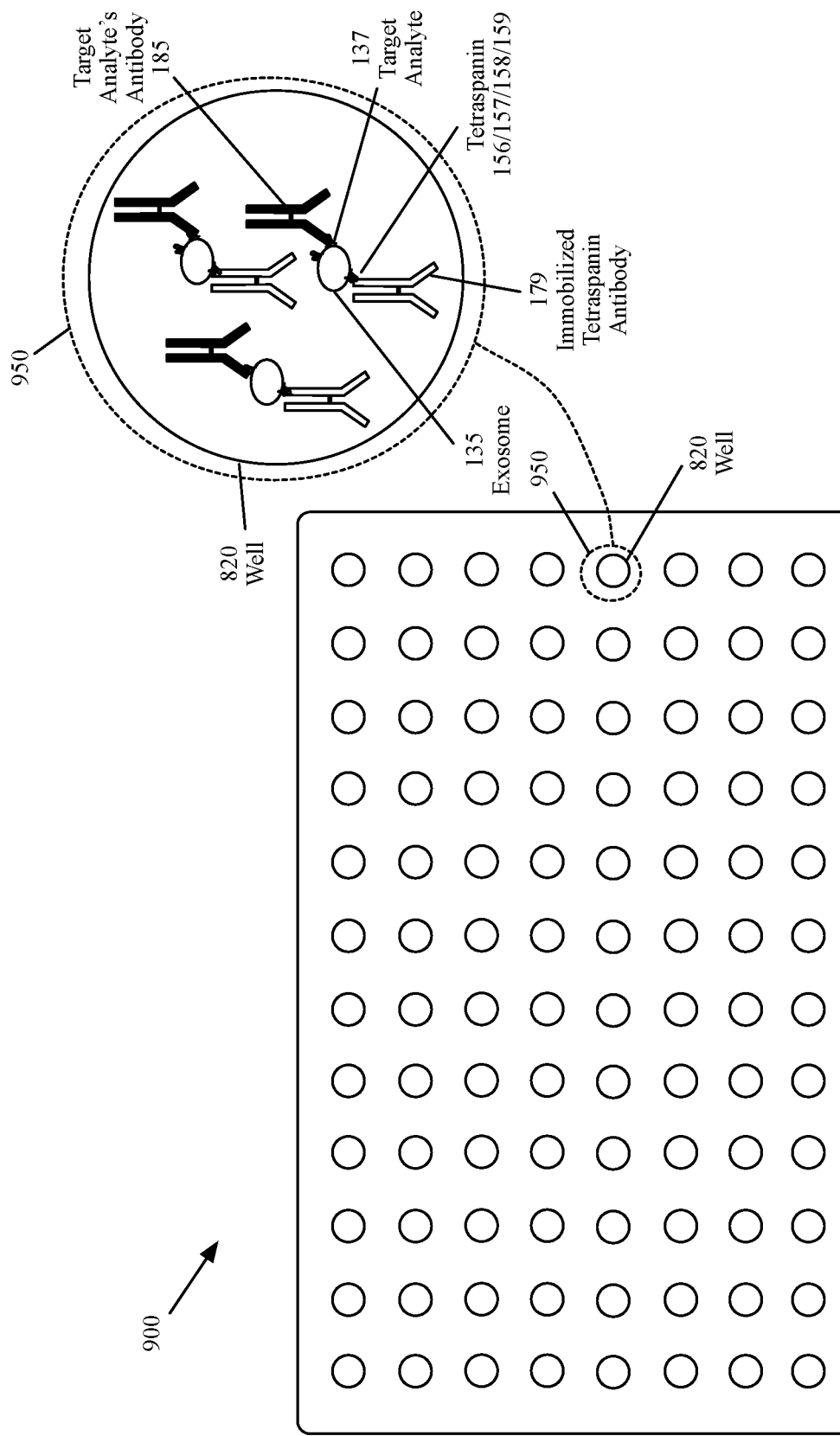
Figure 9H:
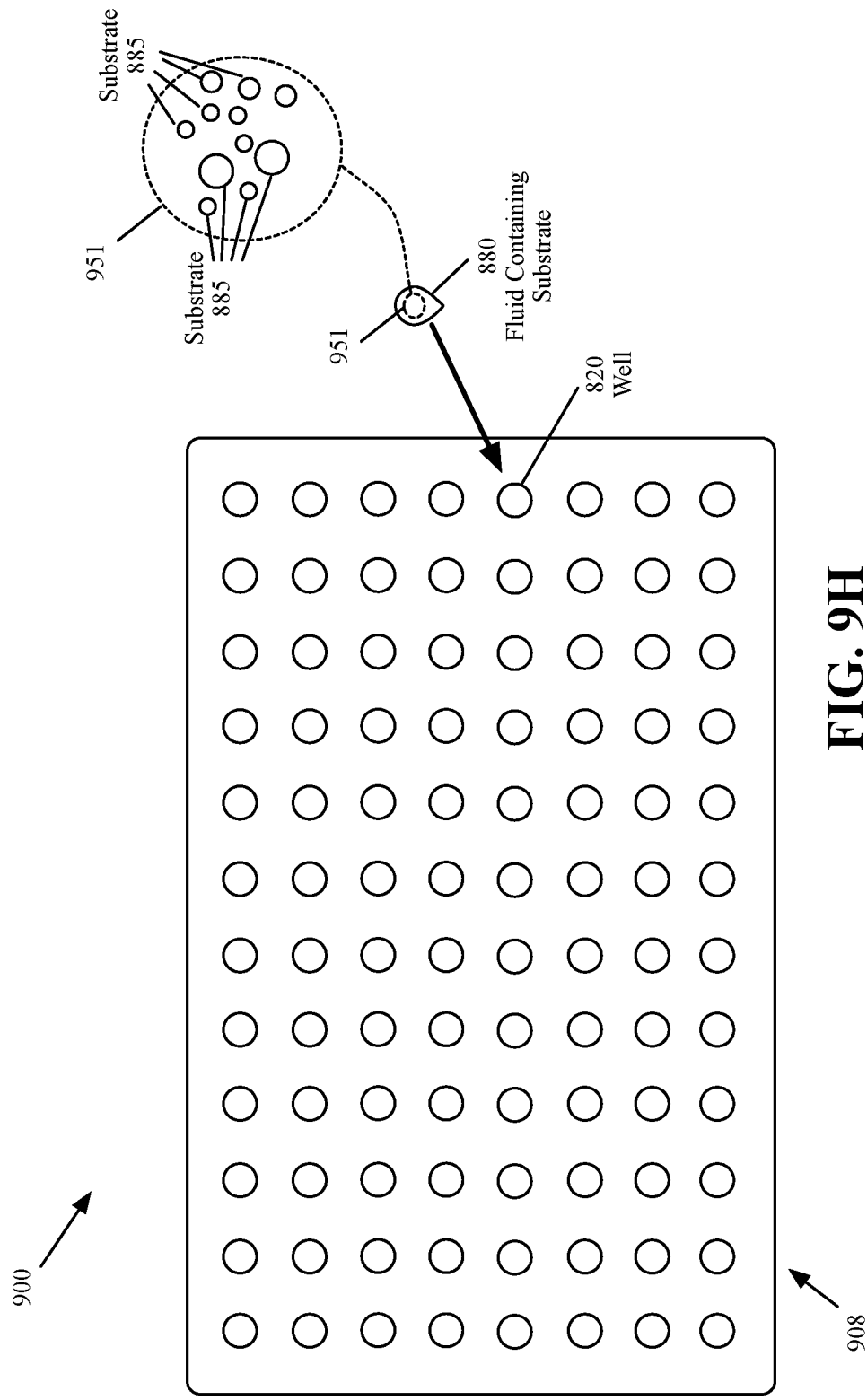
Figure 9I:
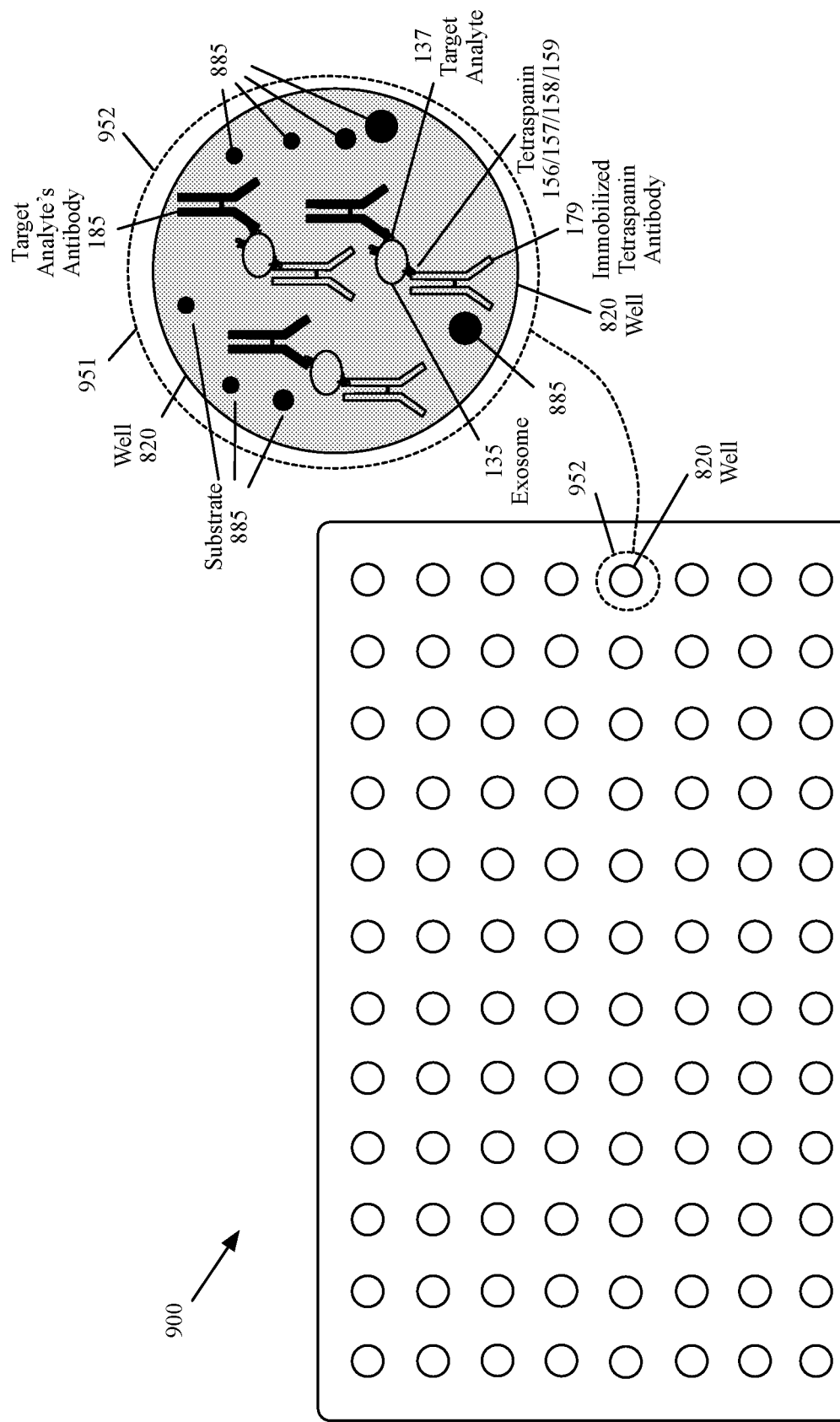

In stage 805 (FIG. 8E), a quantity of fluid 860 containing the tetraspanin antibodies may be added to the well(s) 820. As shown in the expanded view 846, the tetraspanin antibodies (e.g., the tetraspanin antibodies 876-879) may include antibodies to bind to the corresponding tetraspanins (e.g., the tetraspanins 156-159) on the surface of the exosomes that may be immobilized in the well(s) 820 in stage 804 (FIG. 8D). The tetraspanin antibodies 876-879 may include enzymes that may change color after interacting with substrate material that may be added to the well(s) at a later stage of the test.

In stage 806 (FIG. 8F), the tetraspanin antibodies may bind with the corresponding tetraspanins that are on the surface of the immobilized exosomes. As shown in the expanded view 847, the tetraspanin antibodies 876-879 may bind with the corresponding tetraspanins 156-159 that are on the surface of the immobilized exosomes 135. Some of the tetraspanin antibodies 870 may not bind with any exosomes either because there may be excess tetraspanin antibodies in the fluid 860 (FIG. 8E) containing the tetraspanin antibodies or there may not be a matching tetraspanin on the surface of the exosomes 135.

In stage 807 (FIG. 8G), the unbound tetraspanin antibodies 870 (FIG. 8F) may be washed away. In some embodiments, washing may be performed one or more times by applying a washing buffer to thoroughly remove the unbound material. As shown in the expanded view 848, only the tetraspanin antibodies 876-879 that bind with the corresponding tetraspanins 156-159 that are on the surface of the immobilized exosomes 135 may be left in the well(s) 820 at the end of stage 807.

In stage 808 (FIG. 8H), a liquid 880 containing a quantity of substrate 885 may be added to the well(s) 820. The substrate 885, shown in the expanded view 849, may be converted by the enzyme on the tetraspanin antibodies 876-879.

As shown in the expanded view 851 in stage 809 (FIG. 8I), the substrate 885 may be converted by the enzyme on the tetraspanin antibodies 876-878 to produce a color change 895, with intensity proportional to the amount of target analyte 137 present. Depending on the enzyme and substrate used, the readout may also be fluorescent or luminescent. The colored end product may be read in a spectrophotometer as absorbance values, representing the analyte concentration. If the sample fluid did not contain exosomes with the target analyte, the color of the end product may not change, indicating the lack of the target analyte in the sample fluid.

In the embodiments of FIGS. 8A-8I, the target analyte's antibody 185 is immobilized in ELISA device well(s) 820. In other embodiments, such as the embodiments described below with reference to FIGS. 9A-9I, the tetraspanin antibody may be immobilized in ELISA device well(s) 820.

FIGS. 9A-9I are functional diagrams illustrating an ELISA device 900 and a method that detects and captures a target analyte by using immobilized antibodies specific to exosomes containing the target analyte and an antibody specific to the target analyte, according to various aspects of the present disclosure. The structure of the ELISA device 900 may be similar to the structure of the ELISA device 800 of FIGS. 8A-8I.

FIGS. 9A-9I, as shown, include nine stages 901-909. As shown in the expanded view 941 in stage 901 (FIG. 9A), the antibody 179 of one or more types of tetraspanin proteins may be immobilized on the bottom of one or more of the wells 820. The antibody 179 may be the antibody to tetraspanin proteins 159 (FIG. 1A), such as, for example and without limitations, one or more of CD9 tetraspanin protein, CD63 tetraspanin protein, CD81 tetraspanin protein, and CD82 tetraspanin protein, etc., which are present on the surface of the exosomes.

The tetraspanin(s) antibody 179 may be applied as a suitably diluted coating buffer in stage 901 to one or more wells 820 that may be used for a test. The coating buffer may be incubated until adsorbed to the surface of the wells 820. Adsorption may occur passively as the result of hydrophobic interactions between the amino acids side chains on the antibody 179 and the plastic surface of the wells 820. The adsorption may be dependent on time, temperature, and the pH of the coating buffer, as well as the concentration of the antibody 179.

In stage 902 (FIG. 9B), the sample fluid 190 may be added to the well(s) 820 that is/are used in the test. As shown in the expanded view 842, the sample fluid may have a similar composition as the sample fluid of FIGS. 1A and 8B. As shown in the expanded view 843, the exosomes 135 may have similar composition as the exosomes described above with reference to FIG. 1A.

In stage 903 (FIG. 9C), the tetraspanins on the surface of the exosomes 135 may bind with the immobilized tetraspanin antibodies 179 in the well(s) 820.

As shown in the expanded view 944, the tetraspanins (e.g., the tetraspanins 156-159) on the surface of the exosomes 135 in the sample fluid material may bind with the corresponding tetraspanin antibodies (e.g., the tetraspanin antibodies 179). In stage 903, some of the exosomes 135 (e.g., as shown in the expanded view 945) may contain the target analyte 137 on their surface while some of the exosomes 135 (e.g., as shown in the expanded view 946) may not contain the target analyte 137. It should be noted that, depending on the condition of the subject (e.g., a person or an animal) from which the sample fluid 190 (FIG. 9C) is drawn, there may or may not be any exosome with the target analyte 137 in the sample fluid.

The exosomes 135 that are bound with the corresponding tetraspanin antibodies 179 may form immunocomplexes. The fluid sample may be left a suitable time in the well(s) 820 in order for the tetraspanins on the surface of the exosomes 135 to bind with the immobilized corresponding tetraspanins antibodies 179.

In stage 904 (FIG. 9D), the unbound material 198 and 835 (FIG. 9C) may be washed away. In some embodiments, washing may be performed one or more times by applying a washing buffer to thoroughly remove the unbound material. As shown in the expanded view 947, only the exosomes 135 with tetraspanins bound to the immobilized tetraspanin antibodies 179 may be left in the well(s) 820 at the end of stage 904.

In stage 905 (FIG. 9E), a quantity of fluid 960 containing the target analyte's antibodies 185 (as shown in the expanded view 948) may be added to the well(s) 820. The target analyte's antibodies 185 may include enzymes that may change color after interacting with substrate material that may be added to the well(s) at a later stage of the test.

In stage 906 (FIG. 9F), the target analyte's antibodies 185 may bind (as shown in the expanded view 949) with the target analyte 137 that are on the surface of the exosomes that are bound to the immobilized tetraspanin antibodies 179. Some of the target analyte antibodies 185 may not bind with any target analyte 137, for example, because there may be excess target analyte's antibodies 185 in the fluid 860 (FIG. 9E) containing the target analyte's antibodies 185.

In stage 907 (FIG. 9G), the unbound target analyte's antibodies 185 (FIG. 9F) may be washed away. In some embodiments, washing may be performed one or more times by applying a washing buffer to thoroughly remove the unbound material. As shown in the expanded view 950, only the target analyte antibodies 185 that bind with the target analytes 137 that are on the surface of the immobilized exosomes 135 may be left in the well(s) 820 at the end of stage 907.

In stage 908 (FIG. 9H), a liquid 880 containing a quantity of substrate 885 may be added to the well(s) 820. The substrate 885, shown in the expanded view 951, may be converted by the enzyme on the tetraspanin antibodies 876-878.

As shown in the expanded view 952 in stage 909 (FIG. 9I), the substrate 885 may be converted by the enzyme on the target analyte antibodies 185 to produce a color change 895, with intensity proportional to the amount of target analyte 137 present. Depending on the enzyme and substrate used, the readout may also be fluorescent or luminescent. The colored end product may be read in a spectrophotometer as absorbance values, representing the analyte concentration. If the sample fluid did not contain exosomes with the target analyte, the color of the end product may not change, indicating the lack of the target analyte in the sample fluid.

In a first aspect, a lateral flow assay device is provided. The lateral flow assay device comprises a test strip that is configured to receive a quantity of fluid comprising a quantity of exosomes and detect a presence of a target analyte on a surface of the exosomes. The test strip comprises a conjugate pad. The conjugate pad is configured to contain a set of one or more types of tetraspanin binding reagents conjugated with a label. Each type of tetraspanin binding reagent is configured to bind with a corresponding type of exosome tetraspanin and form an immunocomplex comprising an exosome. The conjugate pad is configured to receive the fluid after a start of a test and move the fluid by capillary action. The test strip comprises a membrane that is fluidly connected to the conjugate pad. The membrane is configured to move the fluid by capillary action. The membrane comprises a test line comprising an immobilized binding reagent to the target analyte. The immobilized binding reagent to the target analyte is configured to bind to a protein of the target analyte on the surface of an exosome in an immunocomplex comprising the exosome.

In an embodiment of the first aspect, where the test line is a first test line, the membrane further comprises a second test line comprising an immobilized binding reagent to a first type of protein. The first type of protein is one of a tumor-specific protein and an organ-specific protein. The binding reagent to the first type of protein is configured to bind to the first type of protein on the surface of the exosomes in the immunocomplexes comprising exosomes.

In another embodiment of the first aspect, the binding regent to the target analyte is an antibody of the target analyte. Each type of tetraspanin binding reagent is a type of tetraspanin antibody. The binding reagents to the first type of protein is an antibody to the first type of protein.

In another embodiment of the first aspect, where the test line is a first test line, the membrane further comprises a plurality of test lines other than the first test line, wherein each test line in the plurality of test lines comprises an immobilized binding reagent to one of a corresponding plurality of types of proteins, wherein each type of protein in the plurality of types of proteins is one of a tumor-specific protein and an organ-specific protein, wherein the binding reagent on each test line in the plurality of test lines is configured to bind to the corresponding type of protein on the surface of the exosomes in the immunocomplexes comprising exosomes.

In another embodiment of the first aspect, where the test strip is a first test strip, the lateral flow assay device further comprises a second test strip. The second test strip comprises a conjugate pad. The conjugate pad of the second test strip is configured to contain the set of one or more types of tetraspanin antibodies conjugated with the label. The conjugate pad of the second test strip is configured to receive the fluid after the start of the test and move the fluid by capillary action. The second test strip comprises a membrane fluidly connected to the conjugate pad of the second test strip. The membrane of the second test strip is configured to move the fluid by capillary action. The membrane of the second test strip comprises a test line comprising immobilized binding reagents to a first type of protein. The first type of protein is one of a tumor-specific protein and an organ-specific protein. The binding reagent to the first type of protein is configured to bind to the first type of protein on the surface of the exosomes in the immunocomplexes comprising exosomes.

In another embodiment of the first aspect, where the test strip is a first test strip, the lateral flow assay device further comprises a plurality of test strips other than the first test strip. Each test strip in the plurality of test strips comprises a conjugate pad. The conjugate pad of each test strip in the plurality of test strips is configured to contain the set of one or more types of tetraspanin antibodies conjugated with the label. The conjugate pad of each test strip in the plurality of test strips is configured to receive the fluid after the start of the test and move the fluid by capillary action. Each test strip in the plurality of test strips comprises a membrane fluidly connected to the conjugate pad of the corresponding test strip. The membrane of each test strip in the plurality of test strips is configured to move the fluid by capillary action. The membrane of each test strip in the plurality of test strips comprises a test line comprising immobilized binding reagents to one of a corresponding plurality of types of proteins. Each type of protein in the plurality of types of proteins is one of a tumor-specific protein and an organ-specific protein. The binding reagents on the test line of each test strip in the plurality of test strips is configured to bind to the corresponding type of protein on the surface of the exosomes in the immunocomplexes comprising exosomes.

In another embodiment of the first aspect, the membrane comprises a control line comprising an immobilized binding reagent against a class of the tetraspanin binding reagents that the conjugate pad contains.

In another embodiment of the first aspect, the label is a detector comprising at least one of metallic sols comprising colloidal gold, dye sols, colored latex particles, carbon, fluorescent particles, europium labels, etc.

An embodiment of the first aspect further comprises a wicking pad configured to maintain a capillary flow from the membrane into the wicking pad; and a sample pad configured to receive the fluid and transfer the sample fluid by capillary action to the conjugate pad.

An embodiment of the first aspect further comprises a plasma filter configured to receive the fluid and transfer the fluid to one of the conjugate pad and a sample pad of the lateral flow assay device.

In a second aspect, a lateral flow assay device is provided. The lateral flow assay device comprises a test strip configured to receive a quantity of fluid comprising a quantity of exosomes and detect a presence of a target analyte on a surface of the exosomes. The test strip comprises a conjugate pad. The conjugate pad is configured to contain a binding reagent to the target analyte conjugated with a label. The binding reagent to the target analyte is configured to bind to a protein of the target analyte on the surface of an exosome and form an immunocomplex comprising an exosome. The conjugate pad is configured to receive the fluid after a start of a test and move the fluid by capillary action. The test strip comprises a membrane fluidly connected to the conjugate pad. The membrane is configured to move the fluid by capillary action. The membrane comprises a test line comprising a set of one or more types of tetraspanin binding reagents immobilized on the test line. Each type of tetraspanin binding reagent is configured to bind with a corresponding type of exosome tetraspanin in an immunocomplex comprising the exosome.

In an embodiment of the second aspect, where the test line is a first test line, the membrane further comprises a second test line comprising an immobilized binding reagent to a first type of protein. The first type of protein is one of a tumor-specific protein and an organ-specific protein. The binding reagent to the first type of protein is configured to bind to the first type of protein on the surface of the exosomes in the immunocomplexes comprising exosomes.

In another embodiment of the second aspect, the binding regent to the target analyte is an antibody of the target analyte. Each type of tetraspanin binding reagent is a type of tetraspanin antibody. The binding reagents to the first type of protein is an antibody to the first type of protein.

In another embodiment of the second aspect, where the test line is a first test line, the membrane further comprises a plurality of test lines other than the first test line. Each test line in the plurality of test lines comprises an immobilized binding reagent to one of a corresponding plurality of types of proteins. Each type of protein in the plurality of types of proteins is one of a tumor-specific protein and an organ-specific protein. The binding reagent on each test line in the plurality of test lines is configured to bind to the corresponding type of protein on the surface of the exosomes in the immunocomplexes comprising exosomes.

In another embodiment of the second aspect, where the test strip is a first test strip, the lateral flow assay device further comprises a second test strip. The second test strip comprises a conjugate pad. The conjugate pad of the second test strip is configured to contain the binding reagent to the target analyte conjugated with the label. The conjugate pad of the second test strip is configured to receive the fluid after the start of the test and move the fluid by capillary action. The second test strip comprises a membrane fluidly connected to the conjugate pad of the second test strip. The membrane of the second test strip is configured to move the fluid by capillary action. The membrane of the second test strip comprises a test line comprising immobilized binding reagents to a first type of protein. The first type of protein is one of a tumor-specific protein and an organ-specific protein. The binding reagent to the first type of protein is configured to bind to the first type of protein on the surface of the exosomes in the immunocomplexes comprising exosomes.

In another embodiment of the second aspect, where the test strip is a first test strip, the lateral flow assay device further comprises a plurality of test strips other than the first test strip. Each test strip in the plurality of test strips comprises a conjugate pad. The conjugate pad of each test strip in the plurality of test strips is configured to contain the binding reagent to the target analyte conjugated with the label. The conjugate pad of each test strip in the plurality of test strips is configured to receive the fluid after the start of the test and move the fluid by capillary action. Each test strip in the plurality of test strips comprises a membrane fluidly connected to the conjugate pad of the corresponding test strip. The membrane of each test strip in the plurality of test strips is configured to move the fluid by capillary action. The membrane of each test strip in the plurality of test strips comprises a test line comprising immobilized binding reagents to one of a corresponding plurality of types of proteins. Each type of protein in the plurality of types of proteins is one of a tumor-specific protein and an organ-specific protein. The binding reagents on the test line of each test strip in the plurality of test strips is configured to bind to the corresponding type of protein on the surface of the exosomes in the immunocomplexes comprising exosomes.

In another embodiment of the second aspect, the membrane comprises a control line comprising an immobilized binding reagent against a class of the binding reagent to the target analyte that the conjugate pad contains.

In another embodiment of the second aspect, the label is a detector comprising at least one of metallic sols comprising colloidal gold, dye sols, colored latex particles, carbon, fluorescent particles, europium labels, etc.

An embodiment of the second aspect further comprises a wicking pad configured to maintain a capillary flow from the membrane into the wicking pad; and a sample pad configured to receive the fluid and transfer the sample fluid by capillary action to the conjugate pad.

Another embodiment of the second aspect further comprises a plasma filter configured to receive the fluid and transfer the fluid to one of the conjugate pad and a sample pad of the lateral flow assay device.

In a third aspect, a method and an immunoassay device are provided that receive a quantity of fluid comprising a quantity of exosomes and detect the presence of a target analyte on the surface of the exosomes. The immunoassay device comprises a detection site and a capture site. The method and the immunoassay device perform a fluid transfer between the detection site and a capture site. The detection site is configured to contain a set of one or more types of tetraspanin binding reagents conjugated with a label. Each type of tetraspanin binding reagent is configured to bind with a corresponding type of exosome tetraspanin and form an immunocomplex comprising an exosome. The capture site includes an immobilized binding reagent to the target analyte. The immobilized binding reagent to the target analyte is configured to bind to a protein of the target analyte on the surface of an exosome in an immunocomplex comprising the exosome.

In an embodiment of the third aspect, the detection site and the capture site are different areas of the immunoassay device.

In an embodiment of the third aspect, where the detection site and the capture site are different areas of the immunoassay device, the immunoassay device is a lateral flow assay device.

In an embodiment of the third aspect, the detection site and the capture site are the same area of the immunoassay device.

In an embodiment of the third aspect, where the detection site and the capture site are the same area of the immunoassay device, the immunoassay device is an ELISA device.

In an embodiment of the third aspect, the fluid transfer between the detection site and a capture site is performed by capillary action.

In an embodiment of the third aspect, where the fluid transfer between the detection site and a capture site is performed by capillary action, the immunoassay device is one of an LFA device and a microfluidic device.

In an embodiment of the third aspect, the fluid transfer between the detection site and a capture site is performed by a microfluidic chip or medium.

In an embodiment of the third aspect, the fluid transfer between the detection site and a capture site is performed by an automated liquid handling system.

In an embodiment of the third aspect, where the fluid transfer between the detection site and a capture site is performed by an automated liquid handling system, the immunoassay device is an ELISA device.

In an embodiment of the third aspect, the fluid transfer between the detection site and a capture site is performed by an automated liquid handling system in combination with a microfluidic device.

In an embodiment of the third aspect, the fluid transfer between the detection site and a capture site is performed by manual transfer.

In an embodiment of the third aspect, the fluid transfer between the detection site and a capture site is performed by manual transfer, the immunoassay device is an ELISA device.

In a fourth aspect, a method and an immunoassay device are provided that receive a quantity of fluid comprising a quantity of exosomes and detect the presence of a target analyte on the surface of the exosomes. The immunoassay device comprises a detection site and a capture site. The method and the immunoassay device perform a fluid transfer between the detection site and a capture site. The detection site is configured to contain a binding reagent to the target analyte conjugated with a label. The binding reagent to the target analyte is configured to bind to a protein of the target analyte on the surface of an exosome and form an immunocomplex comprising an exosome. The capture site includes a set of one or more types of tetraspanin binding reagents immobilized on the capture site. Each type of tetraspanin binding reagent is configured to bind with a corresponding type of exosome tetraspanin in an immunocomplex comprising the exosome.

In an embodiment of the fourth aspect, the detection site and the capture site are different areas of the immunoassay device.

In an embodiment of the fourth aspect, where the detection site and the capture site are different areas of the immunoassay device, the immunoassay device is a lateral flow assay device.

In an embodiment of the fourth aspect, the detection site and the capture site are the same area of the immunoassay device.

In an embodiment of the fourth aspect, where the detection site and the capture site are the same area of the immunoassay device, the immunoassay device is an ELISA device.

In an embodiment of the fourth aspect, the fluid transfer between the detection site and a capture site is performed by capillary action.

In an embodiment of the fourth aspect, where the fluid transfer between the detection site and a capture site is performed by capillary action, the immunoassay device is one of an LFA device and a microfluidic device.

In an embodiment of the fourth aspect, the fluid transfer between the detection site and a capture site is performed by a microfluidic chip or medium.

In an embodiment of the fourth aspect, the fluid transfer between the detection site and a capture site is performed by an automated liquid handling system.

In an embodiment of the fourth aspect, where the fluid transfer between the detection site and a capture site is performed by an automated liquid handling system, the immunoassay device is an ELISA device.

In an embodiment of the fourth aspect, the fluid transfer between the detection site and a capture site is performed by an automated liquid handling system in combination with a microfluidic device.

In an embodiment of the fourth aspect, the fluid transfer between the detection site and a capture site is performed by manual transfer.

In an embodiment of the fourth aspect, the fluid transfer between the detection site and a capture site is performed by manual transfer, the immunoassay device is an ELISA device.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure.

What is claimed is:
1. A lateral flow assay device, comprising:
a test strip configured to receive a quantity of fluid comprising a quantity of exosomes and detect a presence of a target analyte on a surface of the exosomes;
wherein the test strip comprises:
a conjugate pad,
wherein the conjugate pad is configured to contain a binding reagent to the target analyte conjugated with a label, wherein target analyte is a protein and the binding reagent binds to the protein and forms an immunocomplex comprising the exosomes; and
wherein the conjugate pad is configured to receive the fluid after a start of a test and move the fluid by capillary action, and
a membrane fluidly connected to the conjugate pad,
wherein the membrane is configured to move the fluid by capillary action, and
wherein the membrane comprises:
a first test line comprising a set of one or more types of tetraspanin binding reagents immobilized on the test line, wherein each type of tetraspanin binding reagent is configured to bind with a corresponding type of exosome tetraspanin in an immunocomplex comprising the exosome, and
a second test line comprising an immobilized binding reagent to a first tumor-specific protein which is not the same protein as the target analyte, and wherein the binding reagent to the first tumor-specific protein binds to the first tumor-specific protein on the surface of the exosomes in the immunocomplex comprising the exosomes.

2. The lateral flow assay device of claim 1, wherein the binding reagent to the target analyte is an antibody specific for the target analyte, wherein the one or more tetraspanin binding reagent is an anti-tetraspanin antibody, and wherein the binding reagent to the first tumor-specific protein is an antibody to the first tumor-specific protein.

3. The lateral flow assay device of claim 1, wherein the membrane further comprises one or more test lines other than the first and second test lines, wherein each test line in the one or more test lines comprises an immobilized binding reagent to one or more types of tumor-specific proteins, wherein the binding reagent on each test line in the one or more test lines binds to the one or more tumor-specific proteins on the surface of the exosomes in the immunocomplex comprising the exosomes.

4. The lateral flow assay device of claim 1, wherein the test strip is a first test strip, wherein the lateral flow assay device further comprises a second test strip, wherein the second test strip comprises:
a conjugate pad,
wherein the conjugate pad of the second test strip is configured to contain the binding reagent to the target analyte conjugated with the label; and
wherein the conjugate pad of the second test strip is configured to receive the fluid after the start of the test and move the fluid by capillary action, and a membrane fluidly connected to the conjugate pad of the second test strip,
wherein the membrane of the second test strip is configured to move the fluid by capillary action, and
wherein the membrane of the second test strip comprises a test line comprising immobilized binding reagents to a first type of protein, wherein the first type of protein is a tumor-specific protein, and wherein the binding reagent binds to the first type of protein on the surface of the exosomes in the immunocomplex comprising the exosomes.

5. The lateral flow assay device of claim 1, wherein the test strip is a first test strip, wherein the lateral flow assay device further comprises a plurality of test strips other than the first test strip, wherein each test strip in the plurality of test strips comprises:

a conjugate pad,
wherein the conjugate pad of each test strip in the plurality of test strips is configured to contain the binding reagent to the target analyte conjugated with the label; and
wherein the conjugate pad of each test strip in the plurality of test strips is configured to receive the fluid after the start of the test and move the fluid by capillary action, and a membrane fluidly connected to the conjugate pad of the corresponding test strip,
wherein the membrane of each test strip in the plurality of test strips is configured to move the fluid by capillary action, and
wherein the membrane of each test strip in the plurality of test strips comprises a test line comprising immobilized binding reagents to one of a corresponding plurality of types of proteins, wherein each type of protein in the plurality of types of proteins is a different tumor-specific protein, and wherein the binding reagents on the test line of each test strip in the plurality of test strips binds to the corresponding type of protein on the surface of the exosomes in the immunocomplex comprising the exosomes.

6. The lateral flow assay device of claim 1, wherein the binding reagent to the target analyte is an antibody, and wherein the membrane comprises a control line comprising an immobilized binding reagent against a class of the antibody to the target analyte.

7. The lateral flow assay device of claim 1, wherein the label is at least one selected from the group consisting of metallic sols comprising colloidal gold, dye sols, colored latex particles, carbon, fluorescent particles, and europium labels.

8. The lateral flow assay device of claim 1 further comprising:

a wicking pad configured to maintain a capillary flow from the membrane into the wicking pad; and
a sample pad configured to receive the fluid and transfer the sample fluid by capillary action to the conjugate pad.

9. The lateral flow assay device of claim 1 further comprising a plasma filter configured to receive the fluid and transfer the fluid to one of the conjugate pad and a sample pad of the lateral flow assay device.

* * * * *